US006057094A

United States Patent [19]
de la Torre

[11] Patent Number: 6,057,094
[45] Date of Patent: May 2, 2000

[54] METHODS AND COMPOSITIONS FOR SCREENING OF HUMAN BORNA DISEASE VIRUS

[75] Inventor: Juan Carlos de la Torre, Solana Beach, Calif.

[73] Assignee: The Scripps Research Institute, La Jolla, Calif.

[21] Appl. No.: 08/779,764

[22] Filed: Jan. 9, 1997

[51] Int. Cl.[7] ............................... C12Q 1/68; C12Q 1/70
[52] U.S. Cl. ........................................ 435/5; 435/6
[58] Field of Search ...................... 424/204.1; 435/89, 435/91.1, 320.1, 5, 6; 536/23.1, 23.72

[56] References Cited

U.S. PATENT DOCUMENTS

| | | | |
|---|---|---|---|
| 5,654,401 | 8/1997 | Clements et al. | 530/350 |
| 5,723,293 | 3/1998 | Huang | 435/6 |

FOREIGN PATENT DOCUMENTS

96/210020  11/1996  WIPO .

OTHER PUBLICATIONS

Briese et al. "Genomic organization of Borna disease virus". PNAS. vol. 91, pp 4362–4366, May 1994.

Cubitt et al. "Sequence and genome organization of borna disease virus". Journal of Virology. vol. 68, No. 3, pp 1382–1396, Mar. 1994.

Kishi et al. "Sequence variability of borna disease virus open reading frame II found in human peripheral blood mononuclear cells". Journal of Virology. vol. 70, No. 1, pp 635–64–, Jan. 1996.

De la Torre et al. "Sequence characterization of human borna disease virus". Virus Research. vol. 44, pp 33–44, 1996.

Kishi et al. "Prevalence of borna disease virus RNA in peripheral blood mononuclear cells from vlood donors". Med. Microbiol. Immunol., vol. 184, pp 135–138, 1995.

Richt et al. "Failure to detect borna disease virus infection in peripheral blood leukocytes from humans with psychiatric disorders". Journal of NeuroVirology. vol. 3, pp 174–18, 1997.

Sauder et al. "Detection of borna disease virus (BDV) antibodies and BDV RNA in psychiatric patients: evidence of high sequence conservation of human blood–derived BDV RNA", Journal of Virology. vol. 70, No. 11, pp 7713–7724, Nov. 1996.

De la Torre et al. "Detection of Borna disease virus antigen and RNA in human autopsy brain samples from neuropsychiatric pateints". Virology. vol. 223, pp 272–282, 1996.

Bode et al. "borna disease virus genome transcribed and expressed in psychiatric patients". Nature Medicine. vol. 1, No. 3, pp 232–236, Mar. 1995.

*Primary Examiner*—Donna Wortman
*Attorney, Agent, or Firm*—Thomas Fitting; Emily Holmes

[57] ABSTRACT

Human Borna disease virus (BDV) nucleic acids and polypeptides are described from three psychiatric patients. The human BDV-derived nucleic acids and polypeptides are useful in both DNA- and protein-based assays to detect human BDV in a subject, particularly the detection of BDV nucleic acids, BDV polypeptides and BDV antibodies generated in response to BDV infection.

7 Claims, 33 Drawing Sheets

FIG. 2A

```
Consensus   CTATAGATTGGATTAACGGCCARCCCTGGGTAGGCTCCTTTGTGTCTCTACTAACTACAGACTTTGAGTCCCCAGGTAAAGAATTYA   720
BDV JCT     ......................G.............................................................C.   720
BDV Briese  ......................A..............................................................T.   720

Consensus   TGGAYCAGATTAARCTTGTCGCAAGTTATGCRCAGATGACTACGTACACTACTATAAAGGAGTACCTCGCAGAATGYATGGATGCTACCC   810
BDV JCT     .....T..A..............G.....................................................T.........   810
BDV Briese  .....C..........G.....A.....................................................C..........   810

Consensus   TTACAATCCCYGTAGTTGCATATGAGATYCGTGACTTTTTAGAAGTTTCAGCAAAGCTTAARGAGGAWCATGCTGACCTGTTYCCGTTYC   900
BDV JCT     .........T.........................................................A.....A........T....C.   900
BDV Briese  .........C..........T...............................................G.........T........T.   900

Consensus   TGGGGGCYATTMGRCACCCCGACGCTATCAAGCTKGCGCCACGRAGCTTTCCCAATCTGGCYTTCYGCAGGCGTTTTACTGGAGTAAGAAGG   990
BDV JCT     .......T..C.G.....................G.......T................T..........................   990
BDV Briese  .......C..A.A........................A...................C..C..........................   990

Consensus   ARAAYCCCACAATGGCRGGCTACCGGGCCTCCCACCATCCAGCCGCCGRAGTGTCAAGGARACCCAGCTTGCCCGGTATAGGCGCCGCG   1080
BDV JCT     .G..T.........G........................................G.............................   1080
BDV Briese  .A..C.........A........................................A.............................   1080

Consensus   AGATATCTCGYGGRGARGACGGGGCAGAGCTCTCAGGTGAGATCTCTGCCATAATGARRATGATAGGTGTGACTGGTCTAAACTARAAAA   1170
BDV JCT     ......C..G..A...................................................GA.....G...........A...   1170
BDV Briese  ......T..A..G...................................................AG.......A.............   1170

Consensus   CAATGAACAAACCAATAAAAAACCAAATGCGGCAAACCCYCCGGACCTGYGATGAGYTCCGACCTCCGGCTGACATTGCTTGAAYTAGT   1260
BDV JCT     .............................................C........T.....T.........................T.   1260
BDV Briese  .............................................T........C..............................C.   1260

Consensus   CAGGGAGGCTCAATGGCAACGSGACCATCGAGTCTGGTCGACTCCCTGAGGACGAAGAAGATCCCCAGACACTACGACGGGAACGAYCGG   1350
BDV JCT     ..................G.......................................................T.............   1350
BDV Briese  ..................C.......................................................C.............   1350
```

```
Consensus   ACTTYACYATTGACGTAGARCCAGCAGTCATTCCCTGGTCAAYATATACTTCCAGATTGACGACTTCTTGCTCCTAACACTCAAC    2160
BDV JCT     .....C...C.................G................................................C..........    2160
BDV Briese  .....T..T.....................A..............................................T..........    2160

Consensus   TRTCYGTRTACAAGGACCCGATTAGRAAATACATGTTCCTACGCCTCAACAAGGAMCAGAGCAAGCACGCAATYAATGCAGCYTTCAATG    2250
BDV JCT     .G..C..A.........................G...........A.................T...C...........         2250
BDV Briese  .A..T.G.........................A.............................C.........                2250

Consensus   TCTTYTCTTATCGGCTTCGGAACATTGGTGTTGGYCCTCTCGGCCCRGACATTGATCTTCAGGGCCTTAGYTGCAATACTGACTCCACT    2340
BDV JCT     ...C..................................................T........C.........................    2340
BDV Briese  ...T..........................................A........G..................................    2340

Consensus   CCTGGAYTRATYGAYCTGGAGATAAGGCGACTTTGCCACACRTCATGCCTCAAGTACCACTGCAAAACCTATTGGGGATTCTTTGGTAGCTACAGCGCTGACCGA    2430
BDV JCT     .....T.A..C..T............................T........C.......                                2430
BDV Briese  .....C.G..T..C............................C.........                                      2430

Consensus   ACTATTAGCCTCCCCGGCAGTCCACACRTCATGCCTCAAGTACCACTGCAAAACCTATTGGGGATTCTTTGGTAGCTACAGCGCTGACCGA    2520
BDV JCT     ..........................G..........................                                      2520
BDV Briese  ..........................A..........................                                      2520

Consensus   ATCATMAATCGGTACACTGGTACTGTTAAGGGTTGTYTAAACAACTCAGCRCCAGAGAYCCCTCGAGTGCAACTGGTTCTACTGCTGC    2610
BDV JCT     .....C...........................T.......G.....T.............                              2610
BDV Briese  .....A..........................C.......A.....                                             2610

Consensus   TCGGCGATTACAACAGAGATCTGCCGATGCTCTATTACAAAATGTCACGGTGGCTGTRCARACATTCCCACCGTTCATGTACTGCAGTTTY    2700
BDV JCT     ..........................................................A..G.........................C    2700
BDV Briese  ..........................................................G..A.........................T    2700

Consensus   GCRGACTGYAGTACYGTGAGYCARCAGGAGCTAGAGAGTGGMAAGGCAATGCTGAGCGATGGCAGTACMTTAACTTATACCCCGTATATC    2790
BDV JCT seq ..G......T......T..G..........................C..........C..............................    2790
BDV Briese  ..A......C......C..A..........................A..........A..............................    2790
```

```
Consensus    CCCTCACGGAGATGGCYCAGYTGCTTGCGAGGGACCTYTCAACAATGATGCCTCTTCGRCCCCGGGATATGTCGGCCTTATTCGCATTAT    6480
BDV JCT      ................C...C................C....................G...............................    6480
BDV Briese   ................T...T................T....................A...............................    6480

Consensus    CAAATGTCGCATAYGGTYTAAGCATTATAGATCTATTTCAAAARTCCTCTACCGTTGTYTCTGCAAGTCAAGCTGTCCATATCGARGATG    6570
BDV JCT      .............T...C.........................G..............C..........................A....    6570
BDV Briese   .............C...T.........................A..............T..........................G....    6570

Consensus    TTGCCCTAGAGAGTGTAAGGTATAAGGAATCTATCATYCAGGGTCTGTTAGACACYACTGAGGGGTAYAACATGCAACCTTATTTGGAAG    6660
BDV JCT      .....................................T.................T...........C......................    6660
BDV Briese   .....................................C.................C...........T......................    6660

Consensus    GTTGCACTTACCTTGCAGCCAARCAGYTACGKAGGTTGACRTGGGGTCGAGACCTAGTTGGAGTYACAATGCCGTTTGTTGCCGAGCAAT    6750
BDV JCT      ......................G...C....G........G.......................T.........................    6750
BDV Briese   ......................A...T....T........A.......................C.........................    6750

Consensus    TCCATCCYCAYAGTTCTGTSGGTGCAAARGCRGAACTCTACCTCGAYGCTATYATATACTGCCCACARGAGACRTTGCGGTCACACCATC    6840
BDV JCT      .......C..T........C........A..A..............T.....C..............A.....G................    6840
BDV Briese   .......T..C........G........G..G..............C.....T..............G.....A................    6840

Consensus    TGACTACCAGGGGGGACCAGCCGCTTTACCTYGGATCYAATACGGCTGTCAMGGTYCAGCGAGGTGAGATCACRGGCCTAACAAAGTCAA    6930
BDV JCT      ...............................T.....T.............C...T.................A................    6930
BDV Briese   ...............................C.....C.............A...C.................G................    6930

Consensus    GGGCTGCAAATCTAGTCARGGACACTCTCGTTCTCCAYCAGTGGTAYAARGTCCGTAARGTTACCGATCCACACTTGAACACYCTCATGG    7020
BDV JCT      ..................A..................C........C..G........G.......................T.......    7020
BDV Briese   ..................G..................T........T..A........A.......................C.......    7020

Consensus    CRCGCTTCTTRCTTGAGAAGGGRTACACATCTGACGCTCGRCCTAGCATYCAGGGTGGGACCCTCACRCATCGTCTCCCATCCCGYGGAG    7110
BDV JCT      .G........G...........A.................G........T.................A.................T....    7110
BDV Briese   .A........A...........G.................A........C.................G.................C....    7110
```

```
Consensus  TYAGGCCTCACCTTGAGGARTTTGAYGARCTGCTTGTGGTRGGRCAGCAYATCCTCGGYCAGCCCGTCCTAGTRGAGGTTGTTTACTACG  8640
BDV JCT    .C.................G......T..A..........G..G....T............G........................  8640
BDV Briese .T.................A......C..G..........A..A....C............A........................  8640

Consensus  TTGGAGTTGTTRGGAAGCGYCTGTGTTAGCGAGGCATCCSTGGTCAGCAGATCTTAAGCGAATYACTGTRGGGGGCGRGCKCCCTGCC  8730
BDV JCT    ............G.........T.................C...............................A..G..........  8730
BDV Briese ............A.........C.........G...............T...............G..T..................  8730

Consensus  CYTCTGCTGCYRGAYTGCGTGATGAGGATTGTCRGGGGTCTCTGYTGGTTGGGCTTCCYGCTGGRTTGACGCAGTTRTTGRTRRTTGATT  8820
BDV JCT    .T.......TG..C.....................G........C.....C..........A..........G...G.GG.......  8820
BDV Briese .C.......CA..T...................A........T.................T..G...........A...A..AA...  8820

Consensus  RAGRTYRAGCCAYCTACTRCCCTATTCTTAAAAAACCATAYGTCAGTGGTGCAGTGCTTGGGYTTGGTTGTTGCTTTGTTGTAGCGCKTT  8910
BDV JCT    G..G.TG....T......G.................C..........................T....-..-........T--....  8908
BDV Briese A..A.CA....C......A.................T..........C................................G......  8910
```

FIG. 2M

```
                    410       420       430       440       450       460       470       480       490       500
                    |         |         |         |         |         |         |         |         |         |
Strain V    TCGGCGAGAACATCAAGATACTAGATGCTCCATGAAGACAATGATGGAGACAATGAAGCTCATGATGGAGAAGGTGGATCTCCTCTACGCATCAACCGC    500
H1          ....................................................................................................    500
H2          ....................................................................................................    500
H3          ...........T.........................G..............................................................    500
C6BV        .................................................................C..................................    500

510       520       530       540       550       560       570       580       590       600
                    |         |         |         |         |         |         |         |         |         |
Strain V    CGTTGGGACCTCTGCACCCATGTTGCCCTCCCATCCTGCACCTCCGGCATTTATCCCGAGCTCCCAAGTGCCCGACAACGGATGAATGGGACATCATA    600
H1          ........................................................................................G...........    600
H2          ...................................................................G....................G...........    600
H3          ........................................................................................G...........    600
C6BV        ....................................................................................................    600

Strain V    CCA                                                                                                      603
H1          ...                                                                                                      603
H2          ...                                                                                                      603
H3          ...                                                                                                      603
C6BV        ...                                                                                                      603
```

```
                 1210      1220      1230      1240      1250      1260      1270      1280      1290      1300
                 |---------|---------|---------|---------|---------|---------|---------|---------|---------|
Strain V  GCAAGTCTCAACATGACCCCTCAGACCAGTATCGCTCGGGTCATGAGACAGACCCCATAAATCATGCCTACGGAACGCAGGCTGATCTCCTTCCATACA  1300
H1        ..........................................................................................  1300
H2        ....................C.....................................................................  1300
H3        .......................................A...................................C..............  1300
C6Bv      ..........................................................................................  1300

1310      1320      1330      1340      1350      1360      1370      1380      1390      1400
                 |---------|---------|---------|---------|---------|---------|---------|---------|---------|
Strain V  CCAGGTCTAGTAATATAACATCTACGGATACAGGCTCAGGCTGGGTGCACATCGGCTCCTCATTTGCTTTCCTCAATCCCCTCGGGTGGCTCAGGGA  1400
H1        ..........................................................................................  1400
H2        ..................G...A...................................................................  1400
H3        ..................G........................................................T..............  1400
C6Bv      ..........................................................................................  1400

1410      1420      1430      1440      1450      1460      1470      1480      1490      1500
                 |---------|---------|---------|---------|---------|---------|---------|---------|---------|
Strain V  CCTACTTGCATGGGCAGCCTGGTTGGGTGGGGTTCTATACTTAATAAGTCTTTGTTTCCTTCCTACCAGCCTCCTTCGCGAGGAGGAGACGCCTCGGCCGG  1500
H1        ..........................................................................................  1500
H2        ....................G.....G...............................................................  1500
H3        ..........................................................................................  1500
C6Bv      ..........................................................................................  1500

1510      1520
                 |---------|----
Strain V  TGGCAGGAATAAACCGTACCG  1521
H1        .T...................  1521
H2        .....................  1521
H3        .....................  1521
C6Bv      .....................  1521
```

```
C6BV p40int      .......... .T........ .......... .......... .........T   350
H1 p40int        .......... .T........ .......... .......... .........C   350
H2 p40int        .......... .G........ .......... .......... .........C   350
H3 p40int        .......... .T........ .......... .......... .........C   350
StrainV p40int   .......... .T........ .......... .......... .........C   350

Consensus        TGATGGCAGC CKTAAACCGG CCATCCCATG GTGAGACTGC TACACTACTY   350

C6BV p40int      .......... .......... .......... .......... ....G.....   400
H1 p40int        .......... .......... .......... .......... ....A.....   400
H2 p40int        .......... .......... .......... .......... ....A.....   400
H3 p40int        .......... .......... .......... .......... ....A.....   400
StrainV p40int   .......... .......... .......... .......... ....A.....   400

Consensus        CAGATGTTTA ATCCACATGA GGCTATAGAT TGGATTAACG GCCARCCCTG   400

C6BV p40int      .......... .........T .......... .......... ..........   450
H1 p40int        .......... .........C .......... .......... ..........   450
H2 p40int        .......... .........T .......... .......... ..........   450
H3 p40int        .......... .........T .......... .......... ..........   450
StrainV p40int   .......... .........T .......... .......... ..........   450

Consensus        GGTAGGCTCC TTTGTGTTGY CTCTACTAAC TACAGACTTT GAGTCCCCAG   450

C6BV p40int      .......... C.....T... .....A.... .......... ...G......   500
H1 p40int        .......... T.....C... .....G.... .......... ...A......   500
H2 p40int        .......... T.....C... .....G.... .......... ...A......   500
H3 p40int        .......... T.....C... .....G.... .......... ...A......   500
StrainV p40int   .......... T.....C... .....G.... .......... ...A......   500

Consensus        GTAAAGAATT YATGGAYCAG ATTAARCTTG TCGCAAGTTA TGCRCAGATG   500

C6BV p40int      .......... .......... .......... ........T. ..........   550
H1 p40int        .......... .......... .......... ........C. ..........   550
H2 p40int        .......... .......... .......... ........C. ..........   550
H3 p40int        .......... .......... .......... ........C. ..........   550
StrainV p40int   .......... .......... .......... ........C. ..........   550

Consensus        ACTACGTACA CTACTATAAA GGAGTACCTC GCAGAATGYA TGGATGCTAC   550

C6BV p40int      .......... ..T....... .                                  571
H1 p40int        .......... ..T....... .                                  571
H2 p40int        .......... ..T....... .                                  571
H3 p40int        .......... ..T....... .                                  571
StrainV p40int   .......... ..C....... .                                  571

Consensus        CCTTACAATC CCYGTAGTTG C                                  571
```

FIG. 5A-2

```
Consensus    TGACCATGAG CTCAACGGCY CTAAQYCAYC TTCTTAACCG GCTATCACAT    50
p180frag     .................C.....C..T...................    50
H1 p180      ...................T...T..C...................    50
H2 p180      ...................T...T..C...................    50
H3 p180      ...................T...T..C...................    50
Strain 5 p180 ..................T....T..C...................    50

Consensus    ACTATCACTA AGGGTGACTC CTTTGTTATT AACYIWGAYT ATAGYTCCTG   100
p180frag     ............................T.A..T.......C.....       100
H1 p180      ............................C.T..C.....T.T.....       100
H2 p180      ............................C.T..C.....T.T.....       100
H3 p180      ............................C.T..C.....T.T.....       100
Strain 5 p180 ...........................C.T..C.....T........       100

Consensus    GTGCAACGGT TTCCGACCAG AACTRCARGC CCCAMTCTGT CGTCAGTTGG   150
p180frag     ....................A...A......C.................      150
H1 p180      ....................G...G......A.................      150
H2 p180      ....................G...G......A.................      150
H3 p180      ....................G...G......A.................      150
Strain 5 p180 ...................G...G......A.................      150

Consensus    ATCAGATGTT CAATTGCGGG TACTTCTTCA GGACTGGGTG CACACTGCCA   200
p180frag     ..................................................      200
H1 p180      ..................................................      200
H2 p180      ..................................................      200
H3 p180      ..................................................      200
Strain 5 p180 ..................................................      200

Consensus    TGCTTTACCA CGTTTATTAT TCARGACAGR TTCAACCCGC CCTATTCCYT   250
p180frag     ..............................G.....A............T.    250
H1 p180      ..............................A.....G............C.    250
H2 p180      ..............................A.....G............C.    250
H3 p180      ..............................A.....G............C.    250
Strain 5 p180 .............................A.....G............C.    250

Consensus    CMGTGGTGAG CCCGTTGAAG ACGGWGTYAC ATGCGCGGTT GGGACTAARA   300
p180frag     .C...........................T.C................G.    300
H1 p180      .A...........................A.T................A.    300
H2 p180      .A...........................A.T................A.    300
H3 p180      .A...........................A.T................A.    300
Strain 5 p180 .A..........................A.T................A.    300
```

FIG. 5B-1

```
Consensus    CAATGGGRGA GGGYATGAGG CAGAAACTAT GGACAATYCT TACGAGCTGC    350
p180frag     ......A.. ....T..... .......... .........T ..........    350
H1 p180      ......G.. ....C..... .......... .........C ..........    350
H2 p180      ......G.. ....C..... .......... .........C ..........    350
H3 p180      ......G.. ....C..... .......... .........C ..........    350
Strain 5 p180 .....G.. ....C..... .......... .........C ..........    350

Consensus    TGGGAGATAA TTGCTCTTCG GGAAATTAAC GTGACGTTTA AYATACTAGG    400
p180frag     .......... .......... .......... .........T ..........    400
H1 p180      .......... .......... .......... .........C ..........    400
H2 p180      .......... .......... .......... .........C ..........    400
H3 p180      .......... .......... .......... .........C ..........    400
Strain 5 p180 ......... .......... .......... .........C ..........    400

Consensus    CCARGGTGAT AATCAGACAA TCATYRTACA TAAATCTGCA AGCCAAAATA    450
p180frag     ...G...... .......... ....TG.... .......... ..........    450
H1 p180      ...A...... .......... ....CA.... .......... ..........    450
H2 p180      ...A...... .......... ....CA.... .......... ..........    450
H3 p180      ...A...... .......... ....CA.... .......... ..........    450
Strain 5 p180 ..A...... .......... ....CA.... .......... ..........    450

Consensus    AYCAGCTATT AGCGGAGCGA GCAYYRGGRG CYYTGTACAA GCATGCTAGA    500
p180frag     .T........ .......... ...T.G..A. .TT....... ..........    500
H1 p180      .C........ .......... ...C.A..G. .CC....... ..........    500
H2 p180      .C........ .......... ...C.A..G. .CC....... ..........    500
H3 p180      .C........ .......... ...C.A..G. .CC....... ..........    500
Strain 5 p180 .C....... .......... ...C.A..G. .CC....... ..........    500

Consensus    TTAGCTGGCC ATAACCTYAA GGTAGARGAA TGYTGGGTGT CAGATTGTCT    550
p180frag     .......... ........T. ......A... ..T....... ..........    550
H1 p180      .......... ........C. ......G... ..C....... ..........    550
H2 p180      .......... ........C. ......G... ..C....... ..........    550
H3 p180      .......... ........C. ......G... ..C....... ..........    550
Strain 5 p180 ......... ........C. ......G... ..C....... ..........    550

Consensus    GTATGAGTAT GGAAAGAAGC TYTTCTTCCG TGGTGTACCT GTCCRGGCT     600
p180frag     .......... ........C. .......... ........A. ...           600
H1 p180      .......... ........T. .......... ........G. ...           600
H2 p180      .......... ........T. .......... ........G. ...           600
H3 p180      .......... ........T. .......... ........G. ...           600
Strain 5 p180 ......... ........T. .......... ........G. ...           600
```

FIG. 5B-2

```
Consensus   GTTTGAAGCA GCTCTORCGG GTGACGGAYT CYACTGGRGA GYTATTCCCA   650 p180frag    .......... ......G... .......... C. .C..... G.. .T........   650
H1 p180     .......... ......A... .......... T. .T..... A.. .TC.......   650
H2 p180     .......... ......A... .......... T. .T..... A.. ..C.......   650
H3 p180     .......... ......A... .......... T. .T..... A.. ..C.......   650
Strain 5 p180 ........ ......A... .......... T. .T..... A.. ..C.......   650

Consensus   AACCTATACT CAAAGTTAGC CTGCTWAACA TCATCRTGY                689 p180frag    .......... .......... .....T.... ....A..C                  689
H1 p180     .......... .......... .....T.... ....A..C                  689
H2 p180     .......... .......... .....T.... ....A..C                  689
H3 p180     .......... .......... .....A.... ....A..C                  689
Strain 5 p180 ........ .......... .....T.... ....G..T                  689
```

| | p24 | | | | p16 | | | p56 | | | | | | | | | | | |
|---|---|---|---|---|---|---|---|---|---|---|---|---|---|---|---|---|---|---|---|
| | 4 | 26 | 34 | 127 | 194 | 12 | 27 | 108 | 3 | 7 | 17 | 21 | 220 | 234 | 242 | 243 | 245 | 282 | 296 | 326 | 412 | 465 | 501 |
| C6BV | G | S | I | H | A | G | D | E | L | S | A | Q | A | V | S | L | R | M | G | A | A | L | W |
| H1 | E | - | - | V | T | D | - | D | P | F | V | R | T | A | P | R | L | V | S | T | T | P | L |
| H2 | - | - | - | V | - | - | - | D | P | F | V | R | T | A | P | R | L | V | S | T | - | P | - |
| H3 | E | - | - | V | T | - | G | D | P | F | V | R | T | A | P | R | L | V | S | T | - | P | - |
| Strain V | R | P | - | V | T | D | - | D | P | F | V | R | T | A | P | R | L | V | - | - | - | P | - |

FIG. 6B

| | p24 | | | | p16 | | | | p56 | | | |
|---|---|---|---|---|---|---|---|---|---|---|---|---|
| | C6BV | H1 | H2 | H3 | Strain V | C6BV | H1 | H2 | H3 | Strain V | C6BV | H1 | H2 | H3 | Strain V |
| C6BV | | 16 | 14 | 14 | 17 | | 17 | 16 | 17 | 16 | | 67 | 65 | 65 | 64 |
| H1 | 4 | | 2 | 1 | 5 | 2 | | 2 | 3 | 3 | 15 | | 2 | 2 | 3 |
| H2 | 2 | 2 | | 1 | 3 | 1 | 1 | | 1 | 1 | 13 | 2 | | 0 | 1 |
| H3 | 3 | 1 | 1 | | 5 | 2 | 2 | 1 | | 2 | 13 | 2 | 0 | | 1 |
| Strain V | 4 | 3 | 2 | 2 | | 1 | 1 | 0 | 1 | | 12 | 3 | 1 | 1 | |

MATEPSSLVDSLEDEEDPQTLRRERSGSPRPRKVPRNALTQPVDQLLKDLRKNPSMISDP
DQRTGREQLSNDELIKKLVTELAENSMIEAEEVRGTLGDISARIEAGFESLSALQVETIQT
AQRCDYSDSIRILGENIKILDRSMKTMMETMKLMMEKVDLLYASTAVGTSAPMLPSHP
APPRIYPQLPSAPTTDEWDIIP

FIG. 8A

MATGPSSLVDSLEDEEDPQTLRRERSGSPRPRKVPRNALTQPVDQLLKDLRKNPSMISDP
DQRTGREQLSNDELIKKLVTELAENSMIEAEEVRGTLGDISARIEAGFESLSALQVETIQT
AQRCDHSDSIRILGENIKILDRSMKTMMETMKLMMEKVDLLYASTAVGTSAPMLPSHP
APPRIYPQLPSAPTTDEWDIIP

FIG. 8B

MATEPSSLVDSLEDEEDPQTLRRERSGSPRPRKVPRNALTQPVDQLLKDLRKNPSMISDP
DQRTGREQLSNDELIKKLVTELAENSMIEAEEVRGTLGDISARIEAGFESLSALQVETIQT
AQRCDHSDSIRILGENIKILDRSMKTMMETMKLMMEKVDLLYASTAVGTSAPMLPSHP
APPRIYPQLPSAPTTDEWDIIP

FIG. 8C

MNSKHSYVELKDKVIVPGWPTLMLEIDFVGGTSRNQFLNIPFLSVKEPLQLPREKKLTDY
FTIDVEPAGHSLVNIYFQIDDFLLLTLNSLSVYKDPIRKYMFLRLNKDQSKHAINAAFNVF
SYRLRNIGVGPLGPDIRSSGP

FIG. 9A

MNSKHSYVELKDKVIVPGWPTLMLEIDFVGGTSRNQFLNIPFLSVKEPLQLPREKKLTDY
FTIDVEPAGHSLVNIYFQIDDFLLLTLNSLSVYKDPIRKYMFLRLNKDQSKHAINAAFNVF
SYRLRNIGVGPLGPDIRSSGP

FIG. 9B

MNSKHSYVELKDKVIVPGWPTLMLEIGFVGGTSRNQFLNIPFLSVKEPLQLPREKKLTDY
FTIDVEPAGHSLVNIYFQIDDFLLLTLNSLSVYKDPIRKYMFLRLNKDQSKHAINAAFNVF
SYRLRNIGVGPLGPDIRSSGP

FIG. 9C

MQPSMSFLIGFGTLVLVLSARTFDLQGLSCNTDSTPGLIDLEIRRLCHTPTENVISCEVSYL
NHTTISLPAVHTSCLKYHCKTYWGFFGSYSADRIINRYTGTVKGCLNNSAPEDPFECNW
FYCCSAITTEICRCSITNVTVAVQTFPPFMYCSFADCSTVSQQELESGKAMLSDGSTLTYT
PYILQSEVVNKTLNGTILCNSSSKIVSFDEFRRSYSLTNGSYQSSSINVTCANYTSSCRPRL
KRRRRDTQQIEYLVHKLRPTLKDAWEDCEILQSLLLGVFGTGIASASQFLRSWLNHPDII
GYIVNGVGVVWQCHRVNVTFMTWNESTYYPPVDYNGRKYFLNDEGRLQTNTPEARPG
LKRVMWFGRYFLGTVGSGVKPRRIRYNKTSHDYHLEEFEASLNMTPQTSITSGHETDPI
NHAYGTQADLLPYTRSSNITSTDTGSGWVHIGLPSFAFLNPLGWLRDLLAWAAWLGGV
LYLISLCVSLPASFARRRRLGRLQE

FIG. 10A

MQPSMSFLIGFGTLVLVLSARTFDLQGLSCNTDSTPGLIDLEIRRLCHTPTENVISCEVSYL
NHTTISLPAVHTSCLKYHCKTYWGFFGSYSADRIINRYTGTVKGCLNNSAPEDPFECNW
FYCCSAITTEICRCSITNVTVAVQTFPPFMYCSFADCSTVSQQELESGKAMLSDGSTLTYT
PYILQSEVVNKTLNGTILCNSSSKIVSFDEFRRSYSLTNGSYQSSSINVTCANYTSSCRPRL
KRRRRDTQQIEYLVHKLRPTLKDAWEDCEILQSLLLGVFGTGIASASQFLRSWLNHPDII
GYIVNGVGVVWQCHRVNVTFMTWNESTYYPPVDYNGRKYFLNDEGRLQTNTPEARPG
LKRVMWFGRYFLGTVGSGVKPRRIRYNKTSHDYHLEEFEASLNMTPQTSIASGHETDPI
NHAYGTQADLLPYTRSSNITSTDTGSGWVHIGLPSFAFLNPLGWLRDLLAWAAWLGGV
LYLISLCVSLPASFARRRRLGRWQE

FIG. 10B

```
         10         20         30         40         50
1234567890 1234567890 1234567890 1234567890 1234567890
HIVTPSLVFL CLLIPGLHAA FVHGGVPRES YLSTPVTRGE QIVVKTAKFY     50
GEKTTQRDLT ELEISSIFSH CCSLLIGVVI GSSSKIKAGA EQIKKRFKIM    100
MAALNRPSHG ETATLLQMFN PHEAIDWING QFWGSFVLP LLITDFESPG    150
KEFMDQIKLV ASYAQMTYT TIKEYLAECM DATLTIPVV                189
```

FIG. IIA

```
         10         20         30         40         50
1234567890 1234567890 1234567890 1234567890 1234567890
HIVTPSLVFL CLLIPGLHAA FVHGGVPRES YLSTPITRGE QIVVKTAEFY     50
GEKTTQRDLT ELEISSIFSH CCSLLIGVVI GSSSKIKAEA EQIKKRFKIM    100
MAAVNRPSHG ETATLLQMFN PHEAIDWING QFWGSFVLS LLITDFESPG    150
KEFMDQIKLV ASYAQMTYT TIKEYLAECM DATLTIPVV                189
```

FIG. IIB

```
         10         20         30         40         50
1234567890 1234567890 1234567890 1234567890 1234567890
HIVTPSLVFL CLLIPGLHAA FVHGGVPRES YLSTPITRGE QIVVKTAKFY     50
GEKTTQRDLT ELEISSIFSH CCSLLIGVVI GSSSKIKAGA EQIKKRFKIM    100
MAALNRPSHG ETATLLQMFN PHEAIDWING QFWGSFVLS LLITDFESPG    150
KEFMDQIKLV ASYAQMTYT TIKEYLAECM DATLTIPVV                189
```

FIG. IIC

|  | 10 | 20 | 30 | 40 | 50 |  |
|---|---|---|---|---|---|---|
|  | 1234567890 | 1234567890 | 1234567890 | 1234567890 | 1234567890 |  |
|  | TMSSTALTHL | LNRLSHTTTK | GDSFVINLDY | SSWCNGFRPE | LQAPICRQLD | 50 |
|  | QMFNCGYFFR | TGCTLPCFTT | FIIQDRFNPP | YSLSGEPVED | GVTCAVGTKT | 100 |
|  | MGEGMRQKLW | TILTSCWEII | ALREINVTFN | ILGQGDNQTI | IIHKSASQNN | 150 |
|  | QLLAERALGA | LYKHARLAGH | NLKVEECWVS | DCLYEYGKKL | FFRGVPVPGC | 200 |
|  | LKQLSRVTDS | TGELFPNLYS | KLACLTSSC |  |  | 229 |

FIG. 12

METHODS AND COMPOSITIONS FOR SCREENING OF HUMAN BORNA DISEASE VIRUS

GOVERNMENT SUPPORT

This invention was made with the support of the United States Government and the United States Government has certain rights in the invention pursuant to the United States Public Health Service Contract NS-12428.

TECHNICAL FIELD

The present invention relates generally to the Borna disease virus (BDV) or BDV-like viruses and specifically to compositions and methods useful for diagnosing BDV infection, especially in patients with neuropsychiatric disorders. More particularly, the invention relates to human BDV-derived virus sequences and antigens including peptides and recombinant BDV fusion proteins, anti-BDV antigen antibodies and oligonucleotide primers and use thereof in cellular- and molecular-based diagnostic methods.

BACKGROUND OF THE INVENTION

Evidence indicates that in addition to a genetic contribution, environmental determinants also play a role in the etiology of psychiatric disorders including schizophrenia and depression (Morozov, "Advances in Biological Psychiatry, 12, eds., S. Mendlewicz and H. Praag, Karger, New York (1983)). The hypothesis of a viral contribution is suggested by the realization that viruses can induce progressive neurological disorders associated with diverse pathological findings (Morozov, ibid., (1983); Kurstak et al., "Viruses, Immunity, and Mental Disorders", Plenum, New York (1987); ter Meulen, "Seminars in Neuroscience, 3 (1991)).

Borna disease virus (BDV) is a nonsegmented, negative-stranded (NNS) RNA virus (Briese et al., Proc. Natl. Acad. Sci., USA, 91:4362–4366 (1994); Cubitt et al., J. Virol., 68:1382–1396 (1994); de la Torre, J. Virol., 68:7669–7675 (1994); and Schneemann et al., Virol., 210:1–8 (1995)) with a nuclear site for the replication and transcription of its genome (de la Torre, supra, (1994); Schneemann et al., supra, (1995); and Cubitt et al., J. Virol., 68:1371–1381 (1994)) and the use of RNA splicing for its gene expression regulation (Cubitt et al., Virus Res., 34:69–79 (1994) and Schneider et al., J. Virol., 68:5007–5012 (1994)). These features signal BDV as the prototype of a new group of animal viruses (de la Torre, supra, (1994) and Schneemann et al., supra, (1995)).

Borna disease virus (BDV) is a noncytolytic neurotropic virus that infects a wide range of vertebrate species from birds and rodents to primates. It has a variable period of incubation and diverse pathological manifestations depending on the species, immune status and age of the host, as well as route of infection and virus strain (Ludwig et al., Prog. Med. Virol., 35:107–151 (1988); Lipkin et al., Microbial Pathogenesis, 13:167–170 (1992); Richt et al., Clin. Infect. Dis., 14:1240–1250 (1992); Koprowski et al., Curr. Topics Microbiol. Immunol., 190 (1995)).

Thus, BDV causes CNS disease in several non-human vertebrate species that is manifested by behavioral abnormalities and diverse pathologies depending on the species, age and immune status of the host, as well as route of infection and virus strain (Rott et al., in "Borna Disease", eds., H. Koprowski and I. Lipkin, Springer-Verlag, Berlin, pp17–30 (1995)). For example, heightened viral expression in limbic system structures, together with astrocytosis and neuronal degeneration within the hippocampal formation, constitute the main histopathological hallmarks of BDV infection in different animal species (Gosztonji et al., in "Borna Disease", eds., H. Koprowski and I. Lipkin, Springer-Verlag, Berlin, pp39–73 (1995) and Carbone et al., J. Virol., 65:6154–6164 (1991).

In the recently published International Application WO 96/21020, rat-derived BDV viral sequences were described for encoding rat BDV polypeptide sequences corresponding to p40, p23,gp18, p57, and BDV polymerase sequences. In addition, the application presents diagnostic and therapeutic methods for treating nervous system diseases based on the use of the rat-derived nucleic acids and encoded polypeptides. However, no human-specific sequences were identified by the authors.

The reproducible and clinically definable behavioral abnormalities accompanying BDV infection of rats and non-human primates have led to the speculation that BDV could cause similar CNS dysfunctions in humans. In support of this hypothesis are the results from cross-sectional seroepidemiological studies showing an increased prevalence of antibodies that recognize BDV-specific antigens in subjects with neuropsychiatric disorders compared to the normal healthy population (Rott et al., Science, 228:755–756 (1985); Bode et al., Lancet, ii:689 (1988); VandeWoude et al., Science, 250:1278–1281 (1990); Rott et al., Arch. Virol., 118:143–149 (1991); Bode et al., J. Med. Virol., 36:309–315 (1992); Fu et al., J. Affect. Disor., 27:61–68 (1993), for review see Bode, Curr. Top. Microbiol. Immunol., 190:101–128 (1995)). Moreover, prospective studies on acute psychiatric patients have shown a high percentage of BDV seropositives among patients with major depression (Bode et al., Arch. Virol. (Suppl), 7:159–167 (1993); Bode et al., Lancet, 343:297–298 (1994); and Bode et al., Nature Med., 1:232–236 (1995)).

Recently, using flow cytometry (FCM), BDV-specific antigens have been detected in peripheral blood monocytes (PBMC) from psychiatric patients (Bode et al., supra, (1994)). In addition, the present inventors with others have detected BDV-specific RNA sequences in such PBMC (Bode et al., supra, (1995) and Kishi et al., FEBS Letters, 364:293–297 (1995)). These findings led the present inventors to investigate the possibility of isolating infectious BDV from BDV-antigen positive human PBMC.

The present invention describes the isolation and sequence characterization of human BDV. Studies using coded PBMC samples from psychiatric patients and healthy control subjects for co-cultivation with a human oligodendroglia cell line (OL cells), led to the isolation of BDV from three hospitalized psychiatric patients, but not from any of the control subjects. The isolated virus was unequivocally identified as BDV based on the sequence identification of BDV open reading frames(ORFs) p24, p16, p56, and the putative catalytic domain of the BDV L polymerase. The sequence analysis obtained with the methods and compositions of this invention indicate that BDV human isolates are genetically very closely related to BDV from naturally infected animals of different species. These results further indicate that BDV could be one of the environmental factors contributing to the pathophysiology of neuropsychiatric disorders whose etiology remains elusive.

The present invention describes the detection of novel BDV antigen and RNA in the CNS of patients who presented with a history of mental disorders. BDV-specific antigen and RNA was also determined for the first time for the p16, p56 and L polymerase BDV-encoded polypeptides.

Thus, the present invention now unequivocally identifies the presence of infectious BDV in humans and its association with clinical profiles of mental disorders whose etiology remains unknown.

BRIEF SUMMARY OF THE INVENTION

The present invention therefore relates to methods, diagnostic systems and compositions useful for detecting human BDV or human BDV-like viral infection in a subject.

Compositions for use in the present invention include human BDV nucleic acids, vectors containing the nucleic acids, cells containing the vectors, human BDV polypeptides encoded by the nucleic acids or derived from a partial amino acid sequence therefrom, and anti-BDV polypeptide antibodies.

Preferred BDV nucleic acids encode a human BDV p24 polypeptide comprising an amino acid residue sequence in SEQ ID NOs 20, 21, 22, 32 and 33. Preferred p24 encoding nucleic acids have the nucleotide sequence in SEQ ID NOs 3, 4 and 5.

Other preferred BDV nucleic acids encode a human p16 polypeptide comprising an amino acid residue sequence in SEQ ID NOs 23, 24, 25, 34 and 35.

Preferred p16 encoding nucleic acids have the nucleotide sequence in SEQ ID NOs 7, 8 and 9.

Still other preferred BDV nucleic acids encode a human p56 polypeptide comprising an amino acid residue sequence in SEQ ID NOs 26, 27, 36, 37 and SEQ ID NO 38. Preferred p56 encoding nucleic acids have the nucleotide sequence in SEQ ID NOs 11 and 12.

Further preferred BDV nucleic acids encode a human BDV p40 polypeptide with the amino acid residue sequence in SEQ ID NOs 28, 29, 30, 39, 40 and 41. Preferred p40 encoding nucleic have the nucleotide sequence in SEQ ID NOs 14, 15 and 16.

Other preferred BDV nucleic acids encode a human BDV catalytic domain polypeptide of L polymerase protein with the amino acid residue sequence in SEQ ID such as glutaraldehyde, Klipstein, et al., *J. Infect. NO* 31. Preferred catalytic domain encoding nucleic acids have the nucleotide sequence in SEQ ID NOs 18 and 19.

Expression vectors containing the above identified BDV nucleic acids are also contemplated and in preferred aspects, the BDV nucleic acid is operably linked to a promoter. Cells transformed with the above identified expression vectors are contemplated.

The preferred BDV p24, p16, p56, p40 and catalytic domain polypeptides are identified above where the polypeptides are either synthetic or recombinant. Fusion proteins are also contemplated.

Antibodies that immunoreact with human BDV and the human BDV polypeptides of this invention are further contemplated.

Methods for use in the present invention include nucleic acid based as well as protein based methods for respectively detecting BDV nucleic acids and proteins. For the former, the method involves hybridizing a nucleic acid in a sample with a BDV nucleic acid of this invention. In preferred embodiments, the sample is a BDV-infectable cell, preferably a peripheral blood mononuclear cell. The sample is preferably isolated from a human and is useful for diagnosing BDV infection. In preferred embodiments, the method is useful to diagnose infection in a subject having a neuropsychiatric disorder.

Protein based methods include detection of a BDV ligand in a sample by contacting the sample with a human BDV polypeptide described above to allow formation of an immunoreaction complex followed by detection thereof. Preferred BDV ligands are antibodies. In preferred aspects, detection is accomplished with the addition of a detecting antibody that binds to the immunoreaction complex or by the indirect immunofluorescence focus assay. Detecting antibodies may also be labeled. In other preferred aspects, the polypeptide is immobilized on a solid support. Samples include a body fluid, preferably serum. The method is particularly useful for diagnosing BDV infection in a human.

The method according to claim 66 wherein the sample is isolated from a human having a neuropsychiatric disorder.

Other preferred methods include detecting a BDV antigen in a sample by contacting the sample with an anti-human BDV antibody as described above thereby forming an immunoreaction complex followed by detection thereof. In preferred aspects, the sample comprises cells, most preferably peripheral blood mononuclear cells. Detection can be accomplished by flow cytometry, ELISA, or by immunoblot analysis.

The present invention also contemplates kits for detecting the presence of BDV nucleic acid, BDV ligands or BDV antigens as described above.

BRIEF DESCRIPTION OF THE DRAWINGS

FIGS. 2A–2M illustrate the continuous cDNA nucleotide sequence alignment of the BDV strains described by de la Torre, *J. Virol.,* 68:7669–7675 (1994) indicated as BDV JCT and by Briese et al., *Proc. Natl. Acad. Sci. USA,* 91:4382–4386 (1994) indicated as BDV Briese. Dots indicate the same nucleotide sequence as that found in the same position in the consensus sequence. Nucleotide substitutions for each strain are indicated above the consensus sequence. At those positions, the consensus sequence presents the possible substitutions according to the convention adopted by the IUPAC-IUB Biochemical Nomenclature Commission. The consensus sequence is also listed as SEQ ID NO 1.

FIGS. 3A and 3B together form a composite of the autoradiographic segment showing the results of southern blot hybridization and the part of the gel showing the ethidium bromide staining of GAPDH amplified fragment. Track M corresponds to the 1 kb ladder DNA. The top and bottom parts of the composite were lined up with respect to the migration of the 1 kb ladder DNA (track M).

FIGS. 4A, 4B and 4C separately illustrate the respective nucleotide sequence alignment of open reading frames (ORFs) p24 (4A), p16 (4B) and p56 (4C) among the human BDV isolates (H1, H2, and H3), C6BV and BDV strain V. Dots indicate the same nucleotide as the one found for that position in the BDV strain V sequence. Numbers on the right correspond to last nucleotide position of each row within the corresponding ORF. In FIG. 4A, the nucleotide sequence for Strain V is listed as SEQ ID NO 2 while the nucleotide sequences for p24 for each of patients H1, H2 and H3 are respectively listed as SEQ ID NOs 3, 4 and 5. In FIG. 4B, the nucleotide sequence for Strain V is listed as SEQ ID NO 6 while the nucleotide sequences for p16 for each of patients H1, H2 and H3 are respectively listed as SEQ ID NOs 7, 8 and 9. In FIG. 4C, the nucleotide sequence for Strain V is listed as SEQ ID NO 10 while the nucleotide sequence for p56 for patient H1 is listed as SEQ ID NO 11. Since the nucleotide sequences for patients H2 and H3 are identical, that sequence is listed as SEQ ID NO 12.

FIGS. 5A-1 and 5A-2 illustrate the nucleotide sequence alignment of the p40 open reading frame (ORF) among the human BDV isolates (H1, H2, and H3), C6BV and BDV strain V along with a derived consensus sequence written using the IUPAC code. Dots indicate the same nucleotide as the one found for that position in the consensus sequence (SEQ ID NO 13). Numbers on the right correspond to last nucleotide position of each row within the corresponding ORF. In FIGS. 5A-1 and 5A-2, the nucleotide sequences for each of patients H1, H2 and H3 are respectively listed as SEQ ID NOs 14, 15 and 16.

FIGS. 5B-1, 5B-2 and 5B-3 illustrate the nucleotide sequence alignment of the open reading frames (ORF) of the catalytic domain of L polymerase, labeled on the figures as p180, among the human BDV isolates (H1, H2, and H3), C6BV (labeled as p180frag) and BDV strain V (5) along with a derived consensus sequence written using the IUPAC code (SEQ ID NO 17). Dots indicate the same nucleotide as the one found for that position in the consensus sequence. Numbers on the right correspond to last nucleotide position of each row within the corresponding ORF. Since the nucleotide sequences for patients H1 and H2 are identical, that sequence is listed as SEQ ID NO 18 while that for patient H3 is listed as SEQ ID NO 19.

FIG. 6A shows the amino acid differences found in ORFs p24, p16 and p56 among the human BDV isolates (H1, H2, and H3), C6BV and strain V. Amino acids are presented in the single letter code. Numbers on top correspond to the codon position within each ORF. FIG. 6B is a triangular matrix summarizing the total number of nucleotide (upper right) and amino acid (lower left) substitutions among human BDV isolates (H1, H2, and H3), C6BV and strain V.

FIGS. 8A, 8B and 8C respectively show the p24 amino acid residue sequences, also listed as SEQ ID NOs 20, 21 and 22, derived from patient nucleotide sequences H1, H2 and H3 listed in SEQ ID NOs 3, 4 and 5 as described in the legend for FIG. 4A.

FIGS. 9A, 9B and 9C respectively show the p16 amino acid residue sequences, also listed as SEQ ID NOs 23, 24 and 25, derived from patient nucleotide sequences H1, H2 and H3 listed in SEQ ID NOs 7, 8 and 9 as described in the legend for FIG. 4B.

FIGS. 10A and 10B respectively show the p56 amino acid residue sequences, also listed as SEQ ID NOs 26 and 27, derived from patient nucleotide sequences H1 listed as SEQ ID NO 11 and H2/H3 (identical) listed in SEQ ID NO 12 as described in the legend for FIG. 4C.

FIGS. 11A, 11B and 11C respectively show the p40 amino acid residue sequences, also listed as SEQ ID NOs 28, 29 and 30, derived from patient nucleotide sequences H1, H2 and H3 listed in SEQ ID NOs 14, 15 and 16 as described in the legend for FIG. 5A.

FIG. 12 shows the amino acid residue sequence of the catalytic domain of the L polymerase, also listed as SEQ ID NO 31, derived from patient nucleotide sequences H1/H2 (identical) and H3 respectively listed in SEQ ID NOs 18 and 19 as described in the legend for FIG. 5B.

DETAILED DESCRIPTION OF THE INVENTION

A. Definitions

TABLE OF CORRESPONDENCE

Figure 1:
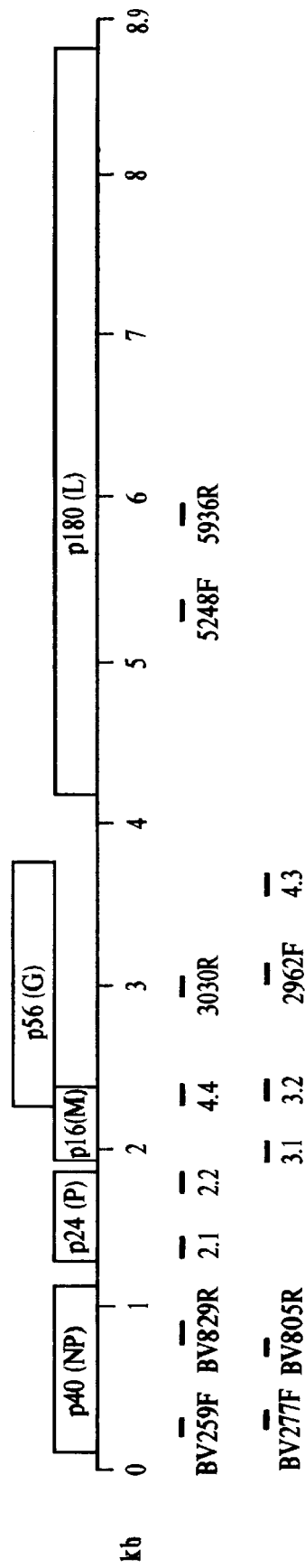
FIG. 1 is a schematic diagram of the BDV genome RNA (anti-genomic polarity) and location of primers used in amplifying the genome encoding BDV p40, p24, p16, p56 and a portion of the L polymerase polypeptides. The genome organization presented in the diagram is based on the complete sequence of two non-human BDV RNA genomes as yet reported, strain v and C6BV (Briese et al., *Proc. Natl. Acad. Sci, USA,* 91:4382–4386 (1994); Cubitt et al., *J. Virol.,* 68:1382–1396 (1994); and de la Torre, *J. Virol.,* 68:7669–7675 (1994)). Accession numbers for strain V and C6BV RNA genome sequences are U04608 and L27077, respectively. Sequence, polarity, and nucleotide positions covered by the primers are summarized in Table 1 and Table 2.

| Code Group | Nucleotide(s) | |
|---|---|---|
| A | A | adenine |
| C | C | cytosine |
| G | G | guanine |
| T | T | thymine (in DNA) |
| U | U | uracil (in RNA) |
| Y | C or T(U) | pyrimidine |
| R | A or G | purine |
| M | A or C | amino |
| K | G or T(U) | keto |
| S | G or C | strong interaction (3 hydrogen bonds) |
| W | A or T(U) | weak interaction (2 hydrogen bonds) |
| H | A or C or T(U) | not-G |
| B | G or T(U) or C | not-A |
| V | G or C or A | not-T or not-U |
| D | G or A or T(U) | not-C |
| N | G,A,C or T(U) | any |

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a sequence whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded. When referring to nucleic acids, the term "substantial identity" indicates that the sequences of two nucleic acids, or designated portions thereof, when optimally aligned and compared, are identical, with appropriate nucleotide insertions or deletions, in at least about 80% of the nucleotides, usually at least 90% to 95%, and more preferably at least about 98% to 99.5% of the nucleotides. Alternatively, substantial nucleic acid indentity exists when a nucleic acid segment will hybridize under selective hybridization conditions, to a complement of another nucleic acid strand.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for a polypeptide. The primary information can either be RNA or DNA.

Duplex DNA: A double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently or substantially complementary to that on another single strand to specifically and selectively hybridize to it with consequent hydrogen bonding. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%.

Hybridization: The pairing of substantially complementary nucleotide sequences (strands of nucleic acid) to form a duplex or heteroduplex by the establishment of hydrogen bonds between complementary base pairs. It is a specific, i.e., non-random, interaction between two complementary polynucleotides that can be competitively inhibited.

Isolated or Substantially Purified: With nucleic acids, the terms refer to those that have been purified away from other cellular components or other contaminants, e.g., other cellular nucleic acids or proteins, by standard techniques, including alkaline/SDS treatment, CsCl banding, column chromatography, and others well known in the art.

Nucleotide Analog: A purine or pyrimidine nucleotide that differs structurally from A, T, G, C, or U, but is sufficiently similar to substitute for the normal nucleotide in a nucleic acid molecule.

Upstream: In the direction opposite to the direction of DNA transcription, and therefore going from 5' to 3' on the noncoding strand, or 3' to 5' on the RNA transcript.

Downstream: Further along a DNA sequence in the direction of sequence transcription or read out, that is, traveling in a 3' to 5'-direction along the noncoding strand of the DNA or 5'- to 3'-direction along the RNA transcript.

Stop Codon: Any of three codons that do not code for an amino acid, but instead cause termination of protein synthesis. They are UAG, UAA and UGA and are also referred to as a nonsense, termination, or translational stop codon.

Reading Frame: Particular sequence of contiguous nucleotide triplets (codons) employed in translation. The reading frame depends on the location of the translation initiation codon.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COCH refers to the free carboxy group present at the carboxy terminus of a polypeptide. In keeping with standard polypeptide nomenclature (described in *J. Biol. Chem.,* 243:3552–59 (1969) and adopted at 37 CFR §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: A linear series of amino acid residues connected to one another by peptide bonds between the alpha-amino group and carboxy group of contiguous amino acid residues.

Protein: A linear series of greater than 50 amino acid residues connected one to the other as in a polypeptide.

Substantially Purified or Isolated: When used in the context of polypeptides or proteins, the terms describe those molecules that have been separated from components that naturally accompany them. Typically, a monomeric protein is substantially pure when at least about 60% to 75% of a sample exhibits a single polypeptide backbone. Minor variants or chemical modifications typically share the same polypeptide sequence. A substantially purified protein will typically comprise over about 85% to 90% of a protein sample, more usually about 95%, and preferably will be over about 99% pure. Protein or polypeptide purity or homogeneity may be indicated by a number of means well known in the art, such as polyacrylamide gel electrophoresis of a sample, followed by visualization thereof by staining. For certain purposes, high resolution is needed and high performance liquid chromatography (HPLC) or a similar means for purification utilized.

Synthetic Peptide: A chemically produced chain of amino acid residues linked together by peptide bonds that is free of naturally occurring proteins and fragments thereof.

B. BDV and Infection in Humans

Borna disease virus (hereinafter referred to as BDV) is a noncytolytic neurotropic virus that has been shown to infect a wide range of vertebrate species from birds and rodents to primates. BDV is a nonsegmented, negative-stranded (NNS) RNA enveloped virus, that, as described in the Background, is the prototype of a new group of animal RNA viruses. As used herein, the term "BDV" is used in conjunction with viral particles, nucleic acids, polypeptides and antibodies.

In addition to a genetic contribution, environmental determinants including viral infection play a role in the etiology of psychiatric disorders including schizophrenia and depression. Recent evidence shows that patients with psychiatric disorders contain protein and nucleic acid markers of the presence of BDV. Specifically, the p24 and p38/40 BDV-specific antigens (Bode et al., *Lancet*, 343:297–298 (1994) and corresponding RNA sequences (Bode et al., *Nature Med.*, 1:232–236 (1995) and Kishi et al., *FEBS Letters*, 364:293–297 (1995) have been detected in $CD14^+$ peripheral blood monocytes (PBM) subset within peripheral blood mononuclear cells (PBMC) from patients with psychiatric disorders.

However, the isolation of infectious BDV from BDV antigen-positive PBMC was not accomplished prior to the present invention. In addition, this invention presents the first documentation of BDV RNA in a human that encodes full length 24 polypeptide (p24) as well as p16 and p56 polypeptides. Furthermore, the presence of a catalytically active portion of the BDV L polymerase has now been documented in human patients.

Thus, for the first time, the isolation and sequence characterization of human BDV is now described. As described in the Examples, from coded PBMC samples from psychiatric patients and healthy control subjects for co-cultivation with a human oligodendroglia cell line (OL cells), BDV was isolated from three hospitalized psychiatric patients, but not from any of the control subjects. The isolated virus was unequivocally identified as BDV based on the sequence identification of BDV open reading frames (ORFs) p24, p16, p56, and the putative catalytic domain of the BDV L polymerase. Furthermore, the identification of infectious human BDV was confirmed by the infection of a human oligodendroglial cell line following co-cultivation with BDV-positive patient PBMC as described in the Examples. Therefore, the viral isolates have been unequivocally identified as infectious human BDV.

The present invention thus contemplates an isolated infectious human BDV. A human BDV isolate is a nonsegmented, negative-stranded (NNS) RNA enveloped virus that is present in humans, specifically in cells or body fluids of a human as discussed below. The human BDV particle is characterized by containing an RNA genome also referred to as genomic viral nucleic acid. BDV isolated from different subjects suspected of having BDV, although related, may display differences in nucleotide sequence that may or may not result in encoded amino acid differences in the translated BDV polypeptides.

Thus, a BDV genomic viral nucleic acid within a BDV isolate is specific for the subject from which it is obtained. In other words, the BDV nucleic acid is said to be "derived from" a specific BDV-infected cell obtained from a particular subject. In particular, as described in Section C below, the BDV nucleic acid sequences derived from three BDV-infected patients exhibited nucleotide substitutions at various positions within the genome thereby rendering each sequence unique. However, some polypeptide-encoding regions of the genome from the three patients were identical. As discussed later, for the regions that did reveal nucleotide substitutions, some of them resulted in changes in the deduced amino acid sequence of various BDV polypeptides.

As used herein, the terms "isolated", "substantially isolated", "substantially purified" and "substantially homogenous" are used interchangeably and describe a molecule that has been separated from components that naturally accompany it. When referring to a BDV isolate, "isolated" refers to those BDV isolates that have been purified away from other cellular or fluid components, e.g., other cellular nucleic acids, including other viruses, or proteins found within cells or in a body fluid sample. Thus, a human BDV isolate represents BDV particles that have been separated from cellular components or fluids in which the particle resides. Exemplary techniques for isolating BDV particles of this invention are well known in the art.

A BDV particle-containing cell is also referred to as a BDV-infected cell or a BDV-containing cell. In other words, a BDV-containing cell of this invention is a cell that is infected with a human BDV particle as defined herein. With respect to BDV particles within cells, one aspect of the present invention includes isolation of BDV particles from cells derived directly from a person. Such cells are obtained from a person suspected of having BDV. A preferred BDV-infected cell in a subject is a peripheral blood mononuclear cell also referred to as PBMC from which BDV is isolatable. Such cells are obtained by standard techniques, e.g., purification from a blood sample, leukophoresis, and others well known in the art.

Another aspect of the present invention includes isolation of BDV particles from cultured cells that have been infected with BDV by co-cultivation or exposure to BDV-infected cells derived from a BDV-infected person. A preferred BDV-infectable cell line is a human oligodendroglial cell line. Other BDV-infectable cell lines contemplated for use in isolating patient-specific BDV include human neuroblastoma cell lines.

In view of the ability to isolate BDV from BDV-infected PBMC following co-cultivation with uninfected oligodendroglial cells, the isolated virus is said to be infectious, i.e., have the ability to infect and multiply in susceptible cells.

Thus, the term "infectious" describes a process whereby BDV is capable of being spread from one cell to another, with or without direct contact. The process can therefore occur both in vivo and in vitro. As a result, BDV is said to invade and become established in or on the recipient or infected cell. Such infection may be active whereby the BDV multiplies within the cell. This process may result in the state of local or systemic disease with cellular or systemic injury if the cell is within an organism. Alternatively, the infectious BDV may be present at very low levels in the infected subject and, in this case BDV may not be recovered from such a subject although its continued presence can be inferred from continuing immunologic reactivity, or retrospectively, from the later emergence of overt illness.

In another aspect of the present invention, BDV is isolated from a sample taken from a subject suspected of having BDV. As used herein, a "sample", also referred to as a body sample or a fluid sample, is any sample that can be removed from a subject and in which BDV resides. Exemplary samples include serum and PBMC. Methods of collecting such samples are well known in the medical arts, such as withdrawal of blood samples by venipuncture.

The human BDV particles of this invention are found in subjects who have been diagnosed and characterized as having psychiatric disorders as described in the Examples. Based on the present discoveries, BDV has been found in patients diagnosed with acute bipolar disorders with or without psychotic features and in patients diagnosed with chronic obsessive compulsive disorder. Thus, patients exhibiting behavioral characteristics known to be associated with these psychiatric profiles are potential candidates for screening for BDV infection and isolating BDV therefrom. The phrase "suspected of having BDV" describes subjects who are characterized by having the above-described psychiatric profiles as well as the characteristics of other neuropsychiatric disorders including schizophrenia.

Thus, isolation of infectious human BDV particles in psychiatric patients has provided support for a viral-mediated etiology of some forms of neurological dysfunction.

C. Human BDV Nucleic Acids

The nucleic acids of the present invention are BDV nucleic acids that are isolatable from a human. As such, BDV nucleic acids include complete genomic RNA nucleic acid sequences, DNA sequences complementary to BDV genomic RNA sequences, RNA and the corresponding cDNA sequence regions that encode BDV polypeptides, complementary sequences thereto, and fragments thereof, such as shorter polynucleotide sequences useful for hybridization aspects of this invention. The term "BDV nucleic acid" thus includes RNA genomic and cDNA sequences of the BDV genome. The nucleic acids of this invention further include sequences having other nucleotides known in the art such as nucleotide analogs.

The nucleic acids of this invention may be present in infected cells, in an infected or transfected cell lysate, in body fluid samples, in partially purified form, or in substantially pure form. As an alternative from isolating BDV nucleic acids from natural sources as described herein, BDV nucleic acids may be synthetic molecules. The nucleic acid can be in the form of nucleic acids described above, such as genomic RNA or cDNA, and in single or double stranded form, respectively. The terms "nucleic acid" and "polynucleotide" been previously defined in Section A.

Nucleic acids that correspond to the entire BDV viral genome or portions thereof, that are able to cause BDV infection when transfected into susceptible cells, or that code for the claimed BDV polypeptides or portions thereof, will normally be from at least 10 to thousands of nucleotide base pairs in length. One or more introns may be present in the genome including the protein-coding nucleic acid sequences. The length of nucleic acid sequences will vary depending on the use. In view of the degeneracy of the genetic code for encoding amino acids, different nucleotide sequences including encoding triplet codons are contemplated in this invention that encode substantially the same or functionally the equivalent amino acid sequence of the BDV polypeptides as described herein and below.

BDV nucleic acids contain open reading frames (ORF) that encode BDV polypeptides, and fragments thereof, include those that encode all or part of the BDV polypeptides designated p24, p16, p56, p40 and the L polymerase, preferably the catalytic domain. The polypeptides are more fully described in Section D.

Thus, a preferred nucleic acid encodes a human BDV p24 polypeptide having an amino acid residue sequence as listed in SEQ ID NO 20, SEQ ID NO 21, SEQ ID NO 22, MATGPSSLVDSLEDEEDP (SEQ ID NO 32) and RIYPQLPSAPTADEWDIIP (SEQ ID NO 33). Similarly, a preferred nucleic acid encodes a human BDV p16 polypeptide having an amino acid residue sequence as listed in SEQ ID NO 23, SEQ ID NO 24, SEQ ID NO 25, MNSKH-SYVELKGKVIVPG (SEQ ID NO 34) and RLRNIGVG-PLGPDIRSSGP (SEQ ID NO 35). Another preferred nucleic acid encodes a human BDV p56 polypeptide having an amino acid residue sequence as listed in SEQ ID NO 26, SEQ ID NO 27, GLSCNTDSTPGLIDLEIR (SEQ ID NO 36), RSKLRRRRRDTQQIEYLV (SEQ ID NO 37) and LISLCVSLPASFARRRRLGRWQE (SEQ ID NO 38). A further preferred nucleic acid encodes a human BDV p40 polypeptide having an amino acid residue sequence as listed in SEQ ID NO 28, SEQ ID NO 29, SEQ ID NO 30, MPPKRRLVDDADAMEDQD (SEQ ID NO 39), MEDQD-DLYEPPSSLPKLP (SEQ ID NO 40) and ELSGEISAIMR-MIGLTGLN (SEQ ID NO 41). A further preferred nucleic acid encodes a human BDV catalytic domain polypeptide from L polymerase having an amino acid residue sequence as listed in SEQ ID NO 31.

While all nucleic acid sequences are contemplated for encoding the BDV polypeptides as described above based on the degeneracy of the genetic code, particularly preferred p24 BDV-polypeptide encoding nucleic acid sequences are those listed in SEQ ID NO 3, SEQ ID NO 4 and SEQ ID NO 5. Similarly, particular p16 BDV-polypeptide encoding nucleic acid sequences are those listed in SEQ ID NO 7, SEQ ID NO 8 and SEQ ID NO 9. Particular p56 BDV-polypeptide encoding nucleic acid sequences are those listed in SEQ ID NO 11 and SEQ ID NO 12. BDV p40 polypeptide encoding nucleic acid sequences are listed in SEQ ID NO 14, SEQ ID NO 15 and SEQ ID NO 16. BDV catalytic domain polypeptide encoding nucleic acid sequences are listed in SEQ ID NO 18 and SEQ ID NO 19.

Polynucleotide sequences derived from the above sequences are also contemplated in the present invention. Such sequences are useful as hybridization probes for the presence of BDV nucleic acids in physiological body samples including cells and body fluids as well as in laboratory samples such as in DNA libraries including genomic and cDNA libraries, tissue extracts, cell extracts, and in impure and purified samples and the like. Other sequences are useful as primers for use in PCR amplification of BDV sequences as more fully described in Section F1. For either aspect the polynucleotide sequences will usually be at least about 10 nucleotides in length and more usually 15 to 25 nucleotides in length.

These polynucleotide sequences may be synthetic DNA fragments prepared, for example, by the phosphoramidite method described by Beaucage et al., *Tetrahedron Letters*, 22:1859–1862 (1981), or by the triester method according to Matteucci et al., *J. Am. Chem. Soc.*, 103:3185 (1981), both incorporated herein by reference. See also, U.S. Pat. No. 4,356,270, U.S. Pat. No. 4,458,066, U.S. Pat. No. 4,416,988, U.S. Pat. No. 4,293,652. A double stranded fragment may then be obtained, if desired, by annealing the chemically synthesized single strands together under appropriate conditions or by synthesizing the complementary strand using DNA polymerase with an appropriate primer sequence.

A polynucleotide of this invention is substantially complementary to a target BDV nucleic acid when it will anneal only to a single desired position on that target nucleic acid under conditions as described in the Examples. Proper annealing conditions depend, for example, upon the polynucleotide's length, base composition, and the number of mismatches and their position on a polynucleotide, and must often be determined empirically.

The primer is capable of acting as a point of initiation of nucleic acid synthesis when placed under conditions in which synthesis of a primer extension product, complementary to a nucleic acid strand, is induced. Inducing conditions include the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide.

For review of probe and primer design and annealing conditions, see, for example, Sambrook et al., *Molecular Cloning: A Laboratory Manual*, (2nd ed.), Vols 1–3, Cold Spring Harbor Laboratory, (1989) or Ausebel et al., *Current Protocols in Molecular Biology*, Greene Publishing and Wiley-Interscience, New York ((1987), the references of which are hereby incorporated. Exemplary hybridization probes and primer pairs are described in Section F1 and in the Examples.

The BDV nucleic acids of this invention, including BDV polynucleotide sequences, as described herein are obtained by conventional nucleic acid procedures, including synthesis as described above, isolation, purification, PCR amplification and the like. Particularly preferred are procedures including those specified for use with the methods of this invention that involve PCR amplification of a provided BDV nucleic acid sample to produce an amplification product containing the nucleotide sequences as described herein.

In preferred embodiments, the nucleic acid sample is enriched for the presence of BDV nucleic acid. Enrichment is typically accomplished by first preparing cDNA from the genomic RNA as described in the Examples followed by PCR amplification employing a PCR primer pair as described herein. The preferred method for obtaining enriched BDV nucleic acid is reverse transcriptase-PCR (RT-PCR) although other equally useful amplification methods are well known in the art and are applicable with the methods of this invention.

Particularly preferred methods for producing a sample to be assayed use preselected polynucleotides as primers for use in PCR as described in Section F1.

Through the use of recombinant DNA techniques, the BDV nucleic acids described above are used in expression vector systems to produce recombinant BDV polypeptides of this invention. In addition, in an alternative approach, the BDV polypeptides are also obtained by directly synthesized, obtained by purification procedures from particular BDV-polypeptide containing sources, and the like as further described in Section D below.

Exemplary expression vector systems for producing recombinant expressed BDV polypeptides as described below include those that allow expression in prokaryotic and eukaryotic cells. Preferred cells include bacterial, yeast, insect and mammalian cells.

Vectors capable of directing the expression of genes or nucleic acid fragments thereof as well as preselected nucleotide sequences to which they are operably linked are referred to herein as "expression vectors" or "expression plasmids", both of which are also referred to as "plasmids".

As used herein, the term "vector" or "plasmid" refers to a nucleic acid molecule capable of transporting between different genetic environments another nucleic acid to which it has been operably linked. Thus, plasmids are also referred to as vectors. Preferred vectors are those capable of autonomous replication and expression of structural gene products present in the DNA segments to which they are operably linked. Vectors, therefore, preferably contain the replicons and selectable markers that are compatible with the host selection system.

One type of preferred vector is an episome, i.e., a nucleic acid capable of extra-chromosomal replication. Preferred vectors are those capable of autonomous replication and/or expression of nucleic acids to which they are linked.

A plasmid of this invention is a circular double-stranded plasmid that contains at least a regulation region having elements capable of activating transcription of the translatable BDV polypeptide-encoding nucleotide sequences of this invention. The plasmid further contains a translatable nucleotide sequence from which the desired BDV polypeptides are expressed.

Such expression vectors contain a promotor sequence in the regulatory region which facilitates the efficient transcription of an inserted genetic sequence in the host. The expression vector typically contains an origin of replication, a promoter, as well as specific genes which allow phenotypic selection of the transformed cells. The BDV DNA segment can be present in the vector operably linked to regulatory elements, for example, a promoter (e.g., T7, metallothionein I, or polyhedrin promoters).

In a separate embodiment, a useful, but not necessary element of an expression vector is one or more selectable or screenable markers. A selectable marker may be a gene that codes for a protein necessary for the survival or growth of a host cell transformed with the vector. The presence of this gene ensures the growth of only those host cells that contain the vector. Preferred prokaryotic and eukaryotic drug resistance genes respectively confer resistance to ampicillin or tetracyclin and to neomycin (G418 or Geneticin). Typical selection genes encode proteins that (a) confer resistance to antibiotics or other toxic substances, e.g., chloramphenicol, kanamycin, streptomycin, carbenicillin, mercury, rifampcin, rifampicin, fusaric acid, and the like; (b) complement auxotrophic deficiencies, or (c) supply critical nutrients not available from complex media, e.g., the gene encoding D-alanine racemase for Bacilli. The choice of the proper selectable marker depends on the host cell, and appropriate markers for different hosts are well known in the art.

A screenable marker is a gene that codes for a protein whose activity is easily detected, allowing cells expressing such a marker to be readily identified. Such markers include, for example, β-galactosidase, β-glucuronidase, and luciferase. These markers may be expressed in the form of a fusion protein with a recombinant BDV polypeptide of this invention as described further below.

The choice of vector to which the regulatory region and nucleotide sequences for encoding polypeptides of the present invention is operably linked depends directly, as is well known in the art, on the functional properties desired, e.g., replication or protein expression, and the host cell to be transformed, these being limitations inherent in the art of constructing recombinant DNA molecules.

The phrase "operably linked" refers to the covalent joining of nucleotide sequences, preferably by conventional phosphodiester bonds, into one strand of DNA, whether in single or double stranded form. Generally, operably linked means that the nucleic acid sequences being linked are contiguous and, where necessary to join two protein- or polypeptide-encoding regions, are contiguous and in proper reading frame.

Moreover, the joining of nucleotide sequences results in the joining of functional elements such as response elements in regulatory regions with promoters and downstream polypeptide-encoding nucleotide sequences as described herein.

One typical method for operably linking inserts into expression plasmids is by directional ligation. This is accomplished through a sequence of nucleotides that are adapted for directional ligation. Such a sequence is referred to commonly as a polylinker that is a region of a DNA expression vector that (1) operably links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette.

Techniques for nucleic acid manipulation, such as cloning of nucleic acid sequences encoding BDV polypeptides into expression vectors are described generally, for example, by Sambrook et al., supra, or Ausebel et al., supra, the references of which are hereby incorporated.

A variety of host-expression vector systems may be utilized to express a BDV polypeptide encoded by a nucleotide sequence of this invention. These include but are not limited to microorganisms such as bacteria transformed with recombinant bacteriophage DNA, plasmid DNA or cosmid DNA expression vectors containing a polypeptide-encoding nucleotide sequence; yeast transformed with recombinant yeast expression vectors containing a polypeptide-encoding nucleotide sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a polypeptide-encoding nucleotide sequence; insect cell systems infected with recombinant virus expression vectors (e.g., baculovirus) containing a polypeptide-encoding nucleotide sequence; or animal cell systems infected with recombinant virus expression vectors (e.g., retroviruses, adenovirus, vaccinia virus) containing a polypeptide-encoding nucleotide sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, and necessary processing information sites, such as ribosome-binding sites, RNA splice sites, polyadenylation sites, transcriptional terminator sequences and the like, may be used in the expression vector (see e.g., Bitter, et al., *Methods in Enzymology,* 153:516–544, (1987)). Control sequences are chosen so that the sequences are functional in the desired host cell. For the expression in eukaryotic cells, the enhancers or promoters may be those naturally associated with BDV genes, although it will be understood that in many cases others, including those derived from viruses such as SV40, adenovirus, bovine papilloma virus and the like, are equally appropriate.

For example, when cloning in bacterial systems, inducible promoters such as PI of bacteriophage λ, Plac, Ptrp, Ptac (Ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of a polypeptide-encoding nucleotide sequence.

In bacterial systems a number of expression vectors may be advantageously selected for expression of a polypeptide-encoding nucleotide sequence according to the methods of this invention. For example, when large quantities are to be produced, vectors which diorect the expression of high levels of fusion protein products that are readily purified may be desirable. Those which are engineered to contain a cleavage site to aid in recovering the protein are preferred. Such vectors include but are not limited to the *E. coli* expression vector pUR278 (Ruther, et al., *EMBO J.,* 2:1791, (1983)), in which a polypeptide-encoding nucleotide sequence of this invention may be ligated into the vector in frame with the lacZ coding region so that a hybrid polypeptide-lacZ protein is produced; pIN vectors (Inouye & Inouye, *Nuc. Acids Res.,* 13:3101–3109 (1985); Van Heeke & Schuster, *J. Biol. Chem.,* 264:5503–5509 (1989)); and the like.

In one embodiment, the vector utilized includes prokaryotic sequences that facilitate the propagation of the vector in bacteria, i.e., a DNA sequence having the ability to direct autonomous replication and maintenance of the recombinant DNA molecule extra-chromosomally when introduced into a bacterial host cell. Such replicons are well known in the art.

Those vectors that include a prokaryotic replicon also typically include convenient restriction sites for insertion of a recombinant DNA molecule of the present invention. Typical of such vector plasmids are pUC18, pUC19, pBR322, and pBR329 available from BioRad Laboratories, (Richmond, Calif.) and pPL available from Pharmacia, (Piscataway, N.J.), and pBLUESCRIPT and pBS available from Stratagene, (La Jolla, Calif.). A vector of the present invention may also be a Lambda phage vector including those Lambda vectors described in *Molecular Cloning: A Laboratory Manual*, Second Edition, Maniatis et al., eds., Cold Spring Harbor, N.Y. (1989).

In another preferred embodiment, plasmid vectors for use in the present invention are also compatible with eukaryotic cells. Eukaryotic cell expression vectors are well known in the art and are available from several commercial sources. Typically, such vectors provide convenient restriction sites for insertion of the desired recombinant DNA molecule, and further contain promoters for expression of the encoded genes which are capable of expression in the eukaryotic cell, as discussed earlier. Typical of such vectors are pSVO and pKSV-10 (Pharmacia), and pPVV-1/PML2d (International Biotechnology, Inc.), and pTDT1 (ATCC, No. 31255).

In addition, in eukaryotic plasmids, one or more transcription units are present that are expressed only in eukaryotic cells. The eukaryotic transcription unit consists of noncoding sequences and sequences encoding selectable markers. The expression vectors of this invention also contain distinct sequence elements that are required for accurate and efficient polyadenylation. In addition, splicing signals for generating mature mRNA are included in the vector. The eukaryotic plasmid expression vectors contain viral replicons, the presence of which provides for the increase in the level of expression of cloned genes. A preferred replication sequence is provided by the simian virus 40 or SV40 papovavirus.

A variety of yeast cultures and suitable expression vectors for transforming yeast cells are known for use in this invention. See, e.g., U.S. Pat. Nos. 4,745,057, 4,797,359, 4,615,974, 4,880,734, 4,711,844, and 4,865,989, the disclosures of which are hereby incorporated by reference.

An alternative expression system that can be used to express a protein of the invention is an insect system. In one such system, Autographa californica nuclear polyhedrosis virus (AcNPV) is used as a vector to express foreign genes. The virus grows in *Spodoptera frugiperda* cells. A BDV polypeptide-encoding nucleotide sequence may be cloned into non-essential regions (in *Spodoptera frugiperda* for example the polyhedrin gene) of the virus and placed under control of an AcNPV promoter (for example the polyhedrin promoter). Successful insertion of the polypeptide-encoding nucleotide sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. See Smith, et al., *J. Biol. Chem.,* 46:584 (1983); Smith, U.S. Pat. No. 4,215,051.

Mammalian cell systems that utilize recombinant viruses or viral elements to direct expression may be engineered. For example, when using adenovirus expression vectors, the coding sequence of a BDV polypeptide may be ligated to an adenovirus transcription/translation control complex, e.g., the late promoter and tripartite leader sequence. This chimeric gene may then be inserted into the adenovirus genome by in vitro or in vivo recombination. Insertion in a nonessential region of the viral genome (e.g., region E1 or E3) will result in a recombinant virus that is viable and capable of expressing the polypeptide in infected hosts (e.g., see Logan et al., *Proc. Natl. Acad. Sci., USA,* 81:3655–3659 (1984)). Alternatively, the vaccinia virus 7.5K promoter may be used, e.g., see, Mackett, et al., *Proc. Natl. Acad. Sci., USA,* 79:7415–7419 (1982); Mackett, et al., *J. Virol.,* 49:857–864 (1984); Panicali, et al., *Proc. Natl. Acad. Sci., USA,* 79:4927–4931 (1982)). Of particular interest are vectors based on bovine papilloma virus which have the ability to replicate as extrachromosomal elements (Sarver, et al., *Mol. Cell. Biol.,* 1:486 (1981)). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a BDV polypeptide-encoding nucleotide sequence in host cells (Cone et al., *Proc. Natl. Acad. Sci.. USA,* 81:6349–6353 (1984)). High level expression may also be achieved using inducible promoters, including, but not limited to, the metallothionine IIA promoter and heat shock promoters.

For long-term, high-yield production of recombinant proteins, stable expression is preferred. Expression vectors containing viral origins of replication or other appropriate expression control elements (e.g., promoter and enhancer sequences, transcription terminators, polyadenylation sites, etc.), and a selectable marker are useful for stably transforming host cells. As mentioned above, the selectable marker in the recombinant plasmid confers resistance to the selection and allows cells to stably integrate the plasmid into their chromosomes and grow to form foci which in turn can be cloned and expanded into cell lines.

Both prokaryotic and eukaryotic expression vectors are familiar to one of ordinary skill in the art of vector construction and are described by Ausebel, et al., In Current Protocols in Molecular Biology, Wiley and Sons, New York (1993) and by Sambrook et al., Molecular Cloning: A Laboratory Manual, Cold Spring Harbor Laboratory, (1989).

Expression vectors may also include secretion signals, which allow the protein to cross the cell membrane and either pass completely out of the cell permitting more convenient purification, or else lodge in cell membranes, and thus attain its functional topology.

The vectors of this invention may also be selected for producing BDV polypeptides in the form of a fusion polypeptide. Such vectors and use thereof are well known in the art and are described in Ausebel, et al., In Current Protocols in Molecular Biology, Wiley and Sons, New York (1993) and by Sambrook et al., Molecular Cloning: A Laboratory Manual, Cold Spring Harbor Laboratory, (1989).

Depending upon the selected expression vector, compatible host cells are then selected. For prokaryotic expression, host cells include bacterial cells such as *E. coli* or *B. subtilis*. For eukaryotes, host cells may include filamentous fungi, plant cells, insect cells and mammalian cells. The latter are often used for the expression of polypeptides derived from eukaryotes.

The term "transformed" refers to the state of a host cell having received a vector containing the nucleic acids of interest. Transformation methods, which vary depending on the type of host cell, include the following: electroporation; transfection employing calcium chloride, DEAE-dextran and the like; lipofection; infection where the vector is an infectious agent; and other methods. The transformed cells also include the progeny of such cells.

D. Human BDV Polypeptides

One aspect of the present invention includes substantially purified BDV polypeptides that are encoded by the human BDV nucleic acids described in Section C. Accordingly, the phrase "BDV polypeptide" refers to a polypeptide having an amino acid residue sequence that comprises an amino acid residue sequence that corresponds, and preferably is identical, to a portion of a BDV molecule isolated from a human. In particular, a BDV polypeptide comprises an amino acid reside sequence that is encoded by and deduced from the BDV nucleic acids isolated from the three patients, H1, H2 and H3, as described in Section B.

Thus, a BDV polypeptide includes an amino acid residue sequence of an entire human BDV genome, or a portion thereof. A BDV polypeptide includes those that are either derived from a naturally occurring BDV polypeptide or are synthetic or recombinant as described herein. The latter non-natural BDV polypeptides share significant structural and functional characteristics peculiar to a naturally occurring BDV polypeptide of the present invention. Within the definition of a BDV polypeptide and corresponding encoding nucleic acid, are BDV isotypes, strains and related viruses. A BDV protein or polypeptide includes the full-length encoded protein of a particular BDV ORF, fragments thereof, proteins containing immunoepitopes of the BDV polypeptides of this invention, and functional equivalents of the foregoing. The phrase "substantially purified" and its equivalents with regard to BDV polypeptides is described in Section A. Essentially, a polypeptide is substantially purified when it is separated from the native contaminants which accompany it in its natural state. Thus, a polypeptide which is purified from a body sample, chemically synthesized or synthesized by recombinant DNA techniques will be substantially free from the naturally-associated components found in each of those enviroments.

Preferred polypeptide regions in the BDV genome are those complete polypeptides or portions thereof that are encoded by the open reading frames (ORF) present in the BDV genome. ORF encode the p24, p16, p56, p40 and L polymerase polypeptides as more fully described in the Examples. Particularly preferred p24 polypeptides encoded by full-length ORF p24 are shown in FIGS. 8A, 8B and 8C that are also respectively listed as SEQ ID NO 20, SEQ ID NO 21 and SEQ ID NO 22. Also preferred are p24 polypeptide fragments containing at least the amino acid sequence, presented in single letter code, MATGPSSLVDSLEDEEDP (SEQ ID NO 32) and RIYPQLPSAPTADEWDIIP (SEQ ID NO 33).

Similarly, preferred p16 polypeptides encoded by full-length p16 ORF are shown in FIGS. 9A, 9B and 9C that are also respectively listed as SEQ ID NO 23, SEQ ID NO 24 and SEQ ID NO 25. Also preferred are p16 polypeptide fragments containing at least the amino acid sequence, presented in single letter code, MNSKH-SYVELKGKVIVPG (SEQ ID NO 34) and RLRNIGVG-PLGPDIRSSGP (SEQ ID NO 35).

Also preferred are the p56 polypeptides encoded by full-length p56 ORF shown in FIGS. 10A and 10B that are also respectively listed as SEQ ID NO 26 and SEQ ID NO 27. Further preferred are p56 polypeptide fragments containing at least the amino acid sequence, presented in single letter code, GLSCNTDSTPGLIDLEIR (SEQ ID NO 36), RSKLRRRRRDTQQIEYLV (SEQ ID NO 37) and LIS-LCVSLPASFARRRRLGRWQE (SEQ ID NO 38).

A further preferred human BDV p40 full-length polypeptide encoded by p40 ORF has an amino acid residue sequence shown in FIGS. 11A, 11B and 11C that are also respectively listed as SEQ ID NO 28, SEQ ID NO 29, SEQ ID NO 30. Further preferred are p40 polypeptide fragments containing at least the amino acid sequence, presented in single letter code MPPKRRLVDDADAMEDQD (SEQ ID NO 39), MEDQDDLYEPPSSLPKLP (SEQ ID NO 40) and ELSGEISAIMRMIGLTGLN (SEQ ID NO 41).

Another preferred human BDV polypeptide is the catalytic domain polypeptide from L polymerase having an amino acid residue sequence shown in FIG. 12 and as listed in SEQ ID NO 31.

In one aspect, a BDV polypeptide of this invention is characterized by having the capacity to immunoreact with BDV antibodies raised in response to BDV infection in a subject for use in detecting BDV antigens in a sample. In one embodiment, such detection is useful for diagnosing subjects suspected of having BDV for either confirming or negating BDV as the infectious agent as further described in the Methods Sections below. Preferably, a BDV polypeptide of this invention is further characterized by its ability to immunologically mimic an epitope (antigenic determinant) expressed by BDV. Such a BDV epitope will allow immunologic detection of the virus or polypeptide in a physiological sample with reasonable assurance. Usually, although not in all cases. it will be desirable that the epitope be immunologically distinct from viruses other than BDV to allow for differential diagnosis of viral presence. Such a polypeptide is useful herein as a component in an inoculum for producing antibodies that immunoreact with native BDV protein for use in detecting the presence of such protein for use in the methods of this invention.

As used herein, the phrase "immunologically mimic" in its various grammatical forms refers to the ability of a BDV polypeptide of this invention to immunoreact with an antibody of the present invention that recognizes a conserved native epitope of BDV as defined herein.

It should be understood that a subject polypeptide need not be identical to the amino acid residue sequence of the three human BDV amino acid sequences encoded by the respective patient-specific isolated nucleic acids, so long as the polypeptides are able to bind to patient-derived anti-BDV antibodies and are able to generate anti-polypeptide antibodies that are useful in detecting BDV polypeptides in a subject, both of which are as described in Section F.

A subject polypeptide includes any analog, fragment or chemical derivative of a polypeptide whose amino acid residue sequence is shown herein so long as the polypeptide has the characteristics described herein. Therefore, a present polypeptide can be subject to various changes, substitutions, insertions, and deletions where such changes provide for certain advantages in its use. In this regard, a BDV polypeptide of this invention corresponds to, rather than is identical to, the sequence of BDV where one or more changes are made and it retains the ability to immunoreact with anti-BDV antibodies and can be used as an immunogen to generate antibodies that immunoreact with BDV polypeptides.

The term "analog" includes any polypeptide having an amino acid residue sequence substantially identical to a sequence specifically shown herein in which one or more residues have been conservatively substituted with a functionally similar residue and which displays the aforementioned characteristics. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite activities.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a BDV polypeptide has a sequence that is not identical to the sequence of human BDV of this invention, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form BDV epitopes, i.e., are not similar in structure to BDV.

Labels, solid matrices and carriers that can be used with the polypeptides of this invention are described hereinbelow.

Amino acid residue linkers are usually at least one residue and can be 40 or more residues, more often 1 to 10 residues, but do not form BDV epitopes. Typical amino acid residues used for linking are tyrosine, cysteine, lysine, glutamic and aspartic acid, or the like. In addition, a subject polypeptide can differ, unless otherwise specified, from the natural sequence of BDV by the sequence being modified by terminal-$NH_2$ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, a BDV polypeptide of the present invention is capable of inducing antibodies that immunoreact with BDV in a subject suspected of having BDV. In view of the well established principle of immunologic crossreactivity, the present invention therefore contemplates antigenically related variants of the polypeptides described herein. An "antigenically related variant" is a subject polypeptide that is capable of inducing antibody molecules that immunoreact with a BDV polypeptide fragment and with BDV.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

A BDV polypeptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, the disclosure of which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

Alternatively, a BDV polypeptide may be purified from a sample such as a cell or fluid. Both purification of a BDV polypeptide in a cell lysate as well as body fluid containing secreted viral proteins are contemplated. The natural BDV polypeptides may be isolated from the whole virus by conventional techniques, such as affinity chromatography. Conveniently, polyclonal or monoclonal antibodies obtained according to the present invention may be used to prepare a suitable affinity column by well known techniques. See, for example, Hudson and May, *Practical Immunology*, Blackwell Scientific Publications, Oxford, United Kingdom (1980), the disclosure of which is hereby incorporated by reference. A BDV polypeptide may also be purified to substantial homogeneity by standard techniques well known in the art, including selective precipitation, column chromatography, and the like.

With purification methods, a BDV polypeptide of the resent invention will be typically from about 50% or ore pure, preferably at least 80% pure, and more preferably, at least 95% pure. Using conventional techniques of protein purification, homogenous polypeptide compositions of at least about 99% can be obtained.

A preferred method for producing a BDV polypeptide, other than direct purification from a body sample such as a cell lysate or fluid sample, involves the expression in host cells of recombinant DNA molecules in which a BDV nucleic acid encodes a desired portion, whether synthetic or natural, of the BDV genome as discussed in Section C. Preferred expression vectors and BDV nucleic acids are described above for expressing BDV recombinant polypeptides as previously discussed. The expressed BDV polypeptide is thus referred to as a BDV recombinant polypeptide. If the expression vector selected for use is designed to operatively link the BDV polypeptide to another molecule, such as GST or MBP, a fusion polypeptide is expressed that contains BDV linked thereto. The latter compositions are useful in purification of expressed fusion polypeptides. Thereafter, the expressed fusion polypeptide is used in accordance with the methods of the invention or can be separated from the other molecule in the fusion polypeptide.

A BDV polypeptide, purified, synthesized or expressed, can be used, inter alia, in the diagnostic methods and systems of the present invention to detect BDV and antibodies thereto present in a sample, or can be used to prepare an inoculum as described herein for the preparation of antibodies that immunoreact with conserved epitopes on BDV.

E. Human BDV Anti-Polypeptide Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

The phrase "substantially purified" means that the antibody molecules do not immunoreact with the stated antigen at levels within one order of magnitude, and preferably within two orders of magnitude, of the level of immunoreaction with a species of antigen recited to immunoreact with the antibody molecule when immunoreaction is expressed as an equilibrium constant between bound (immunoreacted) and nonbound antigen.

An antibody of the present invention, i.e., an anti-BDV antibody, in one embodiment is characterized as comprising antibody molecules that immunoreact with human BDV proteins and polypeptides thereof as described in Section D. In other embodiments, an anti-BDV antibody is characterized as being capable of immunoreacting with any species of BDV protein or polypeptide or fragments thereof.

Antibody immunoreactivity with BDV-containing antigens can be measured by a variety of immunological assays known in the art. Exemplary immunoreaction of an anti-BDV antibody with a BDV polypeptide is described in Section F and in the Examples.

An antibody of the present invention is typically produced by immunizing a mammal with an inoculum containing an BDV polypeptide of this invention and thereby induce in the mammal antibody molecules having immunospecificity for immunized BDV polypeptide. The antibody molecules are then collected from the mammal and isolated to the extent desired by well known techniques such as, for example, by using DEAE Sephadex to obtain the IgG fraction.

The preparation of antibodies against a polypeptide is well known in the art. [See Staudt et al., *J. Exp. Med.* 157:687–704 (1983)]. Briefly, to produce a peptide antibody composition of this invention, a laboratory mammal is inoculated with an immunologically effective amount of a BDV polypeptide, typically as described in the Examples. The anti-BDV polypeptide antibody molecules thereby induced are then collected from the mammal and those immunospecific for both the BDV polypeptide and isolated BDV are isolated to the extent desired by well known techniques such as, for example, by immunoaffinity chromatography.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" or "immunogen" in its various grammatical forms is used herein to describe a composition containing a BDV polypeptide of this invention as an active ingredient used for the preparation of antibodies against an BDV polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. Nos. 4,493,795, 3,791,932 and 3,839,153. In addition, a site-directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958.

Exemplary additional linking procedures include the use of Michael addition reaction products, di-aldehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly D-lysine:D-glutamic acid, and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen is well known in the art. Inocula typically contain polypeptide concentrations of about 10 micrograms ($\mu$g) to about 500 milligrams (mg) per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent, i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The antibody so produced can be used, inter alia, in the diagnostic methods and systems of the present invention as described in Section F and in the Examples.

A preferred anti-BDV antibody is a monoclonal antibody and is used herein as exemplary of an anti-BDV antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may contain an antibody molecule having a plurality of antibody combining sites, each immunospecific for a different epitope, e.g., a bispecific monoclonal antibody.

A monoclonal antibody of this invention comprises antibody molecules that bind to human BDV protein and polypeptides derived thereof.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature*, 256:495–497 (1975), the description of which is incorporated by reference. The hybridoma supernates so prepared can be screened for the presence of antibody molecules that immunoreact with a BDV polypeptide.

Briefly, to form the hybridoma from which the monoclonal antibody composition is produced, a myeloma or other self-perpetuating cell line is fused with lymphocytes obtained from the spleen of a mammal hyperimmunized with a BDV antigen, such as is present in a PS polypeptide of this invention. The polypeptide-induced hybridoma technology is described by Niman et al., *Proc. Natl. Acad. Sci.*, *USA*, 80:4949–4953 (1983), the description of which is incorporated herein by reference.

It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA), well known to those of ordinary skill in the art.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal Essential Medium (DMEM; Dulbecco et al., *Virol.* 8:396 (1959)) supplemented with 4.5 gm/1 glucose, 20 mm glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci., USA*, 86:5728–5732 (1989); and Huse et al., *Science*, 246:1275–1281 (1989). Thus, recombinant BDV antibodies are also contemplated for use in this invention. Recombinant human BDV antibodies include those against BDV polypeptides as well as those generated in a human in response to BDV infection. For the latter, recombinant antibodies are prepared once a nucleic acid encoding such an antibody has been isolated from a human and cloned. Thus, the nucleic acid segments that encode these antibodies are a further part of the invention. These segments can be used in expression vectors as described in Section C for the high level expression of a BDV antibody sequence and as desired, the collection and purification of the light chains, heavy chains, light/heavy chain dimers or intact antibodies, binding fragments, or any other forms such as single chain constructs that may follow.

The monoclonal antibodies of this invention can be used in the same manner as disclosed herein for antibodies of the present invention.

Also contemplated by this invention is the hybridoma cell, and cultures containing a hybridoma cell that produce a monoclonal antibody of this invention.

F. Diagnostic Methods

1. Detecting Human BDV Nucleic Acids

In one aspect of the present invention, the presence of BDV nucleic acid is detected in a sample. While preferred, the detection of a BDV nucleic acid is not limited to humans, as the nucleic acid molecules and methods of this invention allow for the detection of related BDV species, isotypes and strains, and variants thereof. Thus, the methods of this invention are useful for detecting ongoing or past BDV infection via the detection of BDV nucleic acids, diseases caused by BDV, related viruses or variants thereof, as well as to eliminate the suspicion of BDV viral infection, either past or ongoing. The detecting of BDV is generally accomplished by hybridizing the nucleic acid in the sample with a BDV nucleic acid molecule of this invention or a region derived therefrom.

In one embodiment, the sample is a biological sample, tissues, cells, lysates thereof or body fluids, obtained from a subject suspected of having BDV. As such, the body sample is either isolated BDV-infectable cells or fluid samples containing BDV viral particles. A preferred isolatable BDV-infected cell type is peripheral blood mononuclear cells (PBMC). As described in the Examples, BDV-infectable cells are also contemplated to be cell lines that become infected with BDV following co-cultivation with BDV-infected subject-derived cells. A preferred BDV-infectable cell line is a human oligodendroglial cell line. Other BDV-infectable cell lines are also contemplated for use in the methods of this invention. In alternative embodiments, the sample is a laboratory sample including but not limited to cells, transfected or infected, lysates thereof or culture fluids, that may contain a BDV nucleic acid.

In detecting BDV nucleic acid, a nucleic acid molecule is designed for use in the hybridization methods as described herein to hybridize to a target BDV sequence in a sample. As defined herein, a "nucleic acid molecule" is a nucleotide sequence that is derived from a particular region of BDV genome. The specific sequence is dependent upon the desired BDV target sequence in the sample.

Since hybridization methods as described herein rely upon the substantial complementarity of a nucleic acid molecule to the target BDV sequence, the sequence of a particular nucleic acid molecule is so determined. The BDV sequence of the nucleic acid molecule may be derived from any known sequence of BDV, such as the C6BV strain or Strain V that were originally obtained in horses then passaged through rodents. Preferably, the nucleic acid molecules have a nucleotide sequence corresponding to a BDV sequence determined from human BDV isolates. Thus, as defined herein, the phrase "derived from" means that the nucleic acid molecule is substantially complementary to one strand of a known BDV nucleic acid or substantially identical to the other strand such that specific hybridization with the target human BDV nucleic acid in the body sample is obtained. Therefore, "derived from" is used to indicate a relative correspondence with the desired target sequence.

The sequence of such nucleic acid molecules need not have perfect complementarity with the BDV genome or cDNA synthesized therefrom, as long as substantial complementarity is maintained. The nucleic acid molecule may be derived from any region or portion of the selected target sequence with the only requirement being that the molecule be of sufficient length to allow for specific hybridization as defined in Section B1. Preferably, the molecule is at least 5 nucleotides in length, more preferably 10 nucleotides in length and most preferably, between 15 and 25 nucleotides in length. However, in certain situations, longer molecules are desirable, such as the full-length BDV human cDNAs of this invention. The specific length that is selected is dependent on the type of hybridization method used to screen a sample. As known to one skilled in the art, the conditions for hybridization, based on stringency of hybridization principles, varies with the length of the nucleic acid molecule.

Preferred human BDV genomes from which nucleic acid molecules are derived are those identified in the three BDV patients of this invention, as described herein and in the Examples. As more patient- or subject-specific sequences become available, nucleic acid molecules for use in the methods of this invention are similarly derived.

Detecting the presence of BDV nucleic acid in any sample, including a patient sample, may be performed by hybridization with the nucleotide region encoding a BDV polypeptide of this invention. For example, a BDV nucleotide encoding the p24 polypeptide corresponding to patients H1 (SEQ ID NO 20), H2 (SEQ ID NO 21) and H3 (SEQ ID NO 22) and polypeptides derived therefrom as described in Section D is one of the preferred embodiments. A preferred screening nucleic acid molecule sequence used is the p24 nucleotide sequence shown in SEQ ID NO 3, SEQ ID NO 4 and SEQ ID NO 5, or regions derived therefrom, that respectively correspond to the p24 sequence from patients H1, H2 and H3. For example, in particular, a preferred p24 nucleic acid for use in the methods described herein is a substantially purified nucleic acid encoding a human Borna disease virus (BDV) p24 polypeptide comprising an amino acid residue sequence selected from the group consisting of SEQ ID NO 20, SEQ ID NO 21, SEQ ID NO 22, MATGPSSLVDSLEDEEDP (SEQ ID NO 32)

and RIYPQLPSAPTADEWDIIP (SEQ ID NO 33). Other BDV nucleic acids in a sample corresponding to p16, p56, p40 and the catalytic domain are similarly identified with the human nucleic acids encoding the respective polypeptides as described in Sections D and E, respectively, and incorporated herein for use in the methods of this invention. As described below, the nucleic acid molecules are used as primers and probes.

In one aspect of detecting BDV nucleic acids, hybridizing is performed with the polymerase chain reaction (PCR). Depending on the region of EDV to be amplified, particular primers are selected as described below. Preferably the sample of nucleic acid from the subject is first converted to cDNA with methods well known in the art. Exemplary methods of preparing cDNA from BDV genomic RNA are described in the Examples.

The genetic material to be assayed is first denatured, typically by melting, to eliminate structures that may interfere with the synthesis of cDNA. The nucleic acid, preferably a cDNA, is subjected to a PCR amplification by treating (contacting) the sample with a PCR primer pair, each member of the pair having a preselected nucleotide sequence based on the design requirements as described in Section C above. Primers comprising a primer pair, having first and second primers, are capable of initiating a primer extension reaction by hybridizing to a template nucleotide sequence, preferably at least about 10 nucleotides in length, more preferably between 15 nucleotides in length and 25 nucleotides in length, that are present and preferably conserved within a BDV nucleotide segment template.

The first primer of a PCR pair is sometimes referred to as the "sense" primer because it is derived from the sense (coding strand or positive sense strand) and it hybridizes to the anti-sense (non-coding or negative sense strand) of a nucleic acid, i.e., a strand complementary to a coding strand. The first primer is also referred to as a forward or 5' primer. Accordingly, the second primer of a PCR primer pair is sometimes referred to herein as the "anti-sense" primer because it is derived from the anti-sense strand and it hybridizes to a sense strand of a nucleic acid. With respect to the BDV genome which is RNA, the primers of this invention listed in Table 1 are designed to amplify cDNA obtained from the genomic RNA. Accordingly, the coding sequence of the cDNA is referred to as anti-genomic or positive sense as are the primers that are derived therefrom. Similarly, the primers derived from the complementary strand are referred to as genomic or negative sense.

Preferred primers pairs for amplifying BDV p24, p16, p56, p40 and the catalytic domain of L polymerase are shown in the Examples.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR amplification product, thereby enriching the sample to be assayed for BDV genetic material. Thus, as defined herein an amplification product of this invention results from the amplification of a BDV nucleic acid, either genomic RNA or mRNA, by priming with synthesis of cDNA with random hexamers or with a particular antisense primer pair, respectively.

PCR is typically carried out by thermocycling, i.e., repeatedly increasing and decreasing the temperature of a PCR reaction admixture within a temperature range whose lower limit is about 30° C. to about 70° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribonucleotide triphosphates (polynucleotide synthesis substrates) DATP, dCTP, dGTP, and dTTP and a polymerase, typically thermostable, all in adequate amounts for primer extension (polynucleotide synthesis) reaction. An exemplary PCR buffer comprises the following: 50 mM KCl; 10 mM Tris-HCl; pH 8.3; 1.5 mM $MgCl_2$; 0.001% (wt/vol) gelatin, 200 $\mu$M dATP; 200 $\mu$M dTTP; 200 $\mu$M dCTP; 200 $\mu$M dGTP; and 2.5 units *Thermus aquaticus* DNA polymerase (U.S. Pat. No. 4,889,818) per 100 microliters of buffer.

The resulting solution (PCR admixture) is heated to about 90° C.–100° C. for about 1 to 10 minutes, preferably from 1 to 5 minutes. After this heating period, the solution is allowed to cool to a temperature which is preferable for primer hybridization, usually 50° C. to 60° C. The synthesis reaction may occur at from room temperature up to a temperature above which the polymerase (inducing agent) no longer functions efficiently. Thus, for example, if *E. coli* DNA polymerase I is used as inducing agent, the temperature is generally no greater than about 40° C. The thermocycling is repeated until the desired amount of PCR product is produced.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Examples of heat-stable enzymes include *Thermus aquaticus* DNA polymerase, *Pyrococcus furiosus* DNA polymerase, and *Thermatoga maratima* DNA polymerase, among others. Generally, the synthesis will be initiated at the 3' end of each primer and proceed in the 5' direction along the template strand, until synthesis terminates, producing molecules of different lengths or of the same length. There may be inducing agents, however, which initiate synthesis at the 5' end and proceed in the above direction, using the same process as described above.

The inducing agent also may be a compound or system which will function to accomplish the synthesis of RNA primer extension products, including enzymes. The inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al, *The Enzymes*, ed. P. Boyer, PP. 87–108, Academic Press, New York (1982). Amplification systems based on transcription have been described by Gingeras et al, in *PCR Protocols, A Guide to Methods and*

*Applications*, pp. 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al, eds., Academic Press, San Diego, Calif. (1990). Exemplary PCR methods for use in this invention are described in the Examples. The human BDV amplification products are then analyzed by size determination, hybridization with BDV-specific probes or by sequencing.

In another embodiment of this invention, hybridizing comprises determining the nucleotide sequence of human BDV nucleic acids in PCR amplification products as described above. A nucleic acid sequence analysis determination is also contemplated for non-PCR amplified nucleic acid samples isolated from patients.

For either of the above embodiments, such an analysis on a selected nucleic acid sample is approached by a combination of (a) physiochemical techniques, based on the hybridization or denaturation of a probe strand plus its complementary target, and (b) enzymatic reactions with endonucleases, ligases, and polymerases. Nucleic acid can be assayed as either DNA or RNA.

For sequencing, a sequence in the template nucleic acid may be known, such as where the primer to be formed can hybridize to known conserved BDV sequences in another species and initiates primer extension into a region of nucleic acids for sequencing purposes, or where previous sequencing has determined a region of nucleotide sequence and the primer is designed to extend from the recently sequenced region into a region of unknown sequence. This latter process has been referred to a "directed sequencing" because each round of sequencing is directed by a primer designed based on the previously determined sequence.

In a further aspect of the invention, the presence of BDV nucleic acid in a subject is determined by other hybridization means.

In one approach for detecting the presence of BDV RNA or cDNA thereof in a duplex, an oligonucleotide that is hybridized in the duplex includes a label or indicating group that will render the duplex detectable. Typically such labels include radioactive atoms, chemically modified nucleotide bases, and the like.

The oligonucleotide can be labeled, i.e., operatively linked to an indicating means or group, and used to detect the presence of a specific nucleotide sequence in a target template.

Radioactive elements operatively linked to or present as part of an oligonucleotide probe (labeled oligonucleotide) provide a useful means to facilitate the detection of a duplex. A typical radioactive element is one that produces beta ray emissions. Elements that emit beta rays, such as $^3$H, $^{12}$C, $^{32}$P and $^{35}$S represent a class of beta ray emission-producing radioactive element labels. A radioactive oligonucleotide probe is typically prepared by enzymatic incorporation of radioactively labeled nucleotides into a nucleic acid using kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate forming compound such as an EDTA-analogue so that a fluorescent lanthanide complex is formed. See U.S. Pat. Nos. 4,374,120, 4,569,790 and published Patent Application Nos. EP0139675 and WO87/02708.

Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a duplex renders the duplex itself labeled and therefore distinguishable over other nucleic acids present in a sample to be assayed. Detecting the presence of the label in the duplex and thereby the presence of the duplex, typically involves separating the duplex from any labeled oligonucleotide probe that is not hybridized to a duplex.

Techniques for the separation of single stranded oligonucleotide, such as non-hybridized labeled oligonucleotide probe, from duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the duplex that is bound to an insoluble matrix. Exemplary is the Southern blot technique, in which the matrix is a nitrocellulose sheet and the label is $^{32}$P (Southern, *J. Mol. Biol.*, 98:503, 1975).

The oligonucleotides can also be advantageously linked, typically at or near their 5'-terminus, to a solid matrix, i.e., aqueous insoluble solid support. Useful solid matrices are well known in the art and include cross-linked dextran such as that available under the tradename SEPHADEX from Pharmacia Fine Chemicals (Piscataway, N.J.); agarose, polystyrene or latex beads about 1 micron to about 5 mm in diameter, polyvinyl chloride, polystyrene, cross-linked polyacrylamide, nitrocellulose or nylon-based webs such as sheets, strips, paddles, plates microtiter plate wells and the like.

It is also possible to add "linking" nucleotides to the 5' or 3' end of the member oligonucleotide, and use the linking oligonucleotide to operatively link the member to the solid support.

In nucleotide hybridizing assays, the hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The term hybridizing and phrase "hybridizing conditions" and their grammatical equivalents, when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanidine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Hybridization can be carried out in a homogeneous or heterogeneous format as is well known. The homogeneous hybridization reaction occurs entirely in solution, in which both the oligonucleotide and the nucleic acid sequences to be hybridized (target) are present in soluble forms in solution. A heterogeneous reaction involves the use of a matrix that is insoluble in the reaction medium to which either the oligonucleotide, polynucleotide probe or target nucleic acid is bound.

Where the nucleic acid containing a target sequence is in a double-stranded (ds) form, it is preferred to first denature the nucleic acid, as by heating or alkali treatment, prior to conducting the hybridization reaction. The denaturation of the nucleic acid can be carried out prior to admixture with a oligonucleotide to be hybridized, or can be carried out after the admixture of the nucleic acid with the oligonucleotide.

Predetermined complementarity between the oligonucleotide and the template is achieved in two alternative manners. A sequence in the template nucleic acid may be known, such as where the primer to be formed can hybridize to conserved regions in other BDV species sequences and initiates primer extension into a region of nucleic acid for subsequent assaying purposes as described herein, or where previous sequencing has determined a region of nucleotide sequence and the primer is designed to extend from the recently sequenced region into a region of unknown sequence.

Effective amounts of the oligonucleotide present in the hybridization reaction admixture are generally well known and are typically expressed in terms of molar ratios between the oligonucleotide to be hybridized and the template. Preferred ratios are hybridization reaction mixtures containing equimolar amounts of the target sequence and the oligonucleotide. As is well known, deviations from equal molarity will produce hybridization reaction products, although at lower efficiency. Thus, although ratios where one component can be in as much as 100-fold molar excess relative to the other component, excesses of less than 50-fold, preferably less than 10-fold, and more preferably less the 2-fold are desirable in practicing the invention.

One hybridization means contemplated for use herein is detection of membrane-immobilized BDV target sequences. In the DNA (Southern) blot technique, specific regions of cDNA are detected by immobilizing the target sequences on a membrane. The specific regions of cDNA are prepared by either PCR amplification, by PCR amplification followed by digestion with restriction endonucleases or by digestion with a restriction endonuclease without PCR amplification. Genomic RNA is first isolated. Specific regions of the genomic RNA are then PCR amplified to generate target sequences that are then analyzed intact or subjected to restriction digestion.

The above-generated target sequences are then separated according to size in an agarose gel and transferred (blotted) onto a nitrocellulose or nylon membrane support. Conventional electrophoresis separates fragments ranging from 100 to 30,000 base pairs while pulsed field gel electrophoresis resolves fragments up to 20 million base pairs in length. The location on the membrane containing a particular target sequence is then determined by direct visualization of stained target. In other aspects, the sequence migration is determined by hybridization with a specific, labeled nucleic acid probe.

In alternative embodiments, target sequences are directly immobilized onto a solid-matrix (nitrocellulose membrane) using a dot-blot (slot-blot) apparatus, and analyzed by probe-hybridization. See U.S. Pat. Nos. 4,582,789 and 4,617,261.

Immobilized target sequences may be analyzed by probing with allele-specific oligonucleotide (ASO) probes, which are synthetic oligomers of approximately 20 nucleotides, preferably 17 nucleotides in length. These probes are long enough to represent unique sequences in the genome, but sufficiently short to be destabilized by an internal mismatch in their hybridization to a target molecule. Thus, any sequences differing at single nucleotides may be distinguished by the different denaturation behaviors of hybrids between the ASO probe and normal or mutant targets under carefully controlled hybridization conditions.

Alternatively, the target sequences may be detected in solution. Several rapid techniques that do not require nucleic acid purification or immobilization have been developed. For example, probe/target hybrids may be selectively isolated on a solid matrix, such as hydroxylapatite, which preferentially binds double-stranded nucleic acids. Alternatively, probe nucleic acids may be immobilized on a solid support and used to capture target sequences from solution. Detection of the target sequences can be accomplished with the aid of a second, labeled probe that is either displaced from the support by the target sequence in a competition-type assay or joined to the support via the bridging action of the target sequence in a sandwich-type format.

In the oligonucleotide ligation assay (OLA), a ligase is used to covalently join two synthetic oligonucleotide sequences selected so that they can base pair with a target sequence in exact head-to-tail juxtaposition. Ligation of the two oligomers is prevented by the presence of mismatched nucleotides at the junction region. This procedure allows for the distinction between known sequence variants in samples of cells without the need for purification. The joint of the two oligonucleotides may be monitored by immobilizing one of the two oligonucleotides and observing whether the second, labeled oligonucleotide is also captured.

In a further embodiment, nucleotide substitutions in BDV sequences are detected by scanning techniques. Three techniques permit the analysis of probe/target duplexes several hundred base pairs in length for unknown single-nucleotide substitutions or other sequence differences. In the ribonuclease (RNase) A technique, the enzyme cleaves a labeled RNA probe at positions where it is mismatched to a target RNA or DNA sequence. The fragments may be separated according to size and the approximate position of the mutation identified. See U.S. Pat. No. 4,946,773.

In the denaturing gradient gel technique, a probe-target duplex is analyzed by electrophoresis in a denaturing gradient of increasing strength. Denaturation is accompanied by a decrease in migration rate. A duplex with a mismatched base pair denatures more rapidly than a perfectly matched duplex.

A third method relies on chemical cleavage of mismatched base pairs. A mismatch between T and C, G, or T, as well as mismatches between C and T, A, or C, can be detected in heteroduplexes. Reaction with osmium tetroxide (T and C mismatches) or hydroxylamine (C mismatches) followed by treatment with piperidine cleaves the probe at the appropriate mismatch.

2. Detecting Human BDV Antigens and Antibodies

The human BDV polypeptides and antibodies of the present invention respectively described in Sections D and E are useful in various diagnostic applications for detecting BDV, BDV antigens and antibodies thereto in a sample. In preferred aspects, the sample is from a human subject suspected of being infected with BDV. Along with detection of BDV nucleic acids as described above, the detection of human BDV antigens and/or antibodies thereby allows for an additional means for diagnosis of a subject positive for BDV infection, that may or not be made concurrent with other forms of diagnosis, such as behavioral analyses.

Preferred immunoassay methods for use in BDV antigen or antibody include liquid phase immunoassays, immunoblot analyses such as Western blot, competitive and noncompetitive protein binding assays, enzyme-linked immunosorbant assays (ELISA), immunofluorescence analysis including flow cytometry, and others commonly used and widely described in scientific and patent literature, and many employed commercially. All of these assays are well known to one of ordinary skill in the art. An exemplary ELISA assay for detecting BDV is described in International Publication WO96/21020, the disclosures of which are hereby incorporated by reference.

Thus, in one embodiment, a method for detecting a BDV antigen in a sample comprises the steps of:

(a) contacting a sample with an anti-human BDV polypeptide antibody of this invention, such as an anti-human BDV p24 polypeptide antibody comprising antibody molecules that immunoreact with human BDV and a p24 polypeptide comprising an amino acid residue sequence selected from the group consisting of SEQ ID NO 20, SEQ ID NO 21, SEQ ID NO 22, MATGPSSLVDSLEDEEDP (SEQ ID NO 32) and RIYPQLPSAPTADEWDIIP (SEQ ID NO 33) for a time period sufficient to allow the antibody to immunoreact with the BDV antigen present in the sample thereby forming an antigen:antibody complex; and (b) detecting the BDV antigen in the antigen:antibody complex.

Although described as exemplary, the method described above is not limited to a BDV p24 polypeptide but rather the method encompasses and extends to all the BDV compositions of this invention as described in Sections B, D and E.

As used herein, a sample includes cells and fluid samples obtained from a subject, preferably human, who is suspected of having BDV as previously defined. Such samples thus contain BDV antigen that includes BDV viral proteins, polypeptides and fragments thereof. A cellular body sample comprises any cell that is infectable by BDV. Preferred cell samples are PBMC as discussed previously. Preferred fluid samples include any that are suspected of containing BDV and BDV antigens including polypeptides. Such physiologic fluid samples are blood, plasma, serum, urine, cerebrospinal fluid, saliva and the like.

The BDV antibodies for use in the assay method are those described in Section E that recognize human BDV and specific polypeptides thereof. The specific remaining human BDV polypeptides including p16, p56, p40 and the catalytic domain polypeptides are as described in Section D and are incorporated herein for use in defining anti-BDV polypeptide immunoreactivity. For some aspects of detecting BDV antigen, the BDV antibodies are labeled directly. Alternatively, the assay methods are performed with the addition of a detecting antibody that binds to the anti-human BDV polypeptide antibody that is labeled. Preferred labels include enzymes, radioisotopes, fluorescent compounds, colloidal metals, chemiluminescent compounds, phosphorescent compounds and bioluminescent compounds. Labeling aspects are described further in Section G. In some aspects, the methods are preferably performed with the anti-human BDV polypeptide antibody immobilized on a solid support.

The term "contacting" refers to any means by which a body sample is exposed to an anti-human BDV polypeptide antibody, including admixing, adding, and the like, that allows for the BDV antigen in the sample to immunoreact with or bind specifically to the provided antibody. The resultant admixture is then maintained for a time period sufficient for the BDV antigen to come in contact with and bind to the antibody under immunoreaction conditions for a predetermined time period such as about 10 minutes to about 16–20 hours at a temperature of about 4° C. to about 45° C., such time being sufficient to allow formation of an antigen:antibody complex also referred to as an immunocomplex or immunoreaction product.

Immunoreaction assay conditions are those that maintain the biological activity of the immunochemical reagents of this invention and the BDV antigen sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art.

Those skilled in the art will understand that there are numerous well known clinical diagnostic chemistry procedures in which an immunochemical reagent of this invention can be used to form an antigen:antibody complex. Thus, various heterogenous and homogenous protocols, either competitive or noncompetitive, can be employed in performing an assay method of this invention.

Also contemplated is a method for detecting a BDV ligand in a sample, where the preferred BDV ligand is an antibody but is not so limited as it can include receptors, other soluble ligands and the like. A preferred method comprises the steps of:

(a) contacting a sample with a human BDV polypeptide of this invention, such as a substantially purified polypeptide corresponding to human Borna disease virus (BDV) p24 polypeptide comprising an amino acid residue sequence selected from the group consisting of SEQ ID NO 20, SEQ ID NO 21, SEQ ID NO 22, MATGPSSLVDSLEDEEDP (SEQ ID NO 32) and RIYPQLPSAPTADEWDIIP (SEQ ID NO 33), for a time period sufficient to allow the polypeptide to immunoreact with the BDV antibody thereby forming an immunoreaction complex; and (b) detecting the BDV antibody in the immunoreaction complex.

As with the methods to detect BDV antigen, the detection of BDV ligand in a sample, preferably serum, is obtained through the formation of a complex containing the BDV polypeptide and corresponding ligand. The complex is also referred to as an immunoreaction complex. The remaining human BDV polypeptides of this invention including p16, p56, p40 and the catalytic domain polypeptide, as previously defined in Section D, are similarly contemplated for use in the above method.

This approach also may utilize detection means by the addition of a detecting antibody that binds to the BDV antibody in the body sample. The detecting antibody thus contains a label that provides for detection in methods as described above and also including the indirect immunofluorescence focus assay.

C. Diagnostic Kits

Another aspect of the present invention is a diagnostic kit for use in detecting the presence of BDV nucleic acid, polypeptide or ligand thereof, preferably a BDV antibody, in a subject by analyzing a physiological sample from that subject. It will be readily appreciated that the presence of BDV is ascertained with kits providing means for detecting the BDV genome, BDV-specific antibodies, and BDV antigens.

A first type of kit is supplied for use with the subject nucleic acids as described in Section C and F1. Thus, the human BDV nucleic acids as previously described are thus used as probes and primers for detection, by hybridization means, of the BDV genome, transcripts thereof including cDNA, are provided in a kit. As previously described, hybridizing means preferably includes PCR and sequencing.

The kit comprises one or more containers comprising separate containers having a human BDV nucleic acid corresponding to human BDV p24, p16, p56, p40 and the catalytic domain polypeptide, for which the nucleic acids and encoded polypeptides have been previously defined in Sections C and D, and are therefore incorporated into this section for support thereof.

The kits of this invention comprise a packaging means in which the reagents to practice the method are contained. A packaging means can be any type of a container in which reagents can be secured. The term "package" refers to a solid matrix or material such as glass, plastic (e.g., polyethylene, polypropylene and polycarbonate), paper, foil and the like capable of holding within fixed limits a diagnostic reagent such as a polynucleotide of the present invention. Thus, for example, a package can be a bottle, vial, plastic and plastic-foil laminated envelope or the like container used to contain a contemplated diagnostic reagent.

"Instructions for use" of the packaged reagent are also typically included and include a tangible expression describing the reagent concentration or at least one assay method parameter such as the relative amounts of reagent and sample to be admixed, maintenance time periods for reagent/sample admixtures, use of control polynucleotide sequences, temperature, buffer conditions and the like.

In one aspect of providing a diagnostic kit, the nucleic acids may be labeled with a detectable label. Radioactive elements are useful labeling agents and may be useful herein. An exemplary radiolabeling agent is a radioactive element that produces alpha ray emissions. Elements which themselves emit alpha rays, such as $^{32}P$, $^{35}S$, and $^{33}P$ represent one class of alpha ray emission-producing radioactive element indicating groups. Particularly preferred is $^{32}P$. Also useful is a beta emitter, such $^{111}$indium or $^{3}H$.

The reagent species, polynucleotide or amplifying agent of any diagnostic system described herein can be provided in solution, as a liquid dispersion or as a substantially dry power, e.g., in lyophilized form.

The packaging materials discussed herein in relation to diagnostic systems are those customarily utilized in diagnostic systems.

The materials for use in the assay of this invention are ideally suited for the preparation of a kit having sufficient amounts of materials to perform at least one assay.

Additional types of kits are also supplied for use in this invention for the detection of BDV antigens and antibodies respectively with the subject anti-BDV-polypeptide specific antibodies and BDV polypeptides as described above. Thus, the diagnostic kit or system includes, in an amount sufficient to perform at least one assay, a subject BDV polypeptide and/or a subject antibody or monoclonal antibody of the present invention, as a separately packaged reagent. Exemplary diagnostic methods for detecting BDV in a body sample and utilizing a BDV polypeptide or antibody of this invention are described in Section F.

In another embodiment, a diagnostic system, preferably in kit form, is contemplated for assaying for the presence of a BVD polypeptide or anti-BVD antibody in a body fluid sample such as for monitoring the fate of therapeutically administered BVD polypeptide or anti-BVD antibody. The system includes, in an amount sufficient for at least one assay, a subject BVD polypeptide and/or a subject antibody as a separately packaged immunochemical reagent. Such kits may also comprise positive control samples containing eith BDV polypeptides and antibodies thereto and/or negative controls lacking such reagents.

Frequently, it will be desirable to include an inert extender or excipient to dilute the active ingredients, where the excipient may be present in from about 1 to 99% weight of total composition. Where a second antibody capable of binding to either a provided BDV anti-polypeptide antibody or to a sample antibody is employed in an assay, this will usually be present in a separate container. The second antibody is typically conjugated with a label as described below and formulated in an analagous manner to that of provided BDV polypeptides and antibodies.

Instructions for use of the packaged reagent(s) are also typically included in the kits for detecting BDV antigen or antibody. Such instructions generally include a tangible expression describing the reagent concentration or at least one assay method parameter such as the relative amounts of reagent and sample to be admixed, maintenance time periods for reagent/sample admixtures, temperature, buffer conditions and the like.

As used herein, the term "package" refers to a solid matrix or material such as glass, plastic (e.g., polyethylene, polypropylene or polycarbonate), paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide or antibody have been operatively affixed, i.e., linked so as to be capable of being immunologically bound by an antibody or antigen, respectively.

A diagnostic system of the present invention preferably also includes a label or indicating means capable of signaling the formation of an immunocomplex containing a polypeptide or antibody molecule of the present invention.

As used herein and as described in Section F, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethyl-rhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium or $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Auramneas, et al., *Scand. J. Immunol.*, Vol. 8 Suppl. 7:7–23 (1978), Rodwell et al., *Biotech.*, 3:889–894 (1984), and U.S. Pat. No. 4,493,795.

If desired, a reagent can be typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron ($\mu$) to about 5 millimeters (mm) in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system. The packaging materials discussed herein in relation to diagnostic systems are those customarily utilized in diagnostic systems.

EXAMPLES

The following examples are intended to illustrate but are not to be construed as limiting of the specification and claims in any way.

1. Isolation of Human BDV

A. Patient Profile

Coded serial blood samples from 33 randomly selected psychiatric patients, taken during acute disease episodes, and from twenty healthy blood donors were analyzed in a double-blind manner for the expression of BDV antigens in peripheral blood mononuclear cells (PBMC). Results from these studies led to the selection of three patients designated H1, H2, and H3, to attempt the isolation and molecular characterization of human BDV. These particular patients were selected based on their relative high numbers of positive PBMC for BDV antigens in serially collected blood samples. Patients were selected from two follow-up cohort studies with psychiatric patients in Berlin (Bode et al., *Nature Med.*, 1:232–236 (1995); Bode, *Curr. Top. Microbiol. Immunol.*, 190:101–128 (1995)).

Patients H1 and H3 with an acute mental disorder were from the Psychiatric Department, Benjamin Franklin Hospital, Free University of Berlin, Germany. Samples and clinical diagnoses were given by R. Ferszt; additional psychological evaluation was conducted by E. Severus. Patient H2 with a chronic mental illness was from the Psychiatric Department, Theodor-Wenzel-Werk and District Hospital Berlin-Zehlendorf (Heckeshorn), Germany. Samples and clinical records were given by W. Schwalbe, and further comments on the clinic history provided by G. Arkenberg and E. H. Kang-Welberts. Clinical diagnoses were according to DSM-III-R criteria (American Psychiatric Association, 1987).

H1 is a 45-year-old female patient with a Bipolar Disorder mixed with psychotic features (DSM-III-R:296.64). H2 is a 37-year-old male patient suffering from a chronic Obsessive Compulsive Disorder (DSM-III-R:300.30; 305.00), who has been hospitalized for the last fourteen years. H3 is a 55-year-old male patient with a history of a Bipolar disorder (DSM-III-R:296.70).

B. Isolation of Human BDV from Patients

Preliminary studies done using ultrasonically disrupted BDV antigen-positive patients' PBMC to inoculate young rabbit brain cells failed to allow BDV growth. In addition, previously reported attempts to recover BDV using cerebrospinal fluid from BDV seropositive patients to infect fetal rabbit brain cells were also unsuccessful (Rott et al., *Arch. Virol.*, 118:143–149 (1991)). Therefore, an alternative approach was adopted based on the co-cultivation of patients' PBMC with BDV-infectable cells such as a human oligodendroglial cell line, previously documented to be highly sensitive to BDV infection (Briese et al., *Proc. Natl. Acad. Sci., USA*, 89:11486–11489 (1992)).

Samples of PBMC from healthy control individuals were obtained from blood donors officially registered with the Federal Health Office (BGA), Germany (Bundesgesundhbl, 31:286 (1988)).

Blood samples of 9 ml from each of the control and patient subjects were collected at the hospital in the presence of sodium citrate (10 mM final concentration) as anticoagulant. Samples were coded and separated into plasma and PBMCs by centrifugation on Ficoll-hypaque. PBMCs were processed for detection of virus antigen and BDV RNA in a double-blind manner.

For virus isolation, PBMC samples isolated within eight hours after blood sample collection were then transported from the site of collection in the hospital to a tissue culture facility where BDV-infected material had never been previously used. For co-cultivation experiments, PBMC ($1\times10^5$) were resuspended in DMEM containing 10% FCS and added to $1\times10^5$ cells of a human oligodendroglial (OL) cell line previously documented to be highly sensitive to BDV. For isolation of human BDV, PBMCs were used not later than 12 hours after their isolation from blood samples. Every three days the cells were subcultured at a 1:4 dilution. Passages were done by disaggregation of the cells using trypsin treatment. Expression of BDV antigen was examined every three passages using immunofluorescence procedures.

Isolation of BDV required least 10 passages of co-cultured OL cells. All co-cultivation studies were conducted in a double-blind manner.

After the twelvth passage, OL cells co-cultured with PBMC obtained from patients H1, H2 or H3 expressed high levels of BDV antigens. Infectivity titers associated with BDV-infected cell were determined using a focus forming unit (FFU) assay. For this assay, BDV-infected OL cells ($1\times10^7$) were resuspended in 1 ml of DMEM containing 1% FCS and ultrasonicated. Infectivity was determined on young rabbit brain cell monolayers. Virus yields was in the range of 5 to $10\times10^{6\ PFU}/1\times10^7$ OL cells.

As shown herein and below, three patients with mood disorders have been shown to contain infectious BDV. BDV isolation required long-term co-cultivation (ten or more passages) of the patients' PBMCs with OL cells, a cell line highly susceptible to BDV infection. Virus isolation also required the use in co-cultivation experiments of multiple serially collected PBMCs samples from each corresponding patient, specifically, ten, three, and ten serial samples for patients H1, H2 and H3, respectively. Successful virus isolation appeared to correlate with the use for the co-cultivation experiments of PBMCs samples expressing the highest levels of virus antigens and RNA.

2. Detection and Characterization of BDV RNA in Patients

A. PCR Amplification of BDV Nucleic Acid Fragments

Polymerase chain reaction (PCR) amplification of BDV nucleic acid was performed on RNA isolated from PBMC or from OL that had been co-cultured with PBMC as described above. The particular PCR procedure used was reverse-transcriptase PCR (RT-PCR) in which total RNA isolated from infected cells is first reverse transcribed into cDNA that is then used as the template for PCR. PCR primers are thus designed to hybridize to the cDNA template for detecting various regions of BDV genome.

Amplification of BDV RNA from the PBMC preparation as described below documented BDV infection of human patients. The detection of BDV RNA in OL confirmed the infectivity of BDV presence in patients suspected of having BDV. From either PBMC or OL cell preparations, total RNA was extracted from the cells using the acid guanidinium thiocyanate-phenol chloroform method described by Chomczynski et al., *Anal. Biochem.,* 162:156–159 (1987)). Purified RNA (0.5 to 2.0 μg) was reverse transcribed to form cDNA using 50 U of Moloney murine leukemia virus reverse transcriptase (GIBCO BRL, Gaithersburg, Md.) and random hexamers (2.5 mM) as primers (Krug et al., *Methods Enzymol.,* 152:316 (1987).

As a first determination of the presence of BDV in humans, PBMC were screened for the presence of BDV p24 nucleotide sequences by amplifying cDNAs prepared above using BDV-specific primers 2.1 and 2.2 as listed in Tables 1 and 2. The position of the primers as well as others used to amplify various BDV polypeptide-encoding fragments of this invention are shown in FIG. 1. In the figure, a diagram of the entire BDV genome RNA (anti-genomic polarity) and relative location of primers are shown. The genome organization presented in the diagram is based on the complete sequence of two BDV RNA genomes as yet reported, strain V and C6BV (Briese et al., *Proc. Natl. Acad. Sci. USA,* 89:11486–11489 (1994); Cubitt et al., *J. Virol.,* 68:1382–1396 (1994); de la Torre, *J. Virol.,* 68:7669–7675 (1994)). The GenBank Accession Numbers for strain V and C6BV RNA genome sequences are U04608 and L27077, respectively.

The consensus nucleotide sequence, presented in compliance with the IUPAC-IUB Biochemical Nomenclature Commission (referred to herein as IUPAC) code and derived from the sequences reported by Cubitt et al. and Briese et al., is shown in FIG. 2A–FIG. 2M (SEQ ID NO 1). FIGS. 2A–2M also show the Cubitt et al. and Briese et al. sequences respectively labeled BDV JCT and BDV Briese. Dots in the BDV JCT and BDV Briese sequences indicate that both sequences are consistent with each other and thus comprise the consensus sequence shown in FIGS. 2A–2M and in SEQ ID NO 1. Nucleotide differences at specific nucleotide positions are shown for the BDV JCT and BDV Briese sequences. The substitutions as shown are then indicated in the consensus sequence in accordance with the IUPAC code.

The BDV-specific primers designated 2.1 and 2.2 for amplifying p24 were designed to allow for the amplification of the full length open reading frame (ORF) encoding the BDV p24 polypeptide. Table 1 indicates the following aspects: the designation of the primer, the nucleotide sequence listed in 5' to 3' direction, and the designated SEQ ID NO. The sequences and nucleotide positions of the p24 primers as well as the others described herein are based on the C6BV genome RNA sequence (Cubitt et al., *J. Virol.,* 68:1382–1396 (1994); de la Torre, *J. Virol,* 68:7669–7675 (1994)). The accession number for this sequence is L27077. Table 2 contains the polarity of the DNA primers based on the negative polarity of the BDV RNA genome and the nucleotide positions (nt) of the primers corresponding to the intact BDV RNA negative polarity genome based on the DNA sequence, presented in the anti-genomic polarity, as shown in FIG. 1.

Table 1

| Primer | Nucleotide Sequence* | SEQ ID NO |
|---|---|---|
| 2.1 | CAGGAGGCTCAATGGCAACG | 42 |
| 2.2 | TTTATGGTATGATGTCCCAC | 43 |
| 3.1 | ATCGAATCACCATGAATTCAAAGC | 44 |
| 3.2 | GTCAGTATTGCAACTAAGGC | 45 |
| 4.4 | GCACGCAATTAATGCAGC | 46 |
| 3030R | CAGTGTAGGCCTAAGCTTGTG | 47 |
| 2962F | AAGTTGAGAAGGCGGCGTAG | 48 |
| 4.3 | CGGTACGGTTTATTCCTGC | 49 |
| 5248F | TGACCATGAGCTCAACGGC | 50 |
| 5936R | GCATGATGATGTTAAGCAGGC | 51 |
| BV259F | TTCATACAGTAACGCCCAGC | 52 |
| BV829R | GCAACTACAGGGATTGTAAGGG | 53 |
| BV277F | GCCTTGTGTTTCTATGTTTGC | 54 |
| BV805R | GCATCCATACATTCTGCGAG | 55 |

*The nucleotide sequences are written in the 5' to 3' direction.

TABLE 2

| Primer | Polarity | Nucleotide Positions in BDV RNA Genome |
| --- | --- | --- |
| 2.1 | Anti-genomic | 1261–1280 |
| 2.2 | Genomic | 1859–1879 |
| 3.1 | Anti-genomic | 1882–1905 |
| 3.2 | Genomic | 2315–2334 |
| 4.4 | Anti-genomic | 2225–2242 |
| 3030R | Genomic | 3010–3030 |
| 2962F | Anti-genomic | 2962–2981 |
| 4.3 | Genomic | 3738–3756 |
| 5248F | Anti-genomic | 5248–5267 |
| 5936R | Genomic | 5915–5936 |
| BV259F | Anti-genomic | 259–278 |
| BV829R | Genomic | 808–829 |
| BV277F | Anti-genomic | 277–297 |
| BV805R | Genomic | 786–805 |

The conditions for PCR amplification were as follows: 94° C. for 5 min (1 cycle); 94° C. for 1 min, 55° C. for 1 min, 72° C. for 1 min (35 cycles); 72° C. extension for 10 min (1 cycle). Each PCR reaction used 1/10 of the cDNA product, 50 pmol of each primer, 1 U of Taq polymerase, 100 mM of each deoxynucleotide triphosphate, 50 mM KCl, 1.5 mM MgCl$_2$, 10 mM Tris-HCl (pH 9.0) and 0.1% Triton X-100 in a final volume of 50 μl.

The PBMC-amplified BDV p24 PCR products, not detectable by ethidium bromide staining, were then cloned and transformants screened with a 32p probe corresponding to internal p24 as described below in Example 2. In addition, the sequence of three independent clones for p24 ORF derived from each patient's PBMCs was also determined as described below in Example 2.

As a control for RNA quality, the cDNAs were also amplified with specific primers to generate a 192 bp GAPDH fragment (Buesa-Gomez et al., J. Med. Virol., 42:193–197 (1994)). Each RT-PCR assay also included two water samples as negative controls of environmental contamination, and a BDV-negative C6 RNA sample.

Figure 2A:
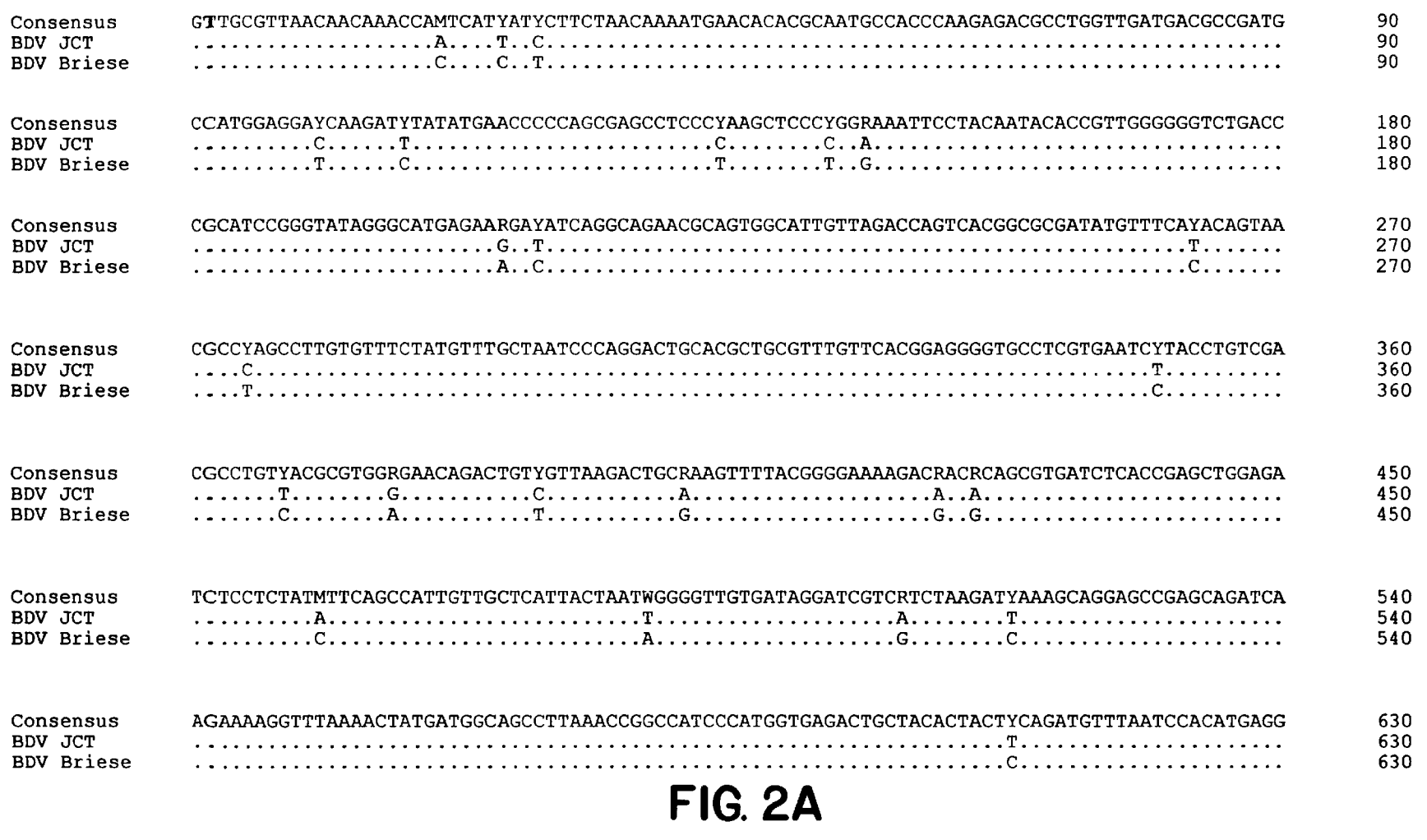

For PCR amplification of BDV p40 sequences, the PBMC-derived RNA prepared as described above is used in a nested PCR procedure using 2 pairs of primers. The first PCR is done using 1/10 of the cDNA product and BDV primers BV259F (anti-genomic polarity) and BV829R (genomic polarity), shown in Tables 1 and 2, corresponding to nucleotide positions 259 to 278 and 808 to 829, respectively, in the BDV genome as shown in FIGS. 2A–2B. The amplification step is performed as described above. The products of the first reaction are then used as the template for the second reaction which generates a smaller product, the sequence of which is nested within the first product. The second PCR is done using 1/25 of the RT-PCR product and the nested set of BDV primers: BV277F (anti-genomic polarity) and BVB05R (genomic polarity), corresponding to nucleotide positions 277 to 297 and 786 to 805, respectively, in the BDV genome. Amplification is done using the same cycle conditions as in the first PCR. The set of nested primers used amplifies a final 528 bp segment of BDV p40. The BDV specificity of the RT-PCR products is then determined by Southern blot hybridization using a $^{32}$P-labeled probe corresponding to internal sequences of the BDV p40 528 bp segment.

To unequivocally identify the isolated infectious agent as BDV, and determine its relationship to the BDV sequences directly derived from PBMCs, as well as to previously known BDV genomic sequences, RNA was extracted from OL cells co-cultivated with patients' PBMCs as described above. RNA was reverse transcribed and the corresponding cDNAs subjected to PCR as described below using pairs of primers to amplify three BDV open reading frames (ORFs), corresponding to the p24, p16, and p56 BDV polypeptides, as well as the putative catalytic domain of the BDV L polymerase. RT-PCR was followed by cloning and sequencing of the amplified human BDV products. BDV p40 is also amplified from the OL cells as described above for PBMC.

Full length p24 ORF having 603 nt including 15 additional nt of primer sequences outside the ORF and a 426 nt p16 ORF were amplified by PCR using primer pairs 2.1+2.2, and 3.1+3.2, respectively (Table 1 and FIG. 1). Amplification of full length p56 ORF having 1509 bp was done using two pairs of primers, 4.4+3030R and 2962F+4.3 (Table 1 and FIG. 1), that generated two overlapping PCR fragments with sizes of 805 bp and 794 bp, respectively, that covered the entire BDV p56 ORF. The putative catalytic domain of BDV L polymerase (de la Torre, J. Virol., 68:7669–7675 (1994)) having a fragment size of 688 nt was amplified using primers BV 5248F and BV 5936R (Table 1 and FIG. 1). PCR primers specific for the human BDV isolates of this invention are readily made based on the sequence information presented in Example 2 and are used in PCR as described herein to amplify patient BDV.

In all cases PCR products were readily detected by gel electorphoresis following ethidium bromide staining of the gel. In control assays, however, RT-PCR assays done with RNA extracted from OL cells co-cultivated with BDV-antigen negative PBMC samples from healthy control individuals failed to amplify any BDV-specific product in several independent experiments.

B. Detection of Human BDV PCR Products

1) Molecular Characterization of Human BDV Isolates

Figure 2C:
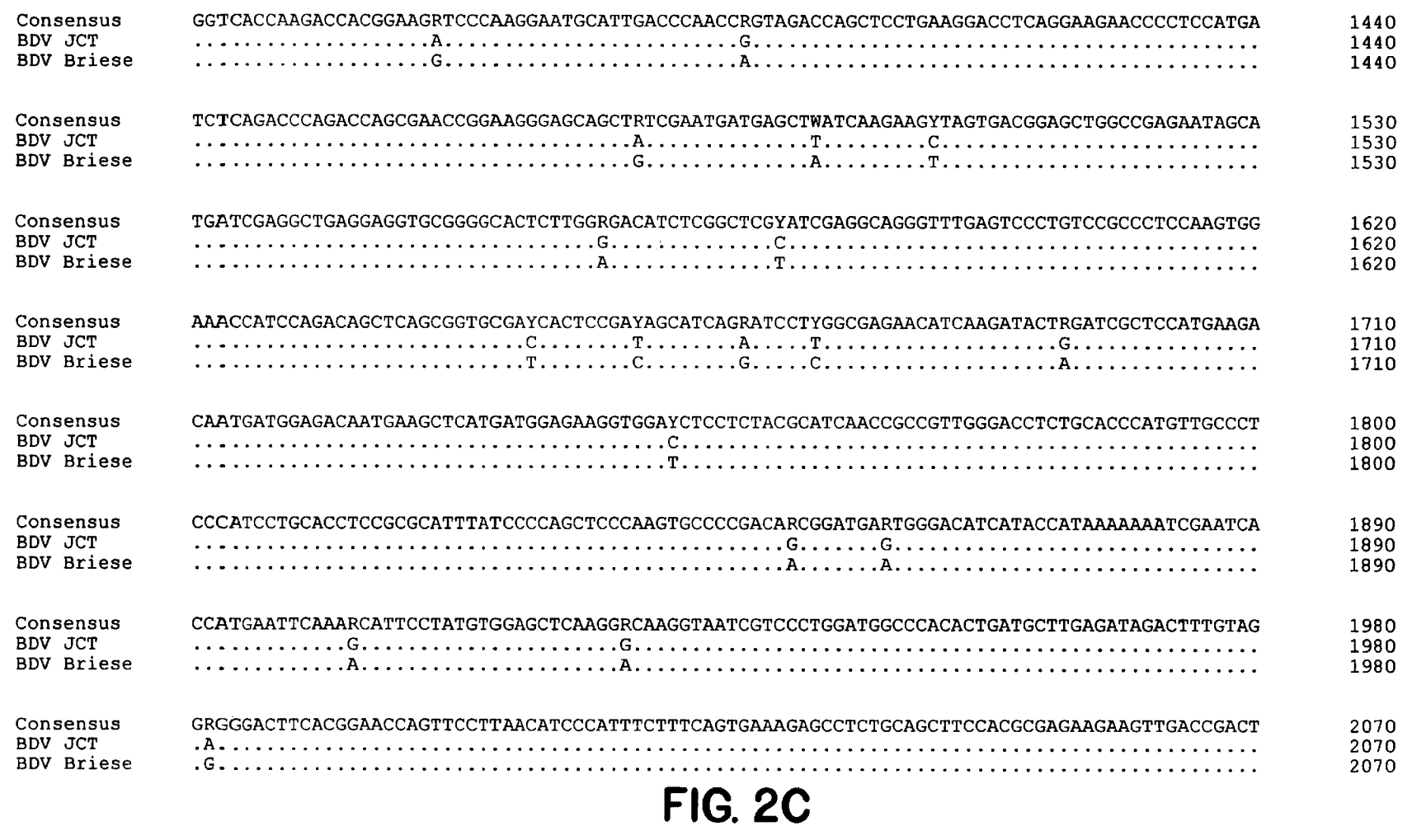
Figure 2E:
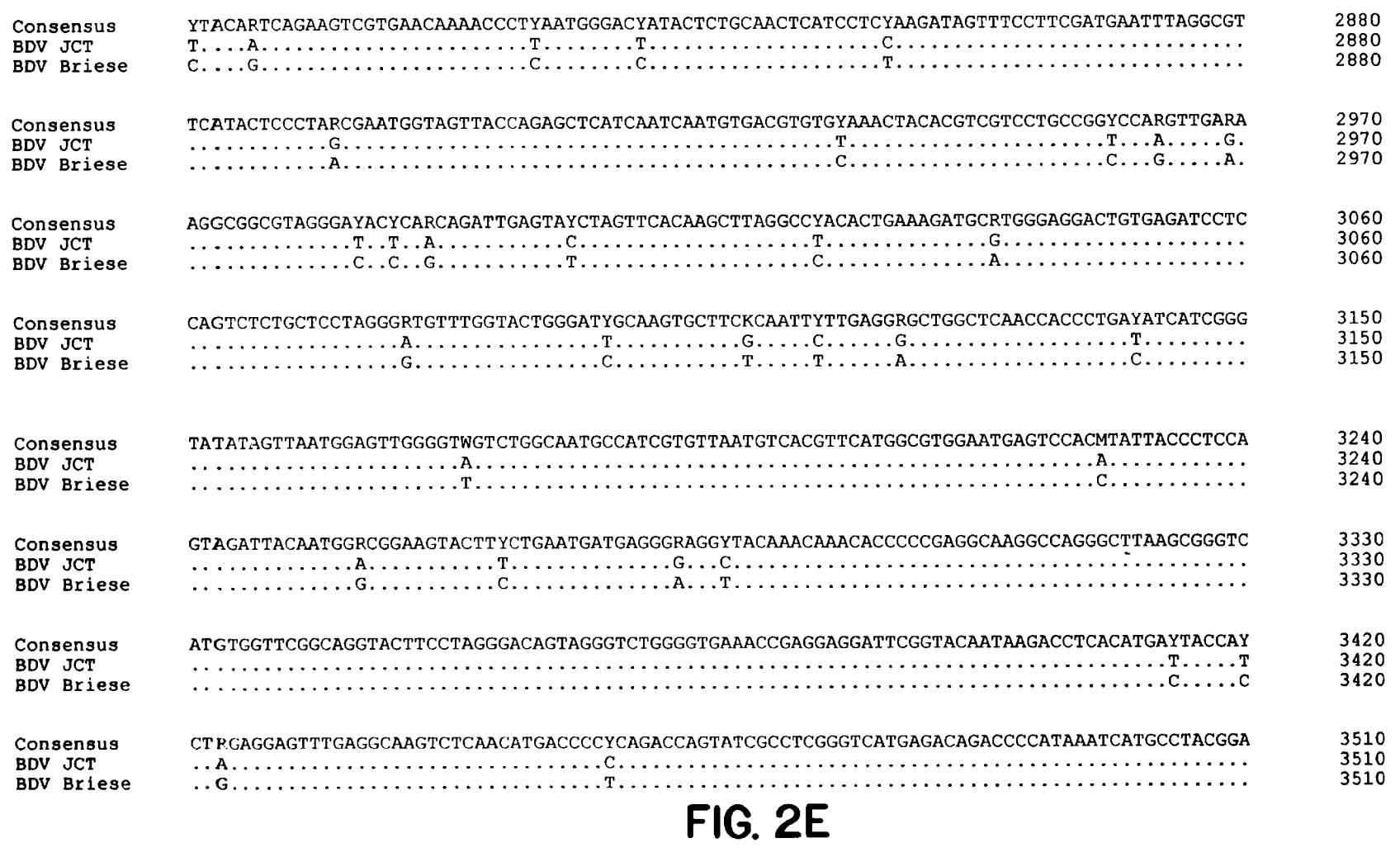
Figure 2F:
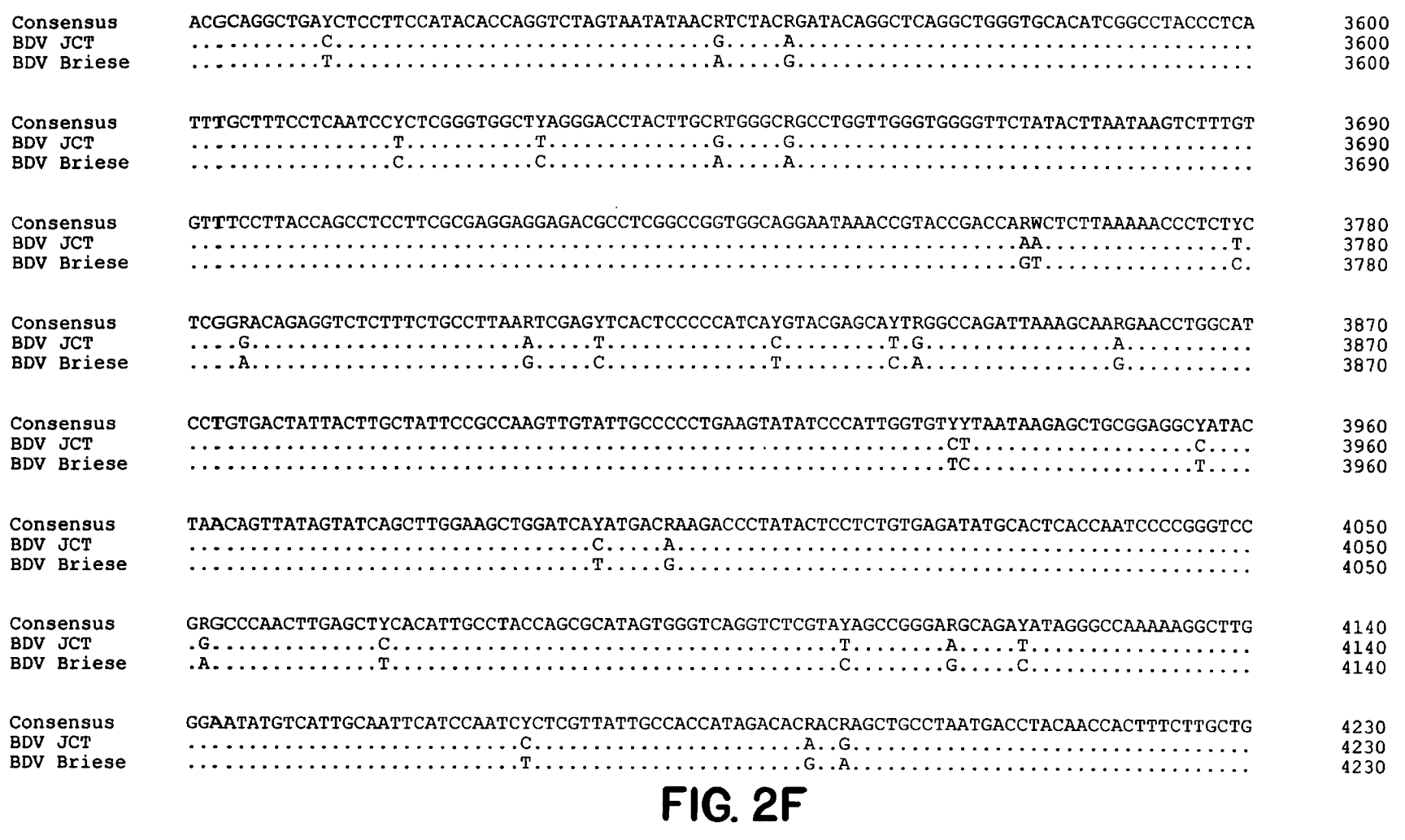
Figure 2G:
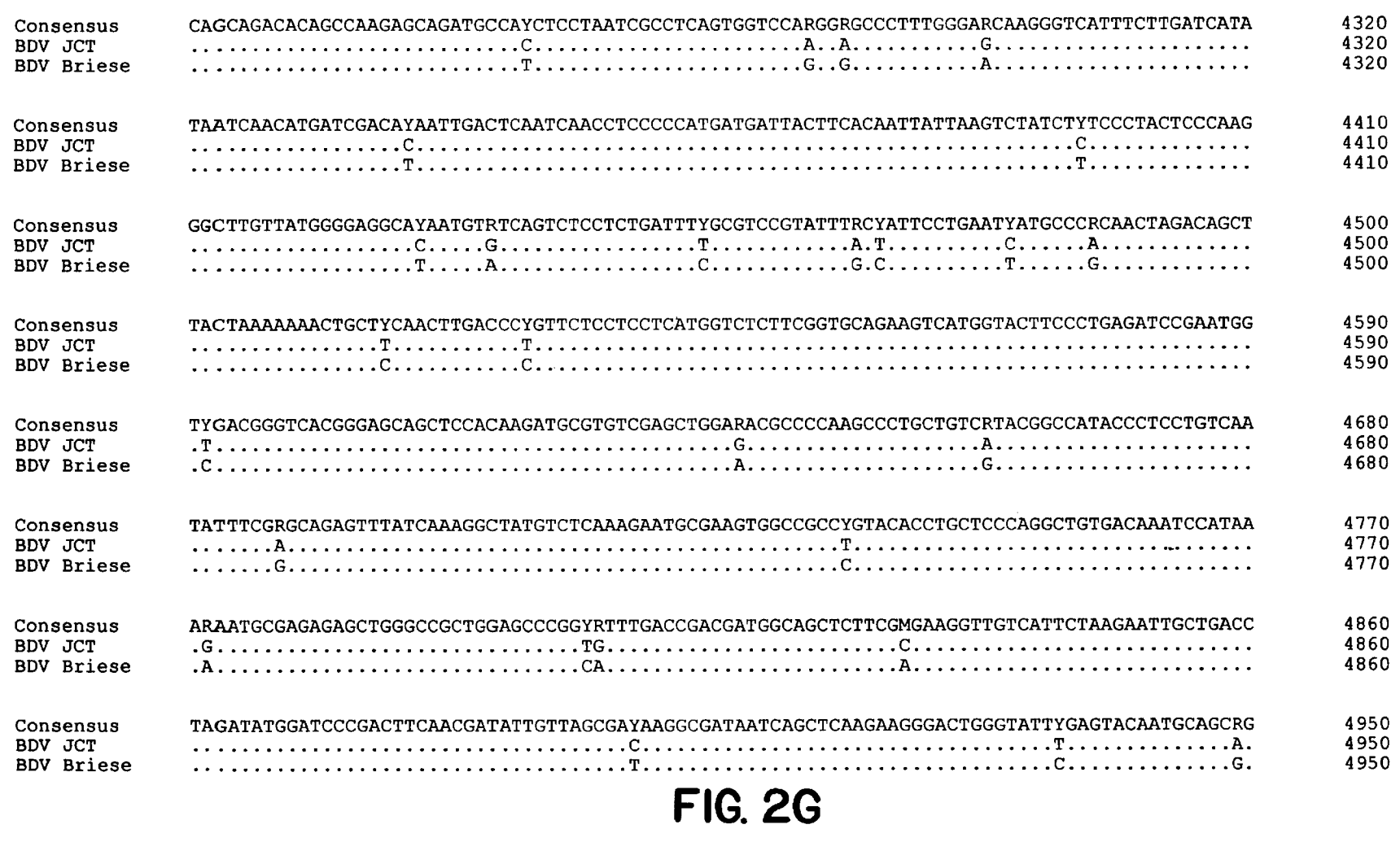
Figure 2H:
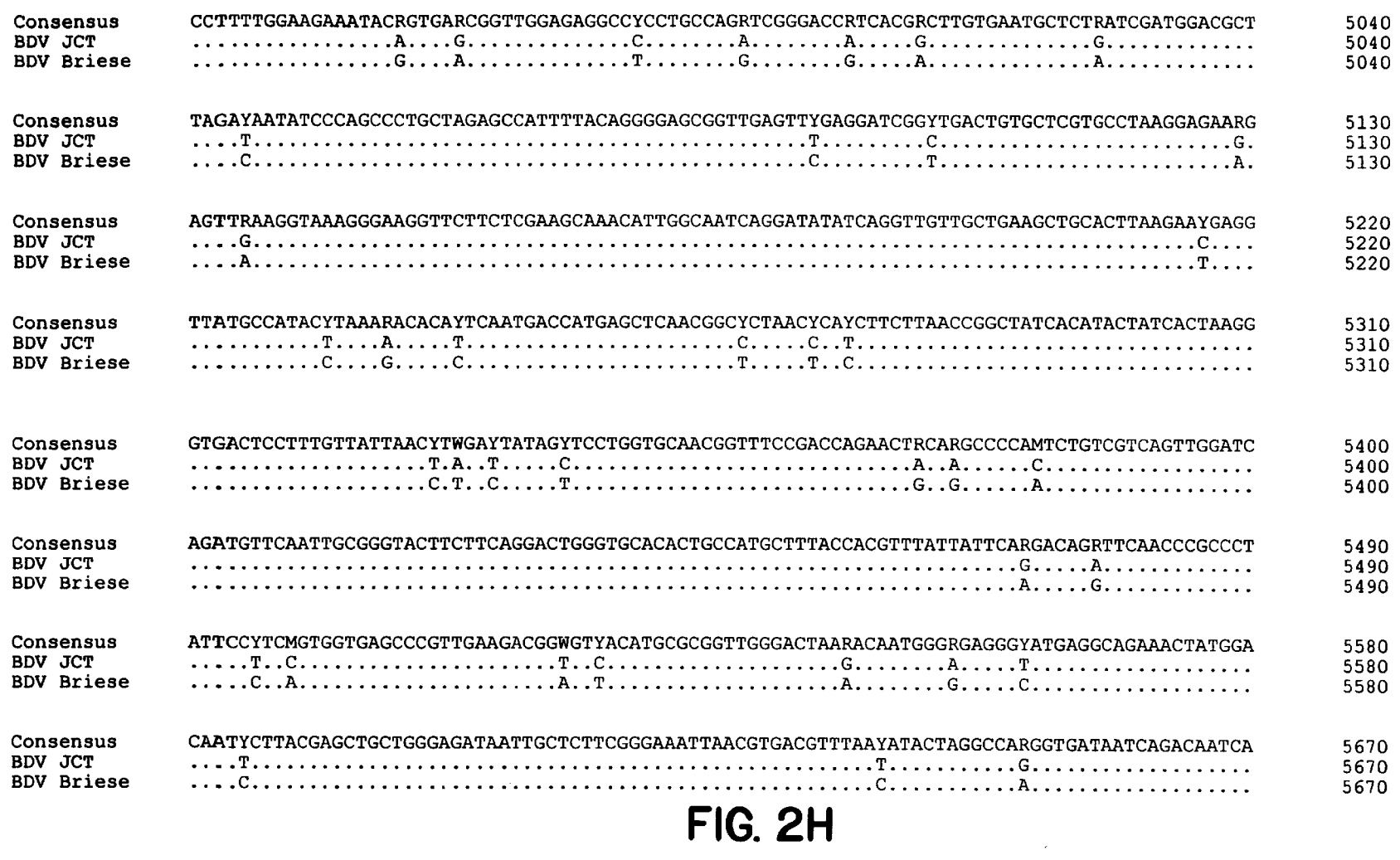
Figure 2K:
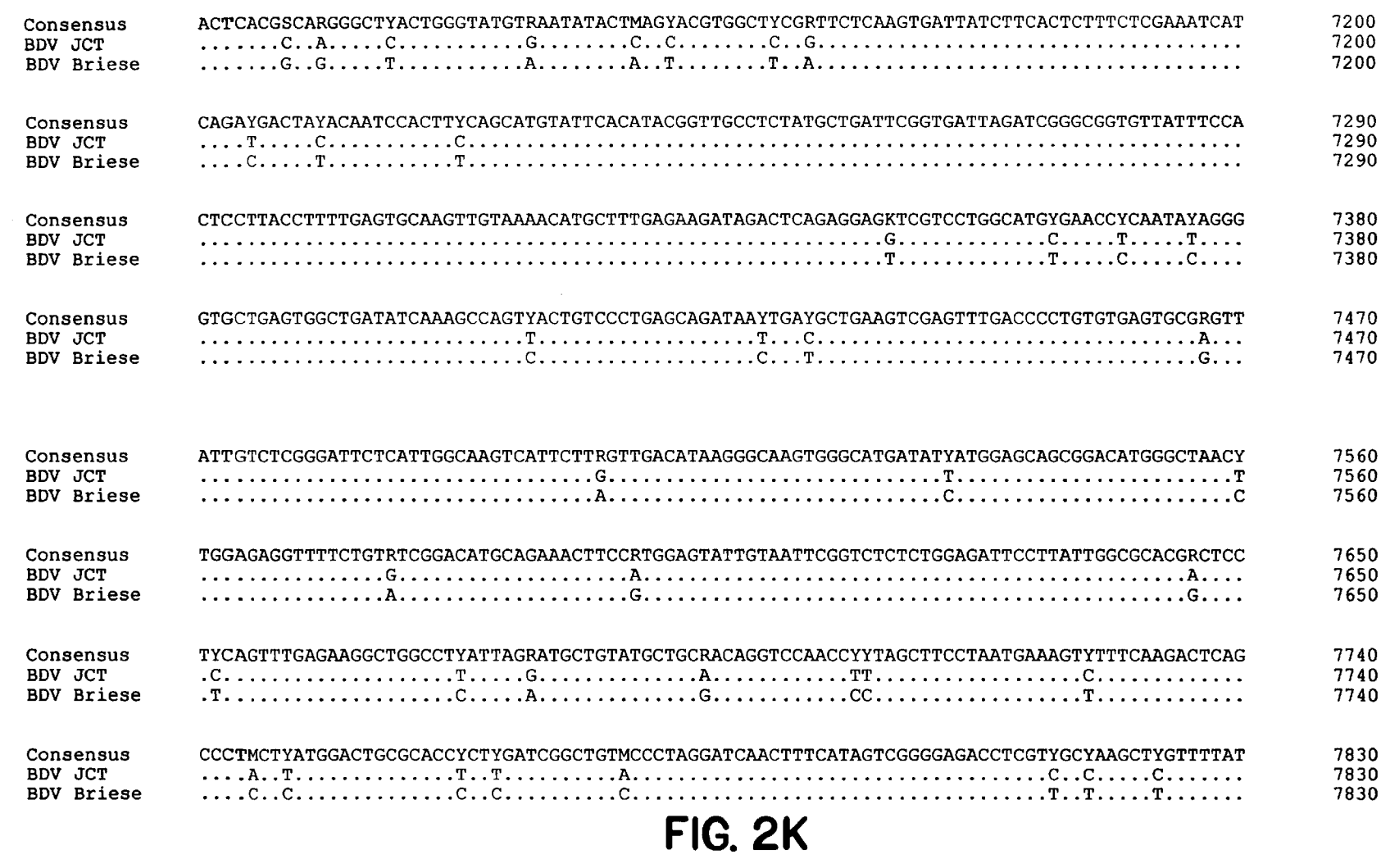
Figure 2L:
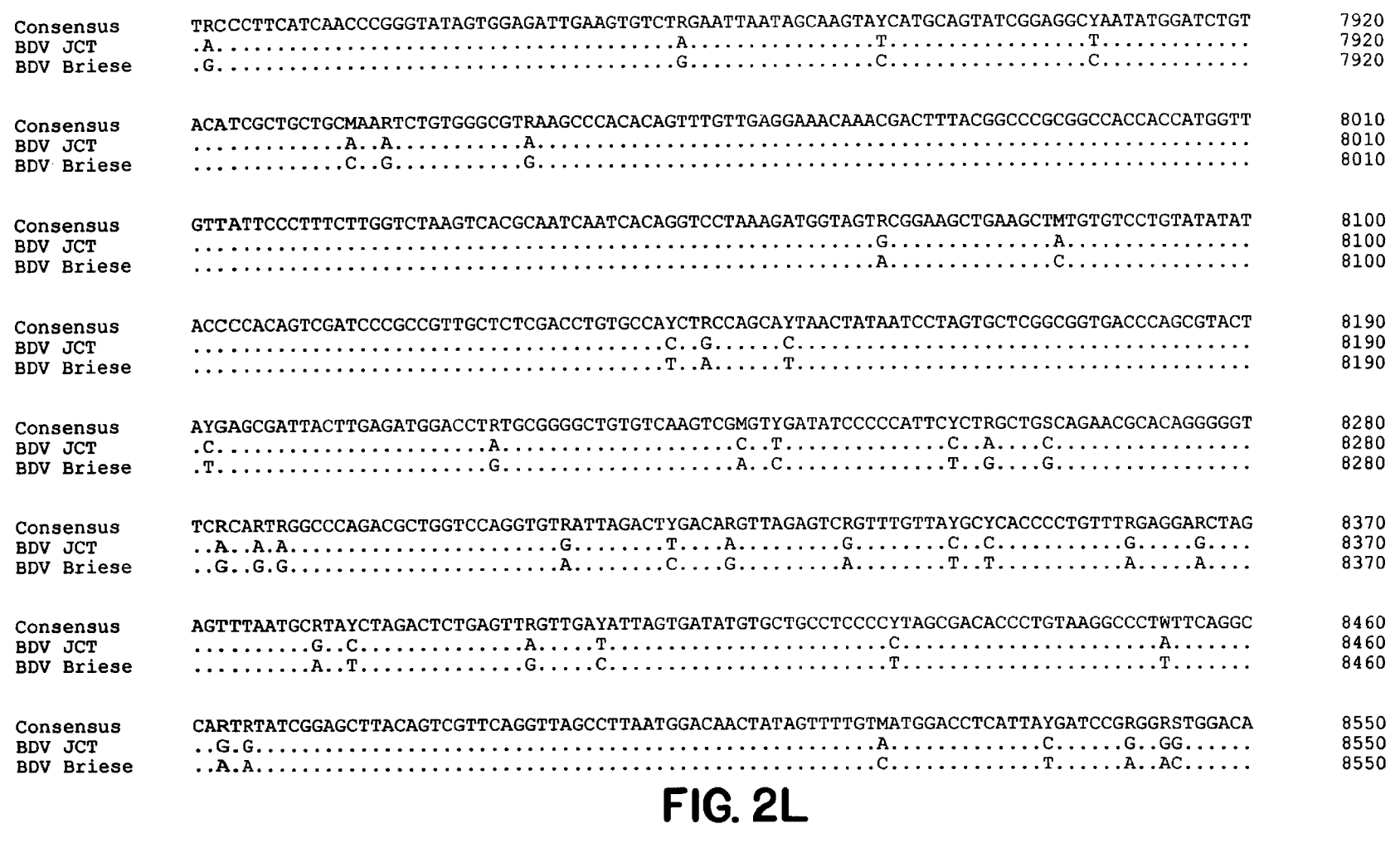

To confirm the identify of the 618 bp PCR amplified BDV p24 ORF fragments resulting from amplification with the 2.1 and 2.2 primer pairs as described above, the resultant fragments were detected by Southern blot hybridization using a $^{32}$P-probe corresponding to an internal p24 fragment (nucleotides 1329 to 1749 in the BDV RNA genome as shown in FIGS. 2C and 2D and SEQ ID NO 1).

Figure 3A:
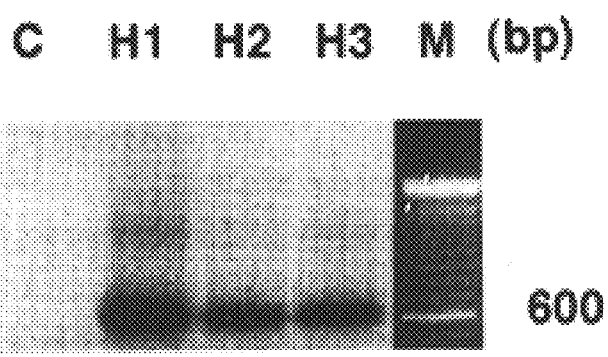
FIGS. 3A and 3B together illustrate the expression of human BDV RNA in PBMC of psychiatric patients. Total RNA (1 to 5 $\mu$g) isolated from PBMC was reverse transcribed by priming with random hexamers and the corresponding cDNAs amplified by PCR as described in Examples 1 and 2 using the following: 1) BDV-specific primers to amplify a 603 bp fragment corresponding to full length BDV p24 ORF including 15 other bp of primer sequences outside the ORF. BDV specificity was determined by southern blot hybridization as shown in FIG. 2A using a BDV-specific probe internal to the predicted PCR product; 2) Specific primers to amplify a 192 bp GAPDH fragment detected by ethidium bromide staining as indicated in FIG. 2B. Samples are: lane 1, PBMC from a representative healthy control individual negative for BDV antigen; lanes 2–4, PBMC from psychiatric patients H1, H2, and H3, respectively.
Figure 3B:
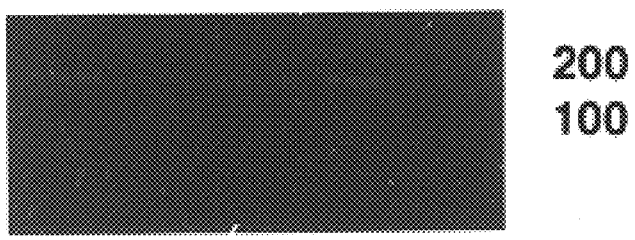

The results of the Southern blot are shown in FIG. 3. The control sample, labeled C in lane 1, is PBMC-isolated RNA, subjected to RT-PCR, from a representative healthy control individual negative for BDV antigen; in lanes 2–4, PBMC-isolated RNA was run from psychiatric patients H1, H2, and H3, respectively. The figure corresponds to a composite of the autoradiographic segment on the top showing the results of southern blot hybridization and the part of the gel on the bottom showing the ethidium bromide staining of GAPDH amplified fragment in the control as well as the patient samples. Track M corresponds to the 1 kb ladder DNA (GIBCO BRL, Gaithersburg, Md.). The top and bottom of the composite were lined up with respect to the migration of the 1 kb ladder DNA (track M).

Treatment of RNA samples with DNase-free RNase, but not with RNase-free DNase prior to the RT-PCR assay, as well as the omission of the reverse transcriptase enzyme, prevented amplification of both BDV p24 and GAPDH sequences.

PCR products from amplifying BDV p16, p40, p56 and the L polymerase are analyzed by Southern blot hybridization as described above for BDV p24.

2) Sequence Characterization of Human BDV Isolates

Both nucleotide and amino acid sequence analysis of the PCR products obtained above confirmed that the infectious agent replicating in OL cells was BDV.

For sequencing, the BDV PCR products prepared above were separately gel purified for subsequent cloning into the pCRII vector through use of the TA cloning system (Invitrogen, San Diego Calif.). Sequencing of the subcloned BDV PCR fragments was done with Sequenase version 2.0 (U.S. Biochemical, Cleveland, Ohio) system according to the manufacturer's instructions. The p24, p16 and p56 ORF sequences respectively presented in FIG. 4A, FIG. 4B and FIG. 4C (a continuous sequence presented on three consecutive sheets) were determined by sequencing of three independent clones obtained from independent PCR events. Only changes found in the three clones for each ORF were considered.

As an internal control for errors introduced by RT and Taq polymerases under the experimental conditions used in the RT-PCR assays, repetitive sequencing was performed of molecular clones derived from reverse transcription and PCR amplification of RNA from a lymphocytic choriomeningitis virus (LCMV) clone highly adapted to its culture environment. For this purpose, RNA was directly isolated from a single plaque of LCMV Armstrong strain, clone 5 3b. This plaque was grown in Vero cells and originated from a LCMV population that had been serially passaged thirty times in Vero cells using for each passage a multiplicity of infection of 0.1 plaque forming units (PFU)/cell. RNA was reversed transcribed using random hexamers as described above and PCR conducted using a pair of primers to specifically amplify a 362 bp fragment of the LCMV glycoprotein following procedures described by Evans et al., *J. Virol.*, 68:7367–7373 (1994). The estimated mutation frequency found was less than $2.5 \times 10^{-4}$ substitutions per nucleotide for Taq polymerase errors, indicating that it is very unlikely that Taq polymerase errors are responsible for the differences found between human BDV isolates and BDV strain V as described below.

Figures 1, 4A:
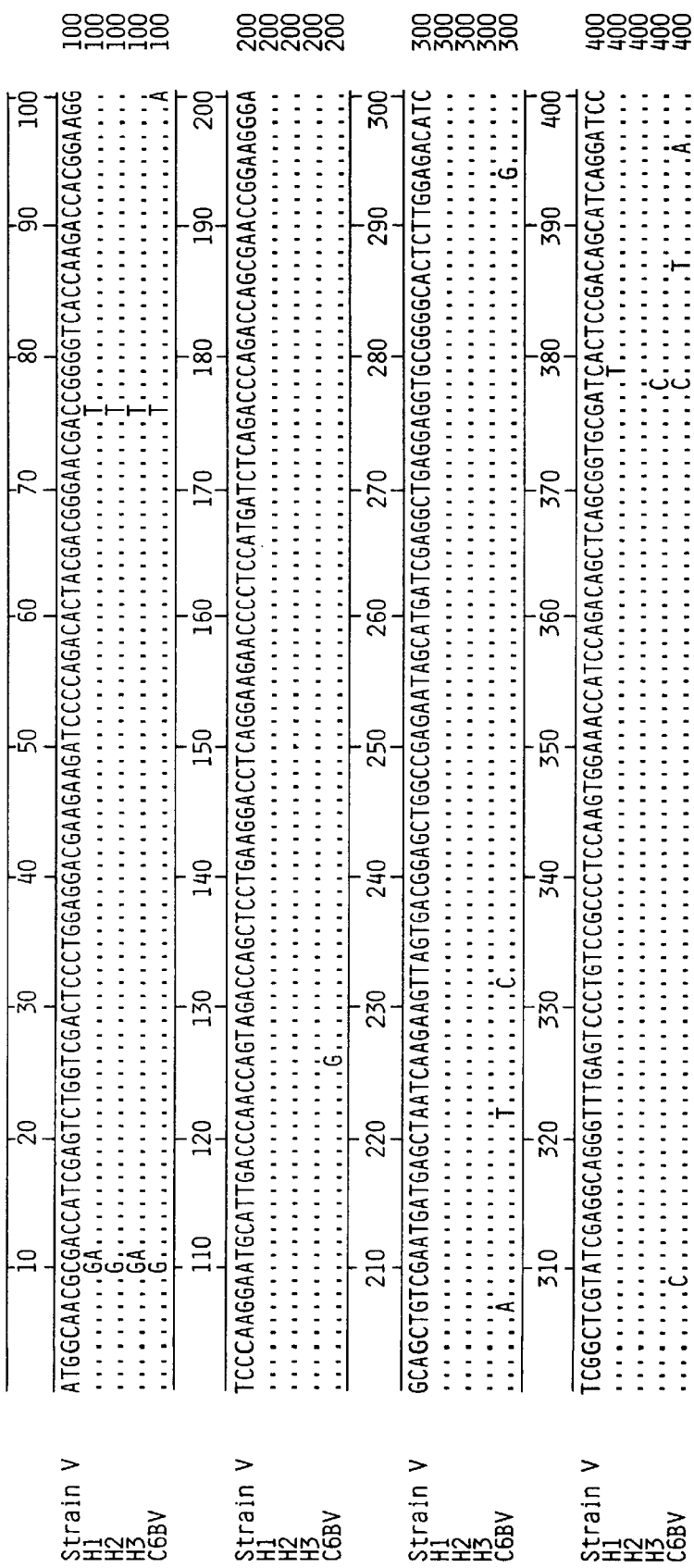
Figure 4B:
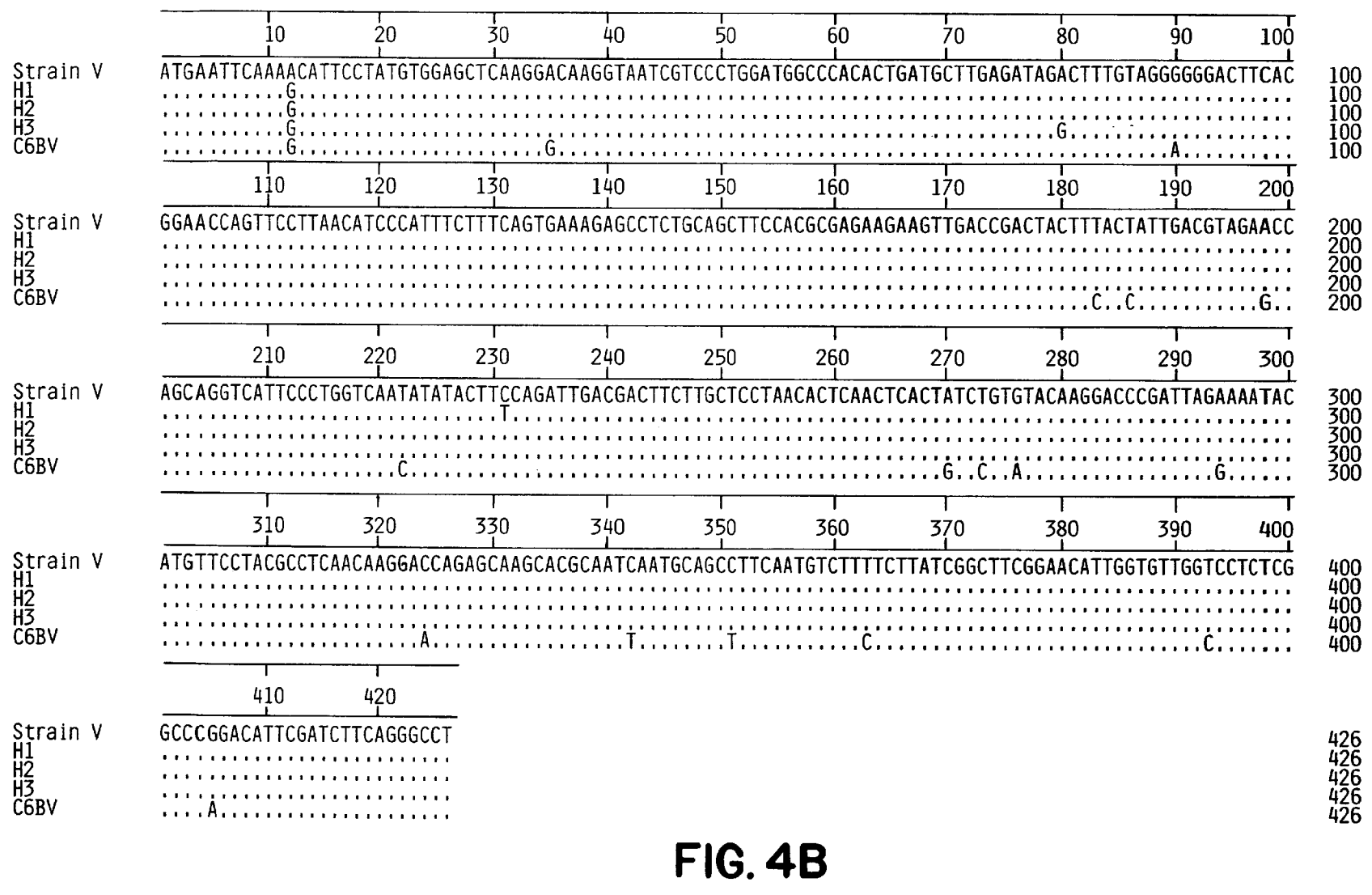
Figures 1, 4C:
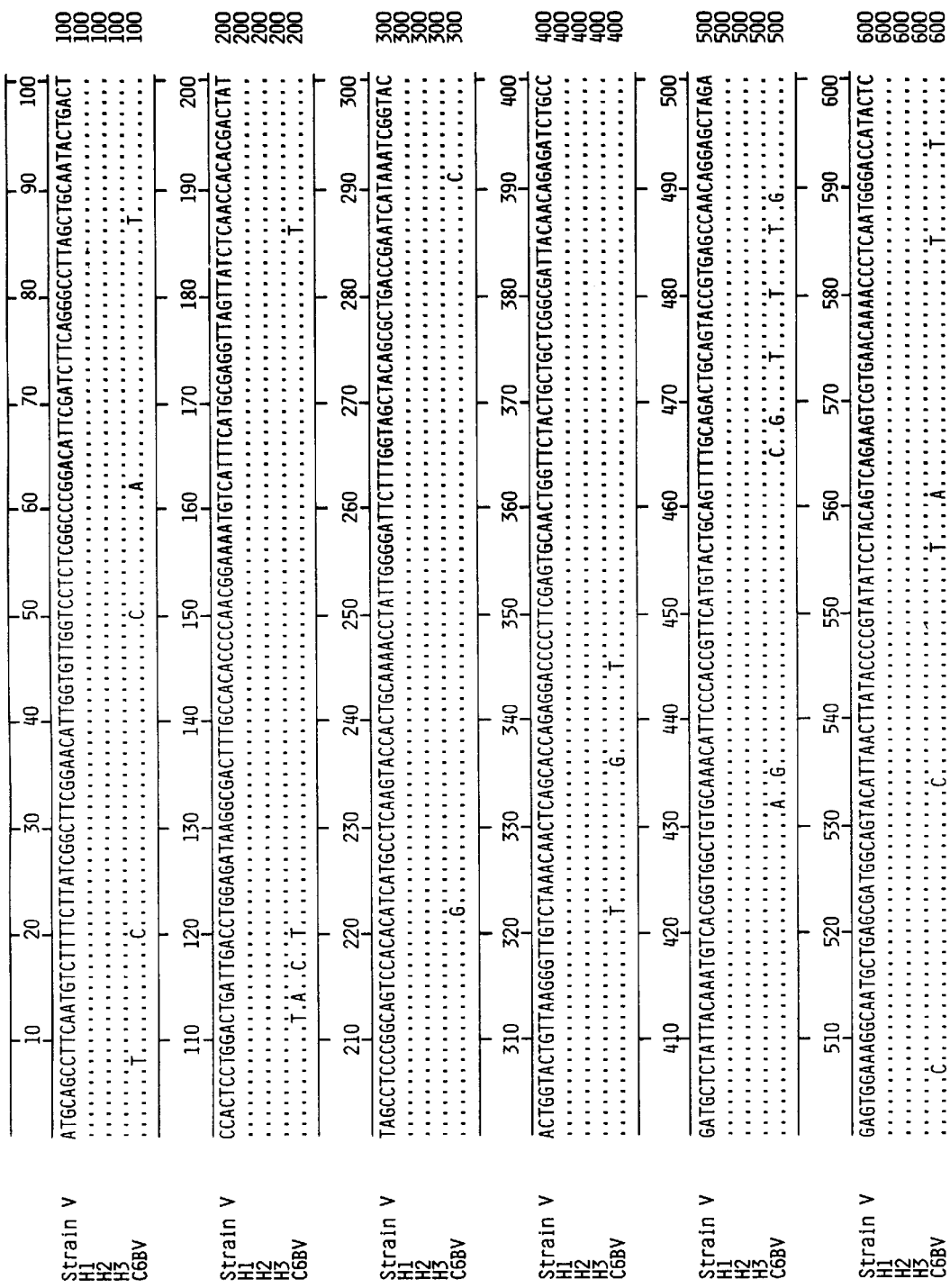

FIGS. 4A–4C show the respective nucleotide sequence alignment of ORFs p24 (4A), p16 (4B) and p56 (4C) among the human BDV isolates (H1, H2, and H3), C6BV and BDV strain V. Dots in each of the figures indicate the same nucleotide as the one found for that position in the BDV strain V sequence. Numbers on the right correspond to last nucleotide position of each row within the corresponding ORF. The complete RNA genome sequences of strain V and C6BV have been published as previously described and have the accession numbers U04608 and L27077, respectively. Corresponding to p24 nucleotide sequences shown in FIG. 4A, the strain V, H1, H2 and H3 sequences are respectively listed as SEQ ID NO 2, SEQ ID NO 3, SEQ ID NO 4 and SEQ ID NO 5. The p24 polypeptides encoded by full-length ORF p24 in the last three SEQ ID NOs are respectively listed in SEQ ID NO 20 (FIG. 8A), SEQ ID NO 21 (FIG. 8B) and SEQ ID NO 22 (FIG. 8C).

Similarly, for the p16 nucleotide sequences shown in FIG. 4B, the strain V, H1, H2 and H3 sequences are respectively listed as SEQ ID NO 6, SEQ ID NO 7, SEQ ID NO 8 and SEQ ID NO 9. The p16 polypeptides encoded by full-length p16 ORF in the last three SEQ ID NOs are respectively listed in SEQ ID NO 23 (FIG. 9A), SEQ ID NO 24 (FIG. 9B) and SEQ ID NO 25 (FIG. 9C).

Moreover, for the p56 nucleotide sequences shown in FIG. 4C, the strain V is listed as SEQ ID NO 10. The is p56 nucleotide sequence for patient H1 is listed as SEQ ID NO 11. As the p56 nucleotide sequences are identical among patients H2 and H3, only one nucleotide sequence is presented for both of them as SEQ ID NO 12. Accordingly, the encoded amino acid residue sequences for patients H1 and H2/H3 are respectively listed in SEQ ID NOs 26 (FIG. 10A) and 27 (FIG. 10B). The respective sequences for C6BV strain are not listed as SEQ ID NO.

Figures 2, 4C:
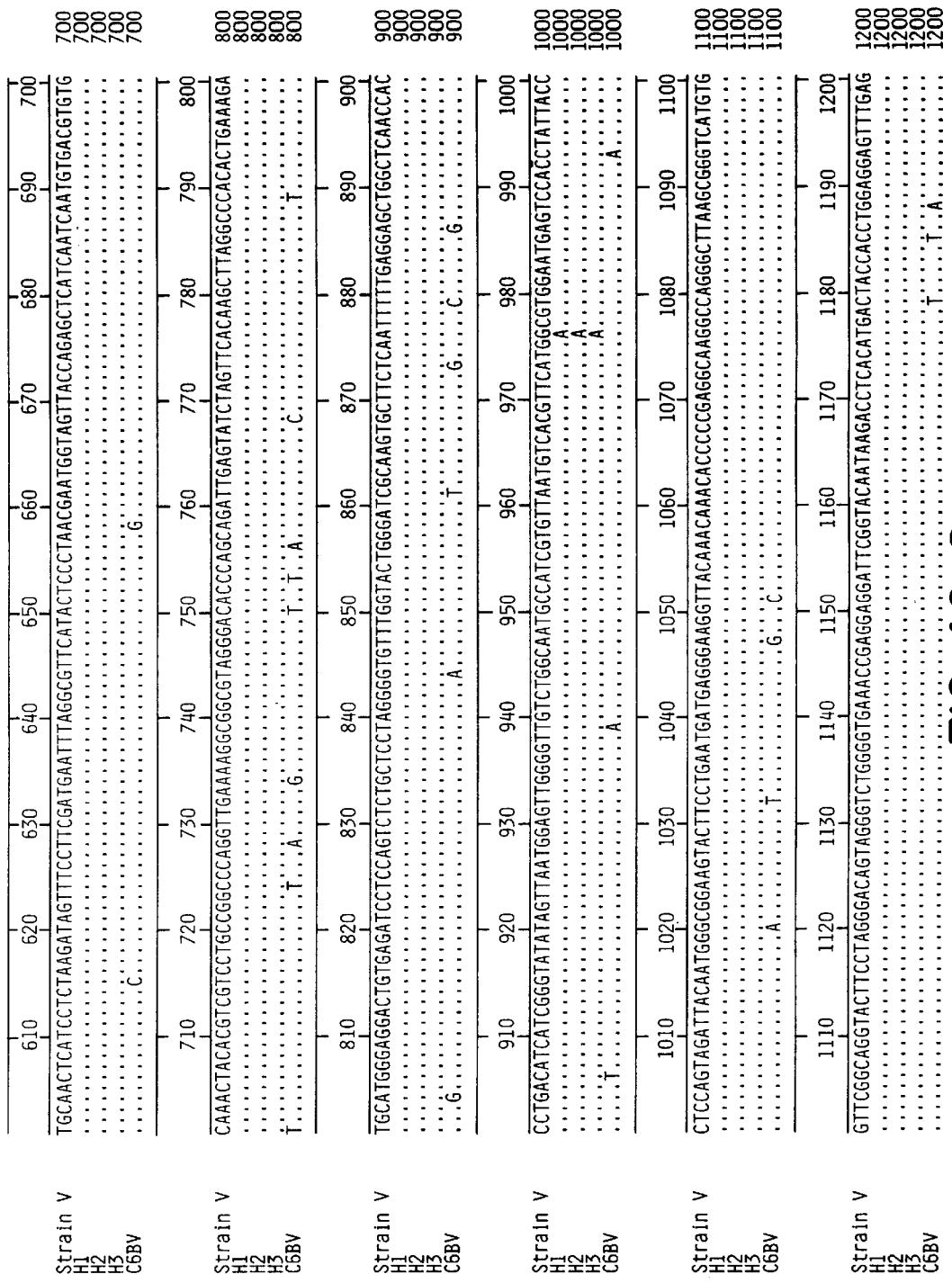
Figure 5A-1:
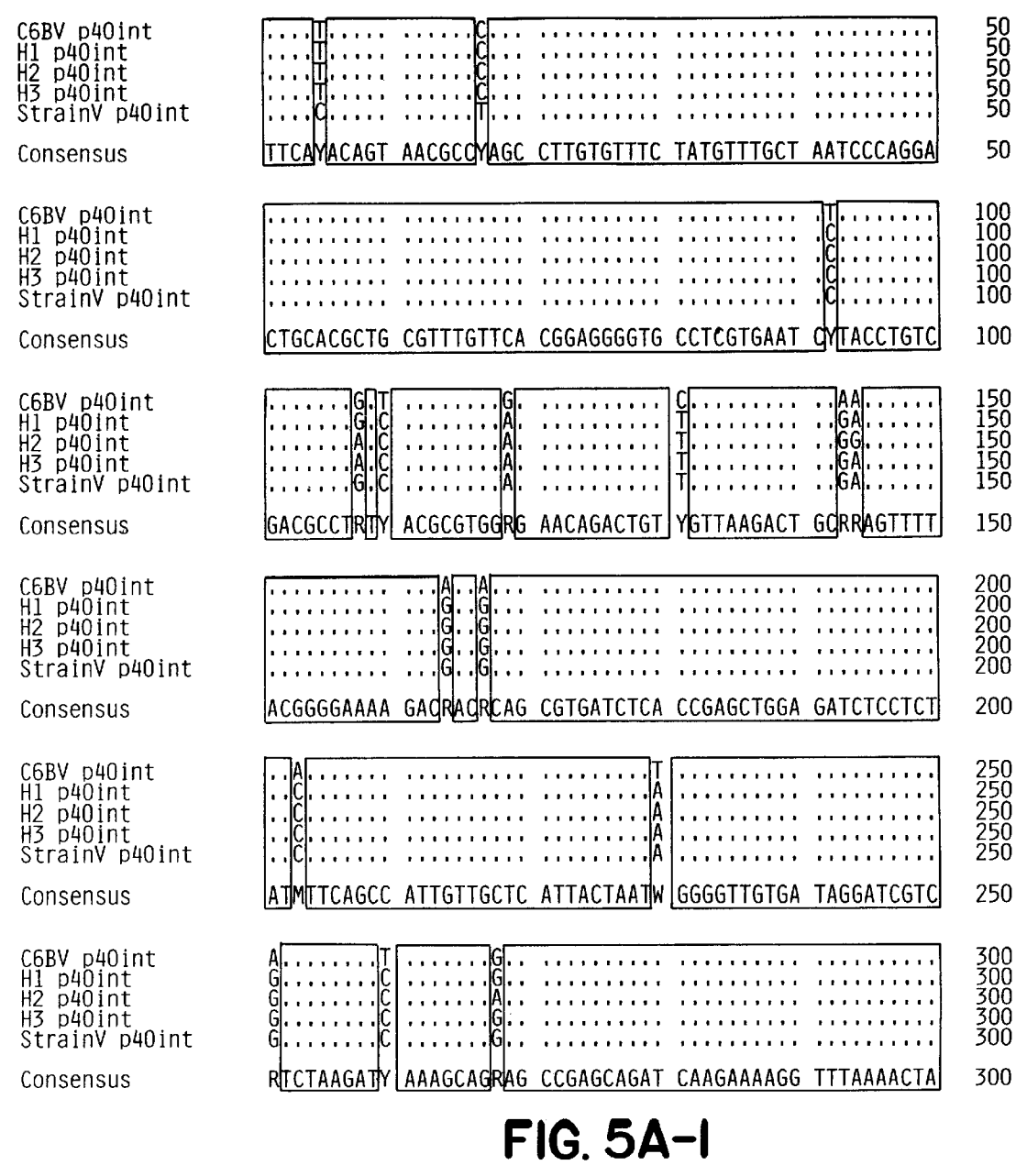

Partial p40 nucleotide sequences having 571 nt for patients H1, H2 and H3 are shown in FIGS. 5A-1 and 5A-2 as compared to the corresponding regions in C6BV and Strain V, along with a consensus sequence. The nucleotide alignments are as previously described. The 571 nt region corresponds to the region amplified by the first primer pair indicated above while a 528 nt region results from nested PCR as previously described. The p40 consensus sequence is listed as SEQ ID NO 13. The H1, H2 and H3 patient sequences are respectively listed as SEQ ID NO 13, SEQ ID NO 14 and SEQ ID NO 15. The corresponding respective encoded human BDV p40 full-length polypeptides are listed in SEQ ID NO 28 (FIG. 11A), SEQ ID NO 29 (FIG. 11B) and SEQ ID NO 30 (FIG. 11C).

Partial catalytic domain of the L polymerase nucleotide sequences having 689 nt for patients H1, H2 and H3 are shown in FIGS. 5B-1 through 5B-3 as compared to the corresponding regions in C6BV and Strain V. A consensus sequence for this domain is also shown and is listed as SEQ ID NO 17. Patient H1 and H2 sequences are identical and listed as SEQ ID NO 18 while H3 having one nucleotide difference is listed as SEQ ID NO 19. However, the nucleotide difference does not result in an alteration of encoded amino acids. Thus, all three patients have the same encoded catalytic domain encoded polypeptide sequence listed in SEQ ID NO 31 (FIG. 31).

Direct cloning and sequencing of BDV ORFs p24 and p16 present in the patients' PBMC revealed that the p16 sequence determined directly from RNA isolated from PBMC of each of the three patients (H1, H2, and H3), was identical to the corresponding p16 sequences obtained from RNA isolated from OL cells after co-cultivation with patient PBMC. p24 sequences determined prior and after co-cultivation of patients' PBMC with OL cells were also identical in patients H1 and H2, whereas in the case of patient H3, one single nucleotide silent change (C→T) was found in the third base position of codon 127.

OL cells co-cultivated with PBMCs from patients H1, H2, and H3, but not from healthy controls, expressed BDV-specific RNAs. Sequence analysis of RT-PCR products obtained using RNA from OL cells co-cultivated with patients' PBMCs and specific primers to amplify BDV ORFs p24, p16, p56, and the catalytic domain of the L polymerase, unequivocally identified these isolates as human BDV.

The three human BDV isolates showed a high degree of sequence conservation with respect to BDV strain V and C6BV genome sequences, as well as BDV sequences determined in samples from naturally infected animals of different species. BDV strain V and C6BV sequences had more than 95% homology at the nucleotide level (Briese et al., *Proc. Natl. Acad. Sci. USA*, 91:4382–4386 (1994); Cubitt et al., *J. Virol.*, 68:1382–1396 (1994)), which is remarkably high for two RNA virus isolates with different origin and passage history (Holland, *Curr. Top. Microbiol. Immunol.*, 176 (1992); Morse, ed. "The Evolutionary Biology of Viruses", Raven, New York (1994)). Both viruses, BDV strain V and C6BV were originally isolated from two different naturally infected horse brains and passed several times in rabbits, followed by passages in rats (Schneider et al., *J. Virol.*, 68:63–68 (1994)). In addition, both viruses were maintained as a persistent infection for more than twenty passages either in OL cells, in the case of BDV strain V, or in the rat astrocytoma C6 cells for C6BV, before their corresponding genome sequences were determined.

Each of the three human BDV isolates of this invention had an unique sequence, differing from the other two at one or two nucleotide positions in each of the ORFs analyzed here, with the exception of identical p56 sequences found for H2 and H3 (FIG. 4C) and the catalytic domain for H1 and H2 (FIGS. 5B-1 through 5B-3), where in the latter, the nucleotide change was present in the 3' primer sequence. Levels of divergence between the human BDV isolates and C6BV at the nucleotide level were similar to those found for p24 sequences between BDV isolates from horses separated by more than ten years and with different history of passages in tissue culture. Moreover, high nucleotide sequence conservation, with only 0.3% divergency, has been also reported among p24 BDV sequences from naturally infected horses and sheep (Binz et al., *Virus Res.*, 34:281–289 (1994)). The human BDV isolates displayed a high level of sequence conservation with respect to BDV strain V, with divergencies of 0.5% to 0.83% for p24, 0.23% to 0.47% for p16, and 0.07% to 0.20% for p56 (FIG. 6B as futher described below). In addition, cloning and sequencing of the segment of BDV ORF V corresponding to the putative catalytic domain of the viral L polymerase, revealed a complete amino acid conservation between the three human BDV isolates and BDV strain V not including the region corresponding to the 3' primer.

No insertions or deletions were observed in p24, p16 and p56 ORPs sequences of the human BDV isolates compared to the corresponding reported sequences for BDV strain V and C6BV. When compared to C6BV, most of the nucleotide changes in human BDV isolates were transition events, accounting for 92.8 to 93.7%, 93.7 to 94.1%, and 87 to 88% of the substitutions found in p24, p16, and p56, respectively. Mutations in p24, p16 and p56 ORFs were randomly distributed with not apparent regions of higher variability.

The nature and total number of amino substitutions, as well as total number of nucleotide differences, in ORFs p24, p16 and p56 among the human BDV isolates and the horse-derived strain V and C6BV isolates are summarized in FIG. 6A and FIG. 6B.

In FIG. 6A, the amino acid differences found in ORFs p24, p16 and p56 among the three human BDV isolates (H1, H2, and H3), C6BV and strain V are presented. Amino acids are presented in the single letter code. Numbers on top correspond to the codon position within each ORF. The dashes indicate correspondence to the C6BV amino acid at the particular amino acid positions. FIG. 6B shows a triangular matrix summarizing the total number of nucleotide (upper right) and amino acid (lower left) substitutions among the BDV human isolates (H1, H2, and H3), C6BV and strain V.

All three human BDV isolates had the substitution Ala→Thr at amino acid position 326 in p56 compared with C6BV and BDV strain. The H1 isolate also had two amino acids, Thr and Leu at positions 412 and 501, respectively, in p56, that are not found in C6BV or BDV strain V sequences. Isolates H1 and H3 had Glu at position 4 in p24, an amino acid not previously seen at this position in any of the BDV p24 sequences as yet reported in other species. In addition, isolate H1 had Thr at position 127 in p24, instead of the H1 found in all the other BDV p24 sequences as yet determined.

The possibility that the OL cells became BDV positive as result of a contamination with BDV from laboratory sources can be excluded because of the following: 1) Co-cultivation experiments and later passages of the infected cells were conducted in a tissue culture facility where V-infected material had never been previously used; 2) PBMC samples were coded and the investigators conducting tissue culture work operated in a double-blind manner and in ten independent control experiments OL cells co-cultivated with BDV-antigen negative PBMC samples did not express BDV antigen and RNA after more than 30 passages; 3) Sequence data indicated that each of the three human BDV isolates are genetically more closely related to BDV strain V than C6BV and RT-PCR assays, cloning of amplified products and sequence determination were conducted where BDV strain V had not been previously handled; 4) Changes in p24 and p16 BDV strain V sequences were not found after more than twenty passages in OL cells. This finding likely reflects the adaptation in the laboratory of BDV strain V to grow in OL cells. In contrast, each of the human BDV isolates recovered by co-cultivation of patients' PBMC with OL cells, differed from the other two BDV human isolates and from BDV strain V in their p24 and p16 sequences (FIG. 4A and 4B); and 5) Direct cloning and sequencing of BDV ORFs p24 and p16 present in the patients' PBMC, without amplification through co-cultivation with OL cells revealed that p24 and p16 sequences present in PBMC of patients H1 and H2 were identical to the p24 and p16 sequences determined after co-cultivation of the corresponding PBMC with OL cells. In the case of patient H3, comparison of sequences derived directly from PBMC and after co-cultivation with OL cells showed no differences in p16 and one single silent nucleotide change in p24, corresponding to the transition C→T in is the third base of codon 127. This result also suggests sequence stability during BDV replication in OL cells.

Because the mutation frequencies of RNA viruses exceed, by more than a millionfold, those of their eukaryotic hosts, extremely rapid virus evolution is anticipated and frequently observed. However, RNA viruses can also exhibit long-term stasis both in nature and in laboratory experiments as result of selection for fit master sequences in rather constant environments. Although only limited sequence information is presently available, the data presented herein for the first time indicate a high level of sequence conservation among BDV isolates and BDV polypeptide-encoding regions from PBMC of the three psychiatric patients and from naturally infected field animals of different species. This finding suggests that BDV strain V-like sequences may represent prevalent and stable species of BDV in nature, with the ability to infect a number of different animal species including humans. It is worth noting that frequently one single, or very few, amino acid changes can cause drastic phenotypic changes in RNA viruses, including altered tropism and pathogenicity. Furthermore, the host's genetics also contributes to disease phenotypes caused by BDV infection.

This invention thus provides direct evidence of BDV infection in humans and a method for screening for such as described herein for both nucleic acids and proteins including BDV antigens and antibodies.

C. Analysis of BDV mRNA

Figure 7A:
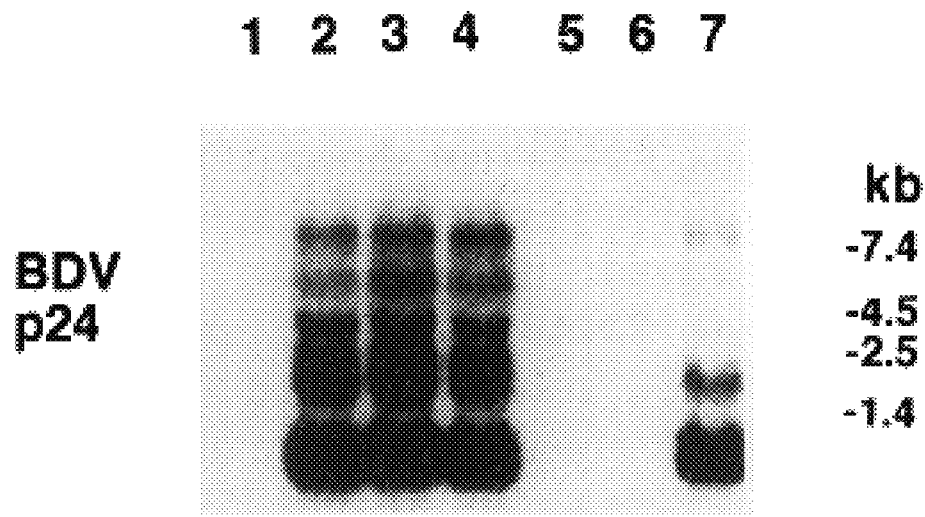
FIG. 7A illustrates the expression of BDV RNA in OL cells infected by co-cultivation with PBMC from psychiatric patients. Total RNA (10 μg) from each sample was analyzed by Northern blot hybridization using specific probes for BDV p24 and GAPDH, respectively shown in FIG. 7A and FIG. 7B. Lanes 1 and 5 correspond to RNA from OL cells infected with PBMC from two representative healthy control individuals negative for BDV antigen; lanes 2–4 correspond to RNA from OL cells infected with PBMC from patients H1, H2,and H3,respectively. RNA from C6 (lane 6) and C6BV (lane 7) cells, were used as negative and positive controls, respectively, of BDV hybridization.
Figure 7B:
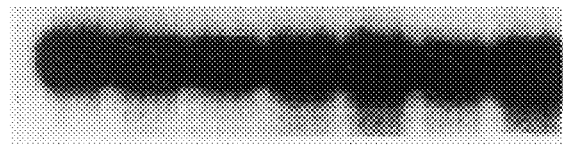
FIG. 7C shows the ethidium bromide staining of the RNA gel.
Figure 7C:
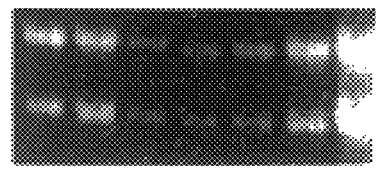

BDV persistent infection in a variety of cultured cells is characterized by the absence of cytolysis and lack of cell-free virus production, but relative high levels of viral RNA transcription and replication (de la Torre et al., *Virol.*, 179:853–856 (1990)). Northern blot hybridization studies revealed that RNA isolated from OL cells co-cultivated with the PBMC of patients H1, H2, and H3 displayed the expected pattern of BDV-specific transcripts detectable with a BDV p24 probe (Cubitt et al., *J. Virol.*, 68:1382–1396 (1994) as shown in FIG. 7.

For the Northern analysis, total RNA (10 μg) from each sample was analyzed by hybridization using specific probes for BDV p24 and GAPDH as respectively shown in the upper and middle portions of the figure. Lanes 1 and 5 correspond to RNA from OL cells infected with PBMC from two representative healthy control individuals negative for BDV antigen; lanes 2–4, correspond to RNA from OL cells co-cultured with PBMC from patients H1, H2, and H3, respectively. RNA from C6 (lane 6) and C6BV (lane 7) cells, were used as negative and positive controls, respectively, of BDV hybridization. The lower part of the figure shows the ethidium bromide staining of the RNA gel.

OL cells co-cultivated with PBMC from healthy control volunteers expressed neither viral antigens nor BDV-specific RNAs after more than twenty passages as shown in lanes 1 and 5. These results indicated that infectious BDV, with the ability to replicate in OL cells, was present in PBMC from patients H1, H2, and H3.

D. Detection of Patient-Derived BDV Antibodies

1) Preparation of Synthetic BDV Peptides

The synthetic BDV peptides used in practicing the methods of this invention are synthesized using standard solid-phase synthesis techniques as, for example, described by Merrifield, *Adv. Enzymol.,* 32:221–296 (1969), and Fields, G. B. and Noble, R. L., *Int. J. Peptide Protein Res.,* 35:161–214 (1990) or for example, by the simultaneous multiple peptide synthesis method using the solid-phase technique described by Houghten, *Proc. Natl. Acad. Sci. USA,* 82:5131–5135 (1985). The synthesized peptides are then analyzed by reverse phase high performance liquid chromatography (HPLC) on a Vydac C-18 column (Alltech Associates, Inc., Ill.) with a 0–60% acetonitrile linear gradient in 0.1% trifluoroacetic acid. Peptides are then purified to homogeneity by preparative HPCL using optimal conditions suggested by the analytical chromatography. Amino acid compositions and concentrations of isolated peptides are determined by subjection to 24 hour hydrolysis in 6 N HCl in evacuated tubes at 110 degrees Celsius (110° C.) and subsequent analysis on a Beckman Model 6300 High Performance Analyzer.

Purified peptides are separately resuspended in distilled water to form a dissolved peptide solution.

The amino acid residue sequences of BDV peptides listed in Table 3 are derived from the amino acid sequences of BDV p40, p24, p16 and p56 antigens. The selection of BDV peptide sequences, as well as the immunization of animals using these peptides, is as described in "Peptides as Immunogens", in Current Topics in Microbiology and Immunology, Vol. 130, Koprowski and Melcher (eds), Springer-Verlag, Berlin, Heidelberg (1986).

TABLE 3

| Peptide Designation | SEQ ID NO | Amino Acid Sequence* |
|---|---|---|
| p24-1 | 32 | MATGPSSLVDSLEDEEDP |
| p24-2 | 33 | RIYPQLPSAPTADEWDIIP |
| p16-1 | 34 | MNSKHSYVELKGKVIVPG |
| p16-2 | 35 | RLRNIGVGPLGPDIRSSGP |
| p56-1 | 36 | GLSCNTDSTPGLIDLEIR |
| p56-2 | 37 | RSKLRRRRRDTQQIEYLV |
| p56-3 | 38 | LISLCVSLPASFARRRRLGRWQE |
| p40-1 | 39 | MPPKRRLVDDADAMEDQD |
| p40-2 | 40 | MEDQDDLYEPPASLPKLP |
| p40-3 | 41 | ELSGEISAIMRMIGVTGLV |

*Amino acid sequence written in single letter code

The resultant peptides are then used in the methods of this invention to determine the presence of BDV antibody in a subject as well as be used as immunogens to raise anti-peptide polyclonal and monoclonal antibodies as described below.

2) Preparation of Recombinant BDV Peptides BDV p40, p24 and p16 recombinant peptides were expressed as trpE-fusion proteins in *E. coli* BL21/DE3 cells (Studier and Moffat, *J. Mol. Biol.,* 189:113–130 (1986), for use in the pATH vector system (Korner et al., *Methods Enzymol.,* 194:477–490 (1991). An amino-terminal 826 bp fragment of the BDV p40 gene was excised with XbaI/HindIII from the pCRII vector containing the subcloned p40 gene, referred to as PCRII-p40, prepared as described in Example 2B. The excised p40 gene was then ligated into a similarly digested pATH2 vector (ATCC Accession Number 37696). The complete p24 ORF was excised with EcoRI from the pCRII vector containing the p24 ORF as prepared in Example 2B. The resultant p24 gene was then ligated into a similarly digested pATH1 vector (ATCC Accession Number 37695). XmaI-digested PCR-amplified DNA corresponding to full length p16 ORF was inserted into a similarly digested pATH2 vector.

A p56-encoding fragment corresponding to full-length p56 cDNA was obtained by PCR using primers BV2225F (5'CGAATTCGCACGCAATTAATGCAGC3' (SEQ ID NO 56) and BV3738R (5'GCTACTCGAGCGGTACGGTTTATTCCTGC3' (SEQ ID NO 57). With the exception that restriction cloning sites for facilitating directional cloning into the multiple cloning site of the pCRII vector rather than using the TA cloning region were used with the above primer pairs, the resulting amplified fragment was cloned into pCRII as previously described. In addition, a truncated form of p56 cDNA was prepared to generate as a trpE fusion protein in the pATH2 vector system where the p56 portion begins at a methionine residue located at amino acid residue position 150 of the p56 full-length protein. To generate the truncated cDNA, 5' and 3' primers were used in PCR having the respective sequences 5'CCCCCCGGGCAATGTACTG-CAGTTTCGCGGACT3' (SEQ ID NO 58) and 5'GGGC-CCGGGTTATTCCTGCCACCGGCCGA3' (SEQ ID NO 59).

The resultant pATH vectors containing BDV genes were then used in the bacterial expression system for generating trpE recombinant BDV fusion proteins, the expression of which was performed as described by Korner et al., *Methods Enzymol.,* 194:477–490 (1991). Protein extracts from bacteria expressing the trpE-BDV fusion proteins were then separated by SDS-PAGE. The electrophoresed recombinant proteins were then recovered from the gel using 50 mM $NH_4HCO_3$, 3% β-mercaptoethanol as an elution buffer. Recombinant catalytic domain proteins are similarly prepared as described above.

In an alternative approach to generate recombinant BDV proteins for use in the methods of this invention, BDV genes were amplified by PCR from the respective cDNAs for use in a Baculovirus expression vector system. The 5' and 3' primer pairs used in amplifying p40 had the respective nucleotide sequences 5'ATGCCACCCGGGAGACGCCTGATTGAT3' (SEQ ID NO 60) and 5'CGGATCCCGGGCTAGTTTAGACCAGTCACTCC3' (SEQ ID NO 61). The 5' and 3' primer pairs used in amplifying p24 had the respective nucleotide sequences 5'GGCCATATGCGCCCGGGCCCATCGAGTCTGGTCGACTCCCTG3' (SEQ ID NO 62) and 5'CTCGAGCCCGGGTTATGGTATGATGTCCCACTCATC3' (SEQ ID NO 63). The 5' and 3' primer pairs used in amplifying p16 have the respective nucleotide sequences 5'CGAATCCCCGGGAATTCAAAGCATTCCTA3' (SEQ ID NO 64) and 5'TCCCCCCGGGCAGTATTGCAACTAACGG3' (SEQ ID NO 65). Amplification procedures of p56 and the catalytic domain are similarly performed.

Underlined nucleotides in the above primers indicate BDV specific sequences. The resultant amplified DNA fragments were then digested with XmaI and separately ligated into similarly digested Baculovirus transfer vectors, pAC409 (p40 and p16) and pAC401 (p24) (Summers and Smith, "A Manual of Methods for Baculovirus and Insect Cell Culture Procedures", Texas Agricultural Experimental Station, Bulletin 1555, College Station, Tex.

Recombinant baculoviruses were then generated by cotransfection of SF158 (*Spodoptera frugiperda*) insect cels with the respective recombinant baculovirus transfer vectors and linearized BaculoGold DNA (Pharmingen, La Jolla, Calif.) as a source of baculovirus DNA using lipofection as described by Groebe et al., *Nuc. Acids Res.*, 18:4033 (1990). SF158 cells were maintained in TC100 medium supplemented with penicillin (40 IU/ml) and streptomycin (50 μg/ml). The expression of the different recombinant proteins in insect cells was verified by Western blot using polyclonal rabbit antisera for each protein that is prepared as described below.

The resultant recombinant BDV proteins were then used as immunogens to prepare anti-BDV antibodies (see Example 2E) and are separately used in assays to allow the detection of BDV antigens in an individual as described below.

3) Detection of Patient-Derived BDV Antibodies

With the synthetic BDV peptides as described above, BDV antibodies in sera from an individual are detected with immunological based methods, including ELISA as described in International Publication WO/21020, the disclosures of which are hereby incorporated by reference, Western blot, and the like procedures.

BDV antibodies present in an individual are also detected by using the purified recombinant BDV bacterial-expressed proteins prepared above or with lysates of the recombinant BDV eucaryotic-expressed (insect cells). For either, the proteins are separated by 12.5 or 15% SDS-PAGE performed as described by Grasser et al., *J. Virol.,* 65:3779–3788 (1991). After electrophoretic transfer onto a nitrocellulose membrane, the membrane is preincubated at 25° C. for 30 minutes in blocking solution (5% nonfat dry milk in PBS). The blocked membrane is then exposed overnight at 4° C. to selected test sera diluted 1:20 in blocking solution or with rabbit antisera diluted 1:100 (also used for testing antibody titers and specificity). Membranes are then washed three times in PBS, incubated for 1 hour at 25° C. with the appropriate secondary antibody labeled with horseradish peroxidase and diluted 1:500 in blocking solution. After washing three times with PBS, bound antibodies are visualized with diaminobenzidine in hydrogen peroxide or by the enhanced chemiluminescence method with the ECL kit (Amersham Buchler, Braunschweig, Germany).

For competition experiments, approximately $10^7$ baculovirus-infected SF158 cells are washed twice with ice-cold PBS and resuspended in 1 ml of lysis buffer containing 100 mM Tris-HCl, pH 9.0, 100 mM NaCl, 5 mM KCl, 0.5 mM $MgCl_2$, 1 mM $CaCl_2$, 1 mM DTT, 0.5% Triton X-100, 1 mM PMSF and 50 μM leupeptin. After 15 minutes on ice, debris is pelleted and 300 μl of clarified supernatant is added to 100 μl of test sera and maintained for 8–10 hours at 4° C. prior to adding to the electrophoresed BDV proteins for processing as described above.

E. Analysis of BDV Antigens

1) Preparation of Polyclonal Antisera to Synthetic and Recombinant Polypeptides

For preparation of a peptide immunogen, the synthetic and recombinant polypeptides are prepared as described above.

The proteins (25–50 μg) are then separately emulsified in 1 ml of PBS and 1 ml of complete or incomplete Fruend's adjuvant (DIFCO Laboratories, Detroit, Mich.) to prepare immunogens. For each BDV protein, two rabbits as well as two rats are immunized by intradermal injection and subsequently boosted subcutaneously at three-week intervals with 25–50 μg of immunogen in Freund's incomplete adjuvant. Rats are used as rat anti-BDV antibodies have been known to have lower background of non-specificity. Moreover, rat spleens from immunoresponsive rats are then used to generate monoclonal antibodies as described below.

Blood is then collected three times during week 3 and 14 and the serum analyzed for the presence of BDV-specific antibodies by Western blot or by ELISA performed as described by Budleston et al., *Aids Res. Human Retrovirus,* 9:939–944 (1993) or in International Publication WO/21020. Further specificity and antibody-binding characteristics are then assessed with immunofluorescence analyses and immunoprecipitation procedures using COS-7 cells transfected with the corresponding BDV ORF under control of a cytomegalovirus immediate early promoter (pRc/CMV-BDV). With the latter system, good levels of expression of BDV ORFs as determined with immunofluorescence has been detected with serum from a BDV-infected rat.

Anti-p56 antibodies to truncated p56 recombinant protein prepared as described in Example 2D were obtained with the above-described methods for use in the present invention.

Immunospecific peptide antibodies are then further purified by ammonium-sulfate precipitation (0–45%), followed by purification of IgG on an ion-exchange Mono Q column (Pharmacia LKB, Piscataway, N.J.) connected to a fast protein liquid chromatography (FPLC) system (Pharmacia). Purified anti-peptide polyclonal antibodies are then used in assays for detecting BDV antigens in patient samples as described below.

2) Preparation of Monoclonal Antibodies

The peptide and recombinant protein immunogens prepared above are also used to generate monoclonal antibodies in rats. The immunogens are separately injected into rats as described above with a boost of 50 μg of the prepared peptide intravenously (i.v.) in normal saline 4 days prior to fusion and a second similar perfusion boost one day later.

The animals so treated are sacrificed and the spleen of each mouse is harvested. A spleen cell suspension is then prepared from which spleen cells are isolated and used to prepare hybridomas according to the methods well known to one of ordinary skill in the art.

The resultant anti-BDV peptide hybridomas are then screened for immunoreactivity as described above. Selected positive clones are then subcloned and used for detecting BDV antigens in patient samples as described below.

3) Detection of BDV-Specific Antigens

BDV-specific antigens were detected in cells expressing BDV-specific RNAs as determined by indirect immunofluorescence as described by Cubitt et al., *J. Virol.,* 68:1371–1381 (1994). Briefly, cells were washed once with PBS and fixed in acetone/methanol for 5 minutes at room temperature. After several washes, the fixed cells were then incubated in PBS containing 5% normal goat serum for 45 minutes at room temperature to block non-specific background. Cells were then incubated with the following antibodies: 1) BP-11, a serum from an experimentally BDV-infected splenectomized rabbit; 2) L149, a cerebrospinal fluid (CSF) sample isolated from a horse with BDV; 3) KFU2 and WI monoclonal antibodies that specifically recognize p24 and p40 BDV antigens, respectively. In other assays, the anti-peptide antibodies of this invention along with anti-BDV p24, p16, p56, p40 and the catalytic domain recombinant proteins produced as described above, are used in the above-described method to detect BDV antigens present in PMBC isolated from suspected BDV-infected subjects.

After incubation with the primary antibodies for 60 minutes at room temperature, exposed cells are washed five times with PBS and reacted with the corresponding fluorescein isothiocyanate-conjugated secondary antibodies to allow detection of immunoreaction product.

BDV antigens are also detected by flow cytometry performed as described by Bode et al., Nature Med., 1:232–236 (1995). Briefly, patient PBMC are first fixed with paraformaldehyde (2.5% for 30 minutes) and treated with Triton X-100 (1% for 45 minutes). BDV antigens are detected with the above-described antibodies and fluorescently labeled secondary antibodies.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A method of detecting a Borna disease virus (BDV) nucleic acid in a sample, the method comprising:

a) hybridizing the nucleic acid in the sample with a probe consisting of a polynucleotide sequence encoding a human BDV polypeptide selected from the group of amino acid residue sequences consisting of MATGPSSLVDSLEDEEDP (SEQ ID NO 32), RIYPQLPSAPTADEWDIIP (SEQ ID NO 33), MNSKHSYVELKGKVIVPG (SEQ ID NO 34), RLRNIGVGPLGPDIRSSGP (SEQ ID NO 35), GLSCNTDSTPGLIDLEIR (SEQ ID NO 36), RSKLRRRRRDTQQIEYLV (SEQ ID NO 37), LIS-LCVSLPASFARRRRLGRWQE (SEQ ID NO 38), MPPKRRLVDDADAMEDQD (SEQ ID NO 39), MEDQDDLYEPPASLPKLP (SEQ ID NO 40) and ELSGEISAIMRMIGVTGLN (SEQ ID NO 41); and b) determining the presence of hybridization product comprising the probe, the presence of the hybridization product indicating the presence of BDV nucleic acid in the sample.

2. The method according to claim 1 wherein the sample is a BDV-infectable cell.

3. The method according to claim 2 wherein the cell is a peripheral blood mononuclear cell.

4. The method according to claim 1 wherein the sample is isolated from a human.

5. The method according to claim 1 wherein detecting the BDV nucleic acid is an indiction of BDV infection.

6. The method according to claim 5 wherein the infection is in a subject having a neuropsychiatric disorder.

7. A kit for detecting the presence of BDV nucleic acid in a sample thereby indicating the presence of BDV nucleic acid in the sample, the kit comprising packaging means being compartmentalized to receive in close confinement therein one or more containers comprising separate containers each containing a polynucleotide sequence encoding a human BDV polypeptide selected from the group of amino acid residue sequences consisting of MATGPSSLVDSLEDEEDP (SEQ ID NO 32),
RIYPQLPSAPTADEWDIIP (SEQ ID NO 33),
MNSKHSYVELKGKVIVPG (SEQ ID NO 34),
RLRNIGVGPLGPDIRSSGP (SEQ ID NO 35),
GLSCNTDSTPGLIDLEIR (SEQ ID NO 36),
RSKLRRRRRDTQQIEYLV (SEQ ID NO 37), LISLCVSLPASFARRRRLGRWQE (SEQ ID NO 38),
MPPKRRLVDDADAMEDQD (SEQ ID NO 39),
MEDQDDLYEPPASLPKLP (SEQ ID NO 40) and
ELSGEISAIMRMIGVTGLN (SEQ ID NO 41).

* * * * *

SEQUENCE LISTING (1) GENERAL INFORMATION:

(iii) NUMBER OF SEQUENCES: 65

(2) INFORMATION FOR SEQ ID NO:1:

(i) SEQUENCE CHARACTERISTICS:
      (A) LENGTH: 8910 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GTTGCGTTAA CAACAAACCA MTCATYATYC TTCTAACAAA ATGAACACAC GCAATGCCAC      60

CCAAGAGACG CCTGGTTGAT GACGCCGATG CCATGGAGGA YCAAGATYTA TATGAACCCC     120

CAGCGAGCCT CCCYAAGCTC CCYGGRAAAT TCCTACAATA CACCGTTGGG GGGTCTGACC     180

CGCATCCGGG TATAGGGCAT GAGAARGAYA TCAGGCAGAA CGCAGTGGCA TTGTTAGACC     240

AGTCACGGCG CGATATGTTT CAYACAGTAA CGCCYAGCCT TGTGTTTCTA TGTTTGCTAA     300

TCCCAGGACT GCACGCTGCG TTTGTTCACG GAGGGGTGCC TCGTGAATCY TACCTGTCGA     360

CGCCTGTYAC GCGTGGRGAA CAGACTGTYG TTAAGACTGC RAAGTTTTAC GGGGAAAAGA     420

CRACRCAGCG TGATCTCACC GAGCTGGAGA TCTCCTCTAT MTTCAGCCAT TGTTGCTCAT     480

TACTAATWGG GGTTGTGATA GGATCGTCRT CTAAGATYAA AGCAGGAGCC GAGCAGATCA     540

AGAAAAGGTT TAAAACTATG ATGGCAGCCT TAAACCGGCC ATCCCATGGT GAGACTGCTA     600

CACTACTYCA GATGTTTAAT CCACATGAGG CTATAGATTG GATTAACGGC CARCCCTGGG     660

TAGGCTCCTT TGTGTTGTCT CTACTAACTA CAGACTTTGA GTCCCCAGGT AAAGAATTYA     720

TGGAYCAGAT TAARCTTGTC GCAAGTTATG CRCAGATGAC TACGTACACT ACTATAAAGG     780

AGTACCTCGC AGAATGYATG GATGCTACCC TTACAATCCC YGTAGTTGCA TATGAGATYC     840

GTGACTTTTT AGAAGTTTCA GCAAAGCTTA ARGAGGAWCA TGCTGACCTG TTYCCGTTYC     900

TGGGGGCYAT TMGRCACCCC GACGCTATCA AGCTKGCGCC ACGRAGCTTT CCCAATCTGG     960

CYTCYGCAGC GTTTTACTGG AGTAAGAAGG ARAAYCCCAC AATGGCRGGC TACCGGGCCT    1020

CCACCATCCA GCCGGGCGCR AGTGTCAAGG ARACCCAGCT TGCCCGGTAT AGGCGCCGCG    1080

AGATATCTCG YGGRGARGAC GGGGCAGAGC TCTCAGGTGA GATCTCTGCC ATAATGARRA    1140

TGATAGGTGT GACTGGTCTA AACTARAAAA CAATGAACAA ACCAATAAAA AACCAAATGC    1200
```

```
GGCAAACCCY CCGCGACCTG YGATGAGYTC CGACCTCCGG CTGACATTGC TTGAAYTAGT   1260

CAGGAGGCTC AATGGCAACG SGACCATCGA GTCTGGTCGA CTCCCTGGAG GACGAAGAAG   1320

ATCCCCAGAC ACTACGACGG GAACGAYCGG GGTCACCAAG ACCACGGAAG RTCCCAAGGA   1380

ATGCATTGAC CCAACCRGTA GACCAGCTCC TGAAGGACCT CAGGAAGAAC CCCTCCATGA   1440

TCTCAGACCC AGACCAGCGA ACCGGAAGGG AGCAGCTRTC GAATGATGAG CTWATCAAGA   1500

AGYTAGTGAC GGAGCTGGCC GAGAATAGCA TGATCGAGGC TGAGGAGGTG CGGGGCACTC   1560

TTGGRGACAT CTCGGCTCGY ATCGAGGCAG GGTTTGAGTC CCTGTCCGCC CTCCAAGTGG   1620

AAACCATCCA GACAGCTCAG CGGTGCGAYC ACTCCGAYAG CATCAGRATC CTYGGCGAGA   1680

ACATCAAGAT ACTRGATCGC TCCATGAAGA CAATGATGGA GACAATGAAG CTCATGATGG   1740

AGAAGGTGGA YCTCCTCTAC GCATCAACCG CCGTTGGGAC CTCTGCACCC ATGTTGCCCT   1800

CCCATCCTGC ACCTCCGCGC ATTTATCCCC AGCTCCCAAG TGCCCCGACA RCGGATGART   1860

GGGACATCAT ACCATAAAAA AATCGAATCA CCATGAATTC AAARCATTCC TATGTGGAGC   1920

TCAAGGRCAA GGTAATCGTC CCTGGATGGC CCACACTGAT GCTTGAGATA GACTTTGTAG   1980

GRGGGACTTC ACGGAACCAG TTCCTTAACA TCCCATTTCT TTCAGTGAAA GAGCCTCTGC   2040

AGCTTCCACG CGAGAAGAAG TTGACCGACT ACTTYACYAT TGACGTAGAR CCAGCAGGTC   2100

ATTCCCTGGT CAAYATATAC TTCCAGATTG ACGACTTCTT GCTCCTAACA CTCAACTCAC   2160

TRTCYGTRTA CAAGGACCCG ATTAGRAAAT ACATGTTCCT ACGCCTCAAC AAGGAMCAGA   2220

GCAAGCACGC AATYAATGCA GCYTTCAATG TCTTYTCTTA TCGGCTTCGG AACATTGGTG   2280

TTGGYCCTCT CGGCCCRGAC ATTCGATCTT CAGGGCCTTA GYTGCAATAC TGACTCCACT   2340

CCTGGAYTRA TYGAYCTGGA GATAAGGCGA CTTTGCCACA CCCCAACGGA AAATGTCATT   2400

TCATGCGAGG TTAGTTATCT YAACCACACG ACTATTAGCC TCCCGGCAGT CCACACRTCA   2460

TGCCTCAAGT ACCACTGCAA AACCTATTGG GGATTCTTTG GTAGCTACAG CGCTGACCGA   2520

ATCATMAATC GGTACACTGG TACTGTTAAG GGTTGTYTAA ACAACTCAGC RCCAGAGGAY   2580

CCCTTCGAGT GCAACTGGTT CTACTGCTGC TCGGCGATTA CAACAGAGAT CTGCCGATGC   2640

TCTATTACAA ATGTCACGGT GGCTGTRCAR ACATTCCCAC CGTTCATGTA CTGCAGTTTY   2700

GCRGACTGYA GTACYGTGAG YCARCAGGAG CTAGAGAGTG GMAAGGCAAT GCTGAGCGAT   2760

GGCAGTACMT TAACTTATAC CCCGTATATC YTACARTCAG AAGTCGTGAA CAAAACCCTY   2820

AATGGGACYA TACTCTGCAA CTCATCCTCY AAGATAGTTT CCTTCGATGA ATTTAGGCGT   2880

TCATACTCCC TARCGAATGG TAGTTACCAG AGCTCATCAA TCAATGTGAC GTGTGYAAAC   2940

TACACGTCGT CCTGCCGGYC CARGTTGARA AGGCGGCGTA GGGAYACYCA RCAGATTGAG   3000

TAYCTAGTTC ACAAGCTTAG GCCYACACTG AAAGATGCRT GGGAGGACTG TGAGATCCTC   3060

CAGTCTCTGC TCCTAGGGRT GTTTGGTACT GGGATYGCAA GTGCTTCKCA ATTYTTGAGG   3120

RGCTGGCTCA ACCACCCTGA YATCATCGGG TATATAGTTA ATGGAGTTGG GGTWGTCTGG   3180

CAATGCCATC GTGTTAATGT CACGTTCATG GCGTGGAATG AGTCCACMTA TTACCCTCCA   3240

GTAGATTACA ATGGRCGGAA GTACTTYCTG AATGATGAGG GRAGGYTACA AACAAACACC   3300

CCCGAGGCAA GGCCAGGGCT TAAGCGGGTC ATGTGGTTCG GCAGGTACTT CCTAGGGACA   3360

GTAGGGTCTG GGGTGAAACC GAGGAGGATT CGGTACAATA AGACCTCACA TGAYTACCAY   3420

CTRGAGGAGT TTGAGGCAAG TCTCAACATG ACCCCYCAGA CCAGTATCGC CTCGGGTCAT   3480

GAGACAGACC CCATAAAATCA TGCCTACGGA ACGCAGGCTG AYCTCCTTCC ATACACCAGG   3540

TCTAGTAATA TAACRTCTAC RGATACAGGC TCAGGCTGGG TGCACATCGG CCTACCCTCA   3600
```

```
TTTGCTTTCC TCAATCCYCT CGGGTGGCTY AGGGACCTAC TTGCRTGGGC RGCCTGGTTG    3660

GGTGGGGTTC TATACTTAAT AAGTCTTTGT GTTTCCTTAC CAGCCTCCTT CGCGAGGAGG    3720

AGACGCCTCG GCCGGTGGCA GGAATAAACC GTACCGACCA RWCTCTTAAA AACCCTCTYC    3780

TCGGRACAGA GGTCTCTTTC TGCCTTAART CGAGYTCACT CCCCCATCAY GTACGAGCAY    3840

TRGGCCAGAT TAAAGCAARG AACCTGGCAT CCTGTGACTA TTACTTGCTA TTCCGCCAAG    3900

TTGTATTGCC CCCTGAAGTA TATCCCATTG GTGTYYTAAT AAGAGCTGCG GAGGCYATAC    3960

TAACAGTTAT AGTATCAGCT TGGAAGCTGG ATCAYATGAC RAAGACCCTA TACTCCTCTG    4020

TGAGATATGC ACTCACCAAT CCCCGGGTCC GRGCCCAACT TGAGCTYCAC ATTGCCTACC    4080

AGCGCATAGT GGGTCAGGTC TCGTAYAGCC GGGARGCAGA YATAGGGCCA AAAAGGCTTG    4140

GGAATATGTC ATTGCAATTC ATCCAATCYC TCGTTATTGC CACCATAGAC ACRACRAGCT    4200

GCCTAATGAC CTACAACCAC TTTCTTGCTG CAGCAGACAC AGCCAAGAGC AGATGCCAYC    4260

TCCTAATCGC CTCAGTGGTC CARGGRGCCC TTTGGGARCA AGGGTCATTT CTTGATCATA    4320

TAATCAACAT GATCGACAYA ATTGACTCAA TCAACCTCCC CCATGATGAT TACTTCACAA    4380

TTATTAAGTC TATCTYTCCC TACTCCCAAG GGCTTGTTAT GGGGAGGCAY AATGTRTCAG    4440

TCTCCTCTGA TTTYGCGTCC GTATTTRCYA TTCCTGAATY ATGCCCRCAA CTAGACAGCT    4500

TACTAAAAAA ACTGCTYCAA CTTGACCCYG TTCTCCTCCT CATGGTCTCT TCGGTGCAGA    4560

AGTCATGGTA CTTCCCTGAG ATCCGAATGG TYGACGGGTC ACGGGAGCAG CTCCACAAGA    4620

TGCGTGTCGA GCTGGARACG CCCCAAGCCC TGCTGTCRTA CGGCCATACC CTCCTGTCAA    4680

TATTTCGRGC AGAGTTTATC AAAGGCTATG TCTCAAAGAA TGCGAAGTGG CCGCCYGTAC    4740

ACCTGCTCCC AGGCTGTGAC AAATCCATAA ARAATGCGAG AGAGCTGGGC CGCTGGAGCC    4800

CGGYRTTTGA CCGACGATGG CAGCTCTTCG MGAAGGTTGT CATTCTAAGA ATTGCTGACC    4860

TAGATATGGA TCCCGACTTC AACGATATTG TTAGCGAYAA GGCGATAATC AGCTCAAGAA    4920

GGGACTGGGT ATTYGAGTAC AATGCAGCRG CCTTTTGGAA GAAATACRGT GARCGGTTGG    4980

AGAGGCCYCC TGCCAGRTCG GGACCRTCAC GRCTTGTGAA TGCTCTRATC GATGGACGCT    5040

TAGAYAATAT CCCAGCCCTG CTAGAGCCAT TTTACAGGGG AGCGGTTGAG TTYGAGGATC    5100

GGYTGACTGT GCTCGTGCCT AAGGAGAARG AGTTRAAGGT AAAGGGAAGG TTCTTCTCGA    5160

AGCAAACATT GGCAATCAGG ATATATCAGG TTGTTGCTGA AGCTGCACTT AAGAAYGAGG    5220

TTATGCCATA CYTAAARACA CAYTCAATGA CCATGAGCTC AACGGCYCTA ACYCAYCTTC    5280

TTAACCGGCT ATCACATACT ATCACTAAGG GTGACTCCTT TGTTATTAAC YTWGAYTATA    5340

GYTCCTGGTG CAACGGTTTC CGACCAGAAC TRCARGCCCC AMTCTGTCGT CAGTTGGATC    5400

AGATGTTCAA TTGCGGGTAC TTCTTCAGGA CTGGGTGCAC ACTGCCATGC TTTACCACGT    5460

TTATTATTCA RGACAGRTTC AACCCGCCCT ATTCCYTCMG TGGTGAGCCC GTTGAAGACG    5520

GWGTYACATG CGCGGTTGGG ACTAARACAA TGGGRGAGGG YATGAGGCAG AAACTATGGA    5580

CAATYCTTAC GAGCTGCTGG GAGATAATTG CTCTTCGGGA AATTAACGTG ACGTTTAAYA    5640

TACTAGGCCA RGGTGATAAT CAGACAATCA TYRTACATAA ATCTGCAAGC CAAAATAAYC    5700

AGCTATTAGC GGAGCGAGCA YTRGGRGCYY TGTACAAGCA TGCTAGATTA GCTGGCCATA    5760

ACCTYAAGGT AGARGAATGY TGGGTGTCAG ATTGTCTGTA TGAGTATGGA AAGAAGCTYT    5820

TCTTCCGTGG TGTACCTGTC CCRGGCTGTT TGAAGCAGCT CTCRCGGGTG ACGGAYTCYA    5880

CTGGRGAGYT ATTCCCAAAC CTATACTCAA AGTTAGCCTG CTTAACATCA TCRTGYTTAA    5940
```

-continued

```
GCGCAGCGAT GGCAGACACA TCYCCATGGG TGGCACTCGC GACAGGTGTC TGTCTGTATC    6000

TTATCGAGTT RTATGTTGAG CTGCCTCCRG CAATCATGCA GGAYGAGTCG CTRTTRACGA    6060

CCCTCTGYCT CGTAGGYCCA TCCATTGGTG GGCTTCCRAC YCCTGCAACC CTRCCCAGTG    6120

TCTTTTTCAG AGGAATGTCC GACCCAYTGC CCTTTCAGCT AGCACTCTTG CAGACCCTCA    6180

TTAARACGAC AGGGGTGACY TGTAGCTTGG TGAATCGTGT GGTYAAGTTA CGGATAGCAC    6240

CCTATCCAGA CTGGCTCTCY CTAGTGACTG ACCCGACYTC ACTCAACATT GCYCARGTGT    6300

ACCGGCCAGA ACGTCARATC AGGAGGTGGA TTGAGGARGC RATAGCRACA AGCTCACACT    6360

CGTCACGCAT AGCAACTTTY TTCCAGCAGS CCCTCACGGA GATGGCYCAG YTGCTTGCGA    6420

GGGACCYTYC AACAATGATG CCTCTTCGRC CCCGGGATAT GTCGGCCTTA TTCGCATTAT    6480

CAAATGTCGC ATAYGGTYTA AGCATTATAG ATCTATTTCA AAARTCCTCT ACCGTTGTYT    6540

CTGCAAGTCA AGCTGTCCAT ATCGARGATG TTGCCCTAGA GAGTGTAAGG TATAAGGAAT    6600

CTATCATYCA GGGTCTGTTA GACACYACTG AGGGGTAYAA CATGCAACCT TATTTGGAAG    6660

GTTGCACTTA CCTTGCAGCC AARCAGYTAC GKAGGTTGAC RTGGGGTCGA GACCTAGTTG    6720

GAGTYACAAT GCCGTTTGTT GCCGAGCAAT TCCATCCYCA YAGTTCTGTS GGTGCAAARG    6780

CRGAACTCTA CCTCGAYGCT ATYATATACT GCCCACARGA GACRTTGCGG TCACACCATC    6840

TGACTACCAG GGGGACCAG CCGCTTTACC TYGGATCYAA TACGGCTGTC AMGGTYCAGC    6900

GAGGTGAGAT CACRGGCCTA ACAAAGTCAA GGGCTGCAAA TCTAGTCARG GACACTCTCG    6960

TTCTCCAYCA GTGGTAYAAR GTCCGTAARG TTACCGATCC ACACTTGAAC ACYCTCATGG    7020

CRCGCTTCTT RCTTGAGAAG GGRTACACAT CTGACGCTCG RCCTAGCATY CAGGGTGGGA    7080

CCCTCACRCA TCGTCTCCCA TCCCGYGGAG ACTCACGSCA RGGGCTYACT GGGTATGTRA    7140

ATATACTMAG YACGTGGCTY CGRTTCTCAA GTGATTATCT TCACTCTTTC TCGAAATCAT    7200

CAGAYGACTA YACAATCCAC TTYCAGCATG TATTCACATA CGGTTGCCTC TATGCTGATT    7260

CGGTGATTAG ATCGGGCGGT GTTATTTCCA CTCCTTACCT TTTGAGTGCA AGTTGTAAAA    7320

CATGCTTTGA GAAGATAGAC TCAGAGGAGK TCGTCCTGGC ATGYGAACCY CAATAYAGGG    7380

GTGCTGAGTG GCTGATATCA AAGCCAGTYA CTGTCCCTGA GCAGATAAYT GAYGCTGAAG    7440

TCGAGTTTGA CCCCTGTGTG AGTGCGRGTT ATTGTCTCGG GATTCTCATT GGCAAGTCAT    7500

TCTTRGTTGA CATAAGGGCA AGTGGGCATG ATATYATGGA GCAGCGGACA TGGGCTAACY    7560

TGGAGAGGTT TTCTGTRTCG GACATGCAGA AACTTCCRTG GAGTATTGTA ATTCGGTCTC    7620

TCTGGAGATT CCTTATTGGC GCACGRCTCC TYCAGTTTGA GAAGGCTGGC CTYATTAGRA    7680

TGCTGTATGC TGCRACAGGT CCAACCYYTA GCTTCCTAAT GAAAGTYTTT CAAGACTCAG    7740

CCCTMCTYAT GGACTGCGCA CCYCTYGATC GGCTGTMCCC TAGGATCAAC TTTCATAGTC    7800

GGGGAGACCT CGTYGCYAAG CTYGTTTTAT TRCCCTTCAT CAACCCGGGT ATAGTGGAGA    7860

TTGAAGTGTC TRGAATTAAT AGCAAGTAYC ATGCAGTATC GGAGGCYAAT ATGGATCTGT    7920

ACATCGCTGC TGCMAARTCT GTGGGCGTRA AGCCACACA GTTTGTTGAG GAAACAAACG    7980

ACTTTACGGC CCGCGGCCAC CACCATGGTT GTTATTCCCT TCTTGGTCT AAGTCACGCA    8040

ATCAATCACA GGTCCTAAAG ATGGTAGTRC GGAAGCTGAA GCTMTGTGTC CTGTATATAT    8100

ACCCCACAGT CGATCCCGCC GTTGCTCTCG ACCTGTGCCA YCTRCCAGCA YTAACTATAA    8160

TCCTAGTGCT CGGCGGTGAC CCAGCGTACT AYGAGCGATT ACTTGAGATG GACCTRTGCG    8220

GGGCTGTGTC AAGTCGMGTY GATATCCCCC ATTCYCTRGC TGSCAGAACG CACAGGGGGT    8280

TCRCARTRGG CCCAGACGCT GGTCCAGGTG TRATTAGACT YGACARGTTA GAGTCRGTTT    8340
```

```
GTTAYGCYCA CCCCTGTTTR GAGGARCTAG AGTTTAATGC RTAYCTAGAC TCTGAGTTRG      8400

TTGAYATTAG TGATATGTGC TGCCTCCCCY TAGCGACACC CTGTAAGGCC CTWTTCAGGC      8460

CARTRTATCG GAGCTTACAG TCGTTCAGGT TAGCCTTAAT GGACAACTAT AGTTTTGTMA      8520

TGGACCTCAT TAYGATCCGR GGRSTGGACA TYAGGCCTCA CCTTGAGGAR TTTGAYGARC      8580

TGCTTGTGGT RGGRCAGCAY ATCCTCGGYC AGCCCGTCCT AGTRGAGGTT GTTTACTACG      8640

TTGGAGTTGT TRGGAAGCGY CCTGTGTTAG CGAGGCATCC STGGTCAGCA GATCTTAAGC      8700

GAATYACTGT RGGGGGGCGR GCKCCCTGCC CYTCTGCTGC YRGAYTGCGT GATGAGGATT      8760

GTCRGGGGTC TCTGYTGGTT GGGCTTCCYG CTGGRTTGAC GCAGTTRTTG RTRRTTGATT      8820

RAGRTYRAGC CAYCTACTRC CCTATTCTTA AAAAACCATA YGTCAGTGGT GCAGTGCTTG      8880

GGYTTGGTTG TTGCTTTGTT GTAGCGCKTT                                       8910

(2) INFORMATION FOR SEQ ID NO:2:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

ATGGCAACGC GACCATCGAG TCTGGTCGAC TCCCTGGAGG ACGAAGAAGA TCCCCAGACA        60

CTACGACGGG AACGACCGGG GTCACCAAGA CCACGGAAGG TCCCAAGGAA TGCATTGACC       120

CAACCAGTAG ACCAGCTCCT GAAGGACCTC AGGAAGAACC CCTCCATGAT CTCAGACCCA       180

GACCAGCGAA CCGGAAGGGA GCAGCTGTCG AATGATGAGC TAATCAAGAA GTTAGTGACG       240

GAGCTGGCCG AGAATAGCAT GATCGAGGCT GAGGAGGTGG GGGCACTCT TGGAGACATC        300

TCGGCTCGTA TCGAGGCAGG GTTTGAGTCC CTGTCCGCCC TCCAAGTGGA AACCATCCAG       360

ACAGCTCAGC GGTGCGATCA CTCCGACAGC ATCAGGATCC TCGGCGAGAA CATCAAGATA       420

CTAGATCGCT CCATGAAGAC AATGATGGAG ACAATGAAGC TCATGATGGA GAAGGTGGAT       480

CTCCTCTACG CATCAACCGC CGTTGGGACC TCTGCACCCA TGTTGCCCTC CCATCCTGCA       540

CCTCCGCGCA TTTATCCCCA GCTCCCAAGT GCCCCGACAA CGGATGAATG GGACATCATA       600

CCA                                                                     603

(2) INFORMATION FOR SEQ ID NO:3:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

ATGGCAACGG AACCATCGAG TCTGGTCGAC TCCCTGGAGG ACGAAGAAGA TCCCCAGACA        60
```

```
CTACGACGGG AACGATCGGG GTCACCAAGA CCACGGAAGG TCCCAAGGAA TGCATTGACC      120

CAACCAGTAG ACCAGCTCCT GAAGGACCTC AGGAAGAACC CCTCCATGAT CTCAGACCCA      180

GACCAGCGAA CCGGAAGGGA GCAGCTGTCG AATGATGAGC TAATCAAGAA GTTAGTGACG      240

GAGCTGGCCG AGAATAGCAT GATCGAGGCT GAGGAGGTGC GGGGCACTCT TGGAGACATC      300

TCGGCTCGTA TCGAGGCAGG GTTTGAGTCC CTGTCCGCCC TCCAAGTGGA AACCATCCAG      360

ACAGCTCAGC GGTGCGATTA CTCCGACAGC ATCAGGATCC TCGGCGAGAA CATCAAGATA      420

CTAGATCGCT CCATGAAGAC AATGATGGAG ACAATGAAGC TCATGATGGA GAAGGTGGAT      480

CTCCTCTACG CATCAACCGC CGTTGGGACC TCTGCACCCA TGTTGCCCTC CCATCCTGCA      540

CCTCCGCGCA TTTATCCCCA GCTCCCAAGT GCCCCGACAA CGGATGAGTG GACATCATA      600

CCA                                                                    603

(2) INFORMATION FOR SEQ ID NO:4:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

ATGGCAACGG GACCATCGAG TCTGGTCGAC TCCCTGGAGG ACGAAGAAGA TCCCCAGACA       60

CTACGACGGG AACGATCGGG GTCACCAAGA CCACGGAAGG TCCCAAGGAA TGCATTGACC      120

CAACCAGTAG ACCAGCTCCT GAAGGACCTC AGGAAGAACC CCTCCATGAT CTCAGACCCA      180

GACCAGCGAA CCGGAAGGGA GCAGCTGTCG AATGATGAGC TAATCAAGAA GTTAGTGACG      240

GAGCTGGCCG AGAATAGCAT GATCGAGGCT GAGGAGGTGC GGGGCACTCT TGGAGACATC      300

TCGGCTCGTA TCGAGGCAGG GTTTGAGTCC CTGTCCGCCC TCCAAGTGGA AACCATCCAG      360

ACAGCTCAGC GGTGCGATCA CTCCGACAGC ATCAGGATCC TCGGCGAGAA CATCAAGATA      420

CTAGATCGCT CCATGAAGAC AATGATGGAG ACAATGAAGC TCATGATGGA GAAGGTGGAT      480

CTCCTCTACG CATCAACCGC CGTTGGGACC TCTGCACCCA TGTTGCCCTC CCATCCTGCA      540

CCTCCGCGCA TTTATCCCCA GCTCCCAAGT GCCCCGACAA CGGATGAGTG GACATCATA      600

CCA                                                                    603

(2) INFORMATION FOR SEQ ID NO:5:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

ATGGCAACGG AACCATCGAG TCTGGTCGAC TCCCTGGAGG ACGAAGAAGA TCCCCAGACA       60

CTACGACGGG AACGATCGGG GTCACCAAGA CCACGGAAGG TCCCAAGGAA TGCATTGACC      120
```

```
CAACCAGTAG ACCAGCTCCT GAAGGACCTC AGGAAGAACC CCTCCATGAT CTCAGACCCA      180

GACCAGCGAA CCGGAAGGGA GCAGCTGTCG AATGATGAGC TAATCAAGAA GTTAGTGACG      240

GAGCTGGCCG AGAATAGCAT GATCGAGGCT GAGGAGGTGC GGGGCACTCT TGGAGACATC      300

TCGGCTCGTA TCGAGGCAGG GTTTGAGTCC CTGTCCGCCC TCCAAGTGGA AACCATCCAG      360

ACAGCTCAGC GGTGCGACCA CTCCGACAGC ATCAGGATCC TCGGCGAGAA CATCAAGATA      420

CTAGATCGCT CCATGAAGAC AATGATGGAG ACAATGAAGC TCATGATGGA GAAGGTGGAT      480

CTCCTCTACG CATCAACCGC CGTTGGGACC TCTGCACCCA TGTTGCCCTC CCATCCTGCA      540

CCTCCGCGCA TTTATCCCCA GCTCCCAAGT GCCCCGACAA CGGATGAGTG GACATCATA       600

CCA                                                                   603
```

(2) INFORMATION FOR SEQ ID NO:6:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

```
ATGAATTCAA AACATTCCTA TGTGGAGCTC AAGGACAAGG TAATCGTCCC TGGATGGCCC       60

ACACTGATGC TTGAGATAGA CTTTGTAGGG GGGACTTCAC GGAACCAGTT CCTTAACATC      120

CCATTTCTTT CAGTGAAAGA GCCTCTGCAG CTTCCACGCG AGAAGAAGTT GACCGACTAC      180

TTTACTATTG ACGTAGAACC AGCAGGTCAT TCCCTGGTCA ATATATACTT CCAGATTGAC      240

GACTTCTTGC TCCTAACACT CAACTCACTA TCTGTGTACA AGGACCCGAT TAGAAAATAC      300

ATGTTCCTAC GCCTCAACAA GGACCAGAGC AAGCACGCAA TCAATGCAGC CTTCAATGTC      360

TTTTCTTATC GGCTTCGGAA CATTGGTGTT GGTCCTCTCG GCCCGGACAT TCGATCTTCA      420

GGGCCT                                                                426
```

(2) INFORMATION FOR SEQ ID NO:7:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

```
ATGAATTCAA AGCATTCCTA TGTGGAGCTC AAGGACAAGG TAATCGTCCC TGGATGGCCC       60

ACACTGATGC TTGAGATAGA CTTTGTAGGG GGGACTTCAC GGAACCAGTT CCTTAACATC      120

CCATTTCTTT CAGTGAAAGA GCCTCTGCAG CTTCCACGCG AGAAGAAGTT GACCGACTAC      180

TTTACTATTG ACGTAGAACC AGCAGGTCAT TCCCTGGTCA ATATATACTT TCAGATTGAC      240

GACTTCTTGC TCCTAACACT CAACTCACTA TCTGTGTACA AGGACCCGAT TAGAAAATAC      300
```

```
ATGTTCCTAC GCCTCAACAA GGACCAGAGC AAGCACGCAA TCAATGCAGC CTTCAATGTC    360

TTTTCTTATC GGCTTCGGAA CATTGGTGTT GGTCCTCTCG GCCCGGACAT TCGATCTTCA    420

GGGCCT                                                                426

(2) INFORMATION FOR SEQ ID NO:8:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

ATGAATTCAA AGCATTCCTA TGTGGAGCTC AAGGACAAGG TAATCGTCCC TGGATGGCCC     60

ACACTGATGC TTGAGATAGA CTTTGTAGGG GGGACTTCAC GGAACCAGTT CCTTAACATC    120

CCATTTCTTT CAGTGAAAGA GCCTCTGCAG CTTCCACGCG AGAAGAAGTT GACCGACTAC    180

TTTACTATTG ACGTAGAACC AGCAGGTCAT TCCCTGGTCA ATATATACTT CCAGATTGAC    240

GACTTCTTGC TCCTAACACT CAACTCACTA TCTGTGTACA AGGACCCGAT TAGAAAATAC    300

ATGTTCCTAC GCCTCAACAA GGACCAGAGC AAGCACGCAA TCAATGCAGC CTTCAATGTC    360

TTTTCTTATC GGCTTCGGAA CATTGGTGTT GGTCCTCTCG GCCCGGACAT TCGATCTTCA    420

GGGCCT                                                                426

(2) INFORMATION FOR SEQ ID NO:9:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

ATGAATTCAA AGCATTCCTA TGTGGAGCTC AAGGACAAGG TAATCGTCCC TGGATGGCCC     60

ACACTGATGC TTGAGATAGG CTTTGTAGGG GGGACTTCAC GGAACCAGTT CCTTAACATC    120

CCATTTCTTT CAGTGAAAGA GCCTCTGCAG CTTCCACGCG AGAAGAAGTT GACCGACTAC    180

TTTACTATTG ACGTAGAACC AGCAGGTCAT TCCCTGGTCA ATATATACTT CCAGATTGAC    240

GACTTCTTGC TCCTAACACT CAACTCACTA TCTGTGTACA AGGACCCGAT TAGAAAATAC    300

ATGTTCCTAC GCCTCAACAA GGACCAGAGC AAGCACGCAA TCAATGCAGC CTTCAATGTC    360

TTTTCTTATC GGCTTCGGAA CATTGGTGTT GGTCCTCTCG GCCCGGACAT TCGATCTTCA    420

GGGCCT                                                                426

(2) INFORMATION FOR SEQ ID NO:10:

(i) SEQUENCE CHARACTERISTICS:
        (A) LENGTH: 1521 base pairs
        (B) TYPE: nucleic acid
        (C) STRANDEDNESS: single
```

(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

```
ATGCAGCCTT CAATGTCTTT TCTTATCGGC TTCGGAACAT TGGTGTTGGT CCTCTCGGCC      60

CGGACATTCG ATCTTCAGGG CCTTAGCTGC AATACTGACT CCACTCCTGG ACTGATTGAC     120

CTGGAGATAA GGCGACTTTG CCACACCCCA ACGGAAAATG TCATTTCATG CGAGGTTAGT     180

TATCTCAACC ACACGACTAT TAGCCTCCCG GCAGTCCACA CATCATGCCT CAAGTACCAC     240

TGCAAAACCT ATTGGGGATT CTTTGGTAGC TACAGCGCTG ACCGAATCAT AAATCGGTAC     300

ACTGGTACTG TTAAGGGTTG TCTAAACAAC TCAGCACCAG AGGACCCCTT CGAGTGCAAC     360

TGGTTCTACT GCTGCTCGGC GATTACAACA GAGATCTGCC GATGCTCTAT TACAAATGTC     420

ACGGTGGCTG TGCAAACATT CCCACCGTTC ATGTACTGCA GTTTTGCAGA CTGCAGTACC     480

GTGAGCCAAC AGGAGCTAGA GAGTGGAAAG GCAATGCTGA GCGATGGCAG TACATTAACT     540

TATACCCCGT ATATCCTACA GTCAGAAGTC GTGAACAAAA CCCTCAATGG GACCATACTC     600

TGCAACTCAT CCTCTAAGAT AGTTTCCTTC GATGAATTTA GGCGTTCATA CTCCCTAACG     660

AATGGTAGTT ACCAGAGCTC ATCAATCAAT GTGACGTGTG CAAACTACAC GTCGTCCTGC     720

CGGCCCAGGT TGAAAAGGCG GCGTAGGGAC ACCCAGCAGA TTGAGTATCT AGTTCACAAG     780

CTTAGGCCCA CACTGAAAGA TGCATGGGAG GACTGTGAGA TCCTCCAGTC TCTGCTCCTA     840

GGGGTGTTTG GTACTGGGAT CGCAAGTGCT TCTCAATTTT TGAGGAGCTG GCTCAACCAC     900

CCTGACATCA TCGGGTATAT AGTTAATGGA GTTGGGGTTG TCTGGCAATG CCATCGTGTT     960

AATGTCACGT TCATGGCGTG GAATGAGTCC ACCTATTACC CTCCAGTAGA TTACAATGGG    1020

CGGAAGTACT TCCTGAATGA TGAGGGAAGG TTACAAACAA ACACCCCCGA GGCAAGGCCA    1080

GGGCTTAAGC GGGTCATGTG GTTCGGCAGG TACTTCCTAG GACAGTAGG GTCTGGGGTG    1140

AAACCGAGGA GGATTCGGTA CAATAAGACC TCACATGACT ACCACCTGGA GGAGTTTGAG    1200

GCAAGTCTCA ACATGACCCC TCAGACCAGT ATCGCCTCGG GTCATGAGAC AGACCCCATA    1260

AATCATGCCT ACGGAACGCA GGCTGATCTC CTTCCATACA CCAGGTCTAG TAATATAACA    1320

TCTACGGATA CAGGCTCAGG CTGGGTGCAC ATCGGCTAC CCTCATTTGC TTTCCTCAAT     1380

CCCCTCGGGT GGCTCAGGGA CCTACTTGCA TGGGCAGCCT GGTTGGGTGG GGTTCTATAC    1440

TTAATAAGTC TTTGTGTTTC CTTACCAGCC TCCTTCGCGA GGAGGAGACG CCTCGGCCGG    1500

TGGCAGGAAT AAACCGTACC G                                              1521
```

(2) INFORMATION FOR SEQ ID NO:11:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

```
ATGCAGCCTT CAATGTCTTT TCTTATCGGC TTCGGAACAT TGGTGTTGGT CCTCTCGGCC      60

CGGACATTCG ATCTTCAGGG CCTTAGCTGC AATACTGACT CCACTCCTGG ACTGATTGAC     120

CTGGAGATAA GGCGACTTTG CCACACCCCA ACGGAAAATG TCATTTCATG CGAGGTTAGT     180

TATCTCAACC ACACGACTAT TAGCCTCCCG GCAGTCCACA CATCATGCCT CAAGTACCAC     240

TGCAAAACCT ATTGGGGATT CTTTGGTAGC TACAGCGCTG ACCGAATCAT AAATCGGTAC     300

ACTGGTACTG TTAAGGGTTG TCTAAACAAC TCAGCACCAG AGGACCCCTT CGAGTGCAAC     360

TGGTTCTACT GCTGCTCGGC GATTACAACA GAGATCTGCC GATGCTCTAT TACAAATGTC     420

ACGGTGGCTG TGCAAACATT CCCACCGTTC ATGTACTGCA GTTTTGCAGA CTGCAGTACC     480

GTGAGCCAAC AGGAGCTAGA GAGTGGAAAG GCAATGCTGA GCGATGGCAG TACATTAACT     540

TATACCCCGT ATATCCTACA GTCAGAAGTC GTGAACAAAA CCCTCAATGG GACCATACTC     600

TGCAACTCAT CCTCTAAGAT AGTTTCCTTC GATGAATTTA GGCGTTCATA CTCCCTAACG     660

AATGGTAGTT ACCAGAGCTC ATCAATCAAT GTGACGTGTG CAAACTACAC GTCGTCCTGC     720

CGGCCCAGGT TGAAAAGGCG GCGTAGGGAC ACCCAGCAGA TTGAGTATCT AGTTCACAAG     780

CTTAGGCCCA CACTGAAAGA TGCATGGGAG GACTGTGAGA TCCTCCAGTC TCTGCTCCTA     840

GGGGTGTTTG GTACTGGGAT CGCAAGTGCT TCTCAATTTT TGAGGAGCTG GCTCAACCAC     900

CCTGACATCA TCGGGTATAT AGTTAATGGA GTTGGGGTTG TCTGGCAATG CCATCGTGTT     960

AATGTCACGT TCATGACGTG GAATGAGTCC ACCTATTACC CTCCAGTAGA TTACAATGGG    1020

CGGAAGTACT TCCTGAATGA TGAGGGAAGG TTACAAACAA ACACCCCCGA GGCAAGGCCA    1080

GGGCTTAAGC GGGTCATGTG GTTCGGCAGG TACTTCCTAG GACAGTAGG GTCTGGGGTG     1140

AAACCGAGGA GGATTCGGTA CAATAAGACC TCACATGACT ACCACCTGGA GGAGTTTGAG    1200

GCAAGTCTCA ACATGACCCC TCAGACCAGT ATCACCTCGG GTCATGAGAC AGACCCCATA    1260

AATCATGCCT ACGAACGCA GGCTGATCTC CTTCCATACA CCAGGTCTAG TAATATAACA    1320

TCTACGGATA CAGGCTCAGG CTGGGTGCAC ATCGGCCTAC CCTCATTTGC TTTCCTCAAT    1380

CCCCTCGGGT GGCTCAGGGA CCTACTTGCA TGGGCAGCCT GGTTGGGTGG GGTTCTATAC    1440

TTAATAAGTC TTTGTGTTTC CTTACCAGCC TCCTTCGCGA GGAGGAGACG CCTCGGCCGG    1500

TTGCAGGAAT AAACCGTACC G                                            1521
```

(2) INFORMATION FOR SEQ ID NO:12:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

```
ATGCAGCCTT CAATGTCTTT TCTTATCGGC TTCGGAACAT TGGTGTTGGT CCTCTCGGCC      60

CGGACATTCG ATCTTCAGGG CCTTAGCTGC AATACTGACT CCACTCCTGG ACTGATTGAC     120

CTGGAGATAA GGCGACTTTG CCACACCCCA ACGGAAAATG TCATTTCATG CGAGGTTAGT     180

TATCTCAACC ACACGACTAT TAGCCTCCCG GCAGTCCACA CATCATGCCT CAAGTACCAC     240

TGCAAAACCT ATTGGGGATT CTTTGGTAGC TACAGCGCTG ACCGAATCAT AAATCGGTAC     300
```

```
ACTGGTACTG TTAAGGGTTG TCTAAACAAC TCAGCACCAG AGGACCCCTT CGAGTGCAAC      360

TGGTTCTACT GCTGCTCGGC GATTACAACA GAGATCTGCC GATGCTCTAT TACAAATGTC      420

ACGGTGGCTG TGCAAACATT CCCACCGTTC ATGTACTGCA GTTTTGCAGA CTGCAGTACC      480

GTGAGCCAAC AGGAGCTAGA GAGTGGAAAG GCAATGCTGA GCGATGGCAG TACATTAACT      540

TATACCCCGT ATATCCTACA GTCAGAAGTC GTGAACAAAA CCCTCAATGG GACCATACTC      600

TGCAACTCAT CCTCTAAGAT AGTTTCCTTC GATGAATTTA GGCGTTCATA CTCCCTAACG      660

AATGGTAGTT ACCAGAGCTC ATCAATCAAT GTGACGTGTG CAAACTACAC GTCGTCCTGC      720

CGGCCCAGGT TGAAAAGGCG GCGTAGGGAC ACCCAGCAGA TTGAGTATCT AGTTCACAAG      780

CTTAGGCCCA CACTGAAAGA TGCATGGGAG GACTGTGAGA TCCTCCAGTC TCTGCTCCTA      840

GGGGTGTTTG GTACTGGGAT CGCAAGTGCT TCTCAATTTT TGAGGAGCTG GCTCAACCAC      900

CCTGACATCA TCGGGTATAT AGTTAATGGA GTTGGGGTTG TCTGGCAATG CCATCGTGTT      960

AATGTCACGT TCATGACGTG GAATGAGTCC ACCTATTACC CTCCAGTAGA TTACAATGGG     1020

CGGAAGTACT TCCTGAATGA TGAGGGAAGG TTACAAACAA ACACCCCCGA GGCAAGGCCA     1080

GGGCTTAAGC GGGTCATGTG GTTCGGCAGG TACTTCCTAG GGACAGTAGG GTCTGGGGTG     1140

AAACCGAGGA GGATTCGGTA CAATAAGACC TCACATGACT ACCACCTGGA GGAGTTTGAG     1200

GCAAGTCTCA ACATGACCCC TCAGACCAGT ATCGCCTCGG GTCATGAGAC AGACCCCATA     1260

AATCATGCCT ACGGAACGCA GGCTGATCTC CTTCCATACA CCAGGTCTAG TAATATAACA     1320

TCTACGGATA CAGGCTCAGG CTGGGTGCAC ATCGGCCTAC CCTCATTTGC TTTCCTCAAT     1380

CCCCTCGGGT GGCTCAGGGA CCTACTTGCA TGGGCAGCCT GGTTGGGTGG GGTTCTATAC     1440

TTAATAAGTC TTTGTGTTTC CTTACCAGCC TCCTTCGCGA GGAGGAGACG CCTCGGCCGG     1500

TGGCAGGAAT AAACCGTACC G                                               1521
```

(2) INFORMATION FOR SEQ ID NO:13:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

```
TTCAYACAGT AACGCCYAGC CTTGTGTTTC TATGTTTGCT AATCCCAGGA CTGCACGCTG       60

CGTTTGTTCA CGGAGGGGTG CCTCGTGAAT CYTACCTGTC GACGCCTRTY ACGCGTGGRG      120

AACAGACTGT YGTTAAGACT GCRRAGTTTT ACGGGGAAAA GACRACRCAG CGTGATCTCA      180

CCGAGCTGGA GATCTCCTCT ATMTTCAGCC ATTGTTGCTC ATTACTAATW GGGGTTGTGA      240

TAGGATCGTC RTCTAAGATY AAAGCAGRAG CCGAGCAGAT CAAGAAAAGG TTTAAAACTA      300

TGATGGCAGC CKTAAACCGG CCATCCCATG GTGAGACTGC TACACTACTY CAGATGTTTA      360

ATCCACATGA GGCTATAGAT TGGATTAACG GCCARCCCTG GGTAGGCTCC TTTGTGTTGY      420

CTCTACTAAC TACAGACTTT GAGTCCCCAG GTAAAGAATT YATGGAYCAG ATTAARCTTG      480

TCGCAAGTTA TGCRCAGATG ACTACGTACA CTACTATAAA GGAGTACCTC GCAGAATGYA      540

TGGATGCTAC CCTTACAATC CCYGTAGTTG C                                     571
```

(2) INFORMATION FOR SEQ ID NO:14:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

```
TTCATACAGT AACGCCCAGC CTTGTGTTTC TATGTTTGCT AATCCCAGGA CTGCACGCTG    60

CGTTTGTTCA CGGAGGGGTG CCTCGTGAAT CCTACCTGTC GACGCCTGTC ACGCGTGGAG   120

AACAGACTGT TGTTAAGACT GCGAAGTTTT ACGGGGAAAA GACGACGCAG CGTGATCTCA   180

CCGAGCTGGA GATCTCCTCT ATCTTCAGCC ATTGTTGCTC ATTACTAATA GGGGTTGTGA   240

TAGGATCGTC GTCTAAGATC AAAGCAGGAG CCGAGCAGAT CAAGAAAAGG TTTAAAACTA   300

TGATGGCAGC CTTAAACCGG CCATCCCATG GTGAGACTGC TACACTACTC CAGATGTTTA   360

ATCCACATGA GGCTATAGAT TGGATTAACG GCCAACCCTG GGTAGGCTCC TTTGTGTTGC   420

CTCTACTAAC TACAGACTTT GAGTCCCCAG GTAAAGAATT TATGGACCAG ATTAAGCTTG   480

TCGCAAGTTA TGCACAGATG ACTACGTACA CTACTATAAA GGAGTACCTC GCAGAATGCA   540

TGGATGCTAC CCTTACAATC CCTGTAGTTG C                                  571
```

(2) INFORMATION FOR SEQ ID NO:15:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

```
TTCATACAGT AACGCCCAGC CTTGTGTTTC TATGTTTGCT AATCCCAGGA CTGCACGCTG    60

CGTTTGTTCA CGGAGGGGTG CCTCGTGAAT CCTACCTGTC GACGCCTATC ACGCGTGGAG   120

AACAGACTGT TGTTAAGACT GCGGAGTTTT ACGGGGAAAA GACGACGCAG CGTGATCTCA   180

CCGAGCTGGA GATCTCCTCT ATCTTCAGCC ATTGTTGCTC ATTACTAATA GGGGTTGTGA   240

TAGGATCGTC GTCTAAGATC AAAGCAGAAG CCGAGCAGAT CAAGAAAAGG TTTAAAACTA   300

TGATGGCAGC CGTAAACCGG CCATCCCATG GTGAGACTGC TACACTACTC CAGATGTTTA   360

ATCCACATGA GGCTATAGAT TGGATTAACG GCCAACCCTG GGTAGGCTCC TTTGTGTTGT   420

CTCTACTAAC TACAGACTTT GAGTCCCCAG GTAAAGAATT TATGGACCAG ATTAAGCTTG   480

TCGCAAGTTA TGCACAGATG ACTACGTACA CTACTATAAA GGAGTACCTC GCAGAATGCA   540

TGGATGCTAC CCTTACAATC CCTGTAGTTG C                                  571
```

(2) INFORMATION FOR SEQ ID NO:16:

(i) SEQUENCE CHARACTERISTICS:
        (A) LENGTH: 571 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

| | | | | | |
|---|---|---|---|---|---|
| TTCATACAGT | AACGCCCAGC | CTTGTGTTTC | TATGTTTGCT | AATCCCAGGA | CTGCACGCTG | 60 |
| CGTTTGTTCA | CGGAGGGGTG | CCTCGTGAAT | CCTACCTGTC | GACGCCTATC | ACGCGTGGAG | 120 |
| AACAGACTGT | TGTTAAGACT | GCGAAGTTTT | ACGGGGAAAA | GACGACGCAG | CGTGATCTCA | 180 |
| CCGAGCTGGA | GATCTCCTCT | ATCTTCAGCC | ATTGTTGCTC | ATTACTAATA | GGGGTTGTGA | 240 |
| TAGGATCGTC | GTCTAAGATC | AAAGCAGGAG | CCGAGCAGAT | CAAGAAAAGG | TTTAAAACTA | 300 |
| TGATGGCAGC | CTTAAACCGG | CCATCCCATG | GTGAGACTGC | TACACTACTC | CAGATGTTTA | 360 |
| ATCCACATGA | GGCTATAGAT | TGGATTAACG | GCCAACCCTG | GGTAGGCTCC | TTTGTGTTGT | 420 |
| CTCTACTAAC | TACAGACTTT | GAGTCCCCAG | GTAAAGAATT | TATGGACCAG | ATTAAGCTTG | 480 |
| TCGCAAGTTA | TGCACAGATG | ACTACGTACA | CTACTATAAA | GGAGTACCTC | GCAGAATGCA | 540 |
| TGGATGCTAC | CCTTACAATC | CCTGTAGTTG | C | | | 571 |

(2) INFORMATION FOR SEQ ID NO:17:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

| | | | | | |
|---|---|---|---|---|---|
| TGACCATGAG | CTCAACGGCY | CTAACYCAYC | TTCTTAACCG | GCTATCACAT | ACTATCACTA | 60 |
| AGGGTGACTC | CTTTGTTATT | AACYTWGAYT | ATAGYTCCTG | GTGCAACGGT | TTCCGACCAG | 120 |
| AACTRCARGC | CCCAMTCTGT | CGTCAGTTGG | ATCAGATGTT | CAATTGCGGG | TACTTCTTCA | 180 |
| GGACTGGGTG | CACACTGCCA | TGCTTTACCA | CGTTTATTAT | TCARGACAGR | TTCAACCCGC | 240 |
| CCTATTCCYT | CMGTGGTGAG | CCCGTTGAAG | ACGGWGTYAC | ATGCGCGGTT | GGGACTAARA | 300 |
| CAATGGGRGA | GGGYATGAGG | CAGAAACTAT | GGACAATYCT | TACGAGCTGC | TGGGAGATAA | 360 |
| TTGCTCTTCG | GGAAATTAAC | GTGACGTTTA | AYATACTAGG | CCARGGTGAT | AATCAGACAA | 420 |
| TCATYRTACA | TAAATCTGCA | AGCCAAAATA | AYCAGCTATT | AGCGGAGCGA | GCAYTRGGRG | 480 |
| CYYTGTACAA | GCATGCTAGA | TTAGCTGGCC | ATAACCTYAA | GGTAGARGAA | TGYTGGGTGT | 540 |
| CAGATTGTCT | GTATGAGTAT | GGAAAGAAGC | TYTTCTTCCG | TGGTGTACCT | GTCCCRGGCT | 600 |
| GTTTGAAGCA | GCTCTCRCGG | GTGACGGAYT | CYACTGGRGA | GYTATTCCCA | AACCTATACT | 660 |
| CAAAGTTAGC | CTGCTWAACA | TCATCRTGY | | | | 689 |

(2) INFORMATION FOR SEQ ID NO:18:

(i) SEQUENCE CHARACTERISTICS:
        (A) LENGTH: 689 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

TGACCATGAG CTCAACGGCT CTAACTCACC TTCTTAACCG GCTATCACAT ACTATCACTA      60

AGGGTGACTC CTTTGTTATT AACCTTGACT ATAGTTCCTG GTGCAACGGT TTCCGACCAG     120

AACTGCAGGC CCCAATCTGT CGTCAGTTGG ATCAGATGTT CAATTGCGGG TACTTCTTCA     180

GGACTGGGTG CACACTGCCA TGCTTTACCA CGTTTATTAT TCAAGACAGG TTCAACCCGC     240

CCTATTCCCT CAGTGGTGAG CCCGTTGAAG ACGGAGTTAC ATGCGCGGTT GGGACTAAAA     300

CAATGGGGGA GGGCATGAGG CAGAAACTAT GGACAATCCT TACGAGCTGC TGGGAGATAA     360

TTGCTCTTCG GGAAATTAAC GTGACGTTTA ACATACTAGG CCAAGGTGAT AATCAGACAA     420

TCATCATACA TAAATCTGCA AGCCAAAATA ACCAGCTATT AGCGGAGCGA GCACTAGGGG     480

CCCTGTACAA GCATGCTAGA TTAGCTGGCC ATAACCTCAA GGTAGAGGAA TGCTGGGTGT     540

CAGATTGTCT GTATGAGTAT GGAAAGAAGC TTTTCTTCCG TGGTGTACCT GTCCCGGGCT     600

GTTTGAAGCA GCTCTCACGG GTGACGGATT CTACTGGAGA GCTATTCCCA AACCTATACT     660

CAAAGTTAGC CTGCTTAACA TCATCATGC                                      689

(2) INFORMATION FOR SEQ ID NO:19:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

TGACCATGAG CTCAACGGCT CTAACTCACC TTCTTAACCG GCTATCACAT ACTATCACTA      60

AGGGTGACTC CTTTGTTATT AACCTTGACT ATAGTTCCTG GTGCAACGGT TTCCGACCAG     120

AACTGCAGGC CCCAATCTGT CGTCAGTTGG ATCAGATGTT CAATTGCGGG TACTTCTTCA     180

GGACTGGGTG CACACTGCCA TGCTTTACCA CGTTTATTAT TCAAGACAGG TTCAACCCGC     240

CCTATTCCCT CAGTGGTGAG CCCGTTGAAG ACGGAGTTAC ATGCGCGGTT GGGACTAAAA     300

CAATGGGGGA GGGCATGAGG CAGAAACTAT GGACAATCCT TACGAGCTGC TGGGAGATAA     360

TTGCTCTTCG GGAAATTAAC GTGACGTTTA ACATACTAGG CCAAGGTGAT AATCAGACAA     420

TCATCATACA TAAATCTGCA AGCCAAAATA ACCAGCTATT AGCGGAGCGA GCACTAGGGG     480

CCCTGTACAA GCATGCTAGA TTAGCTGGCC ATAACCTCAA GGTAGAGGAA TGCTGGGTGT     540

CAGATTGTCT GTATGAGTAT GGAAAGAAGC TTTTCTTCCG TGGTGTACCT GTCCCGGGCT     600

GTTTGAAGCA GCTCTCACGG GTGACGGATT CTACTGGAGA GCTATTCCCA AACCTATACT     660

CAAAGTTAGC CTGCTAAACA TCATCATGC                                      689

(2) INFORMATION FOR SEQ ID NO:20:
```

(i) SEQUENCE CHARACTERISTICS:
    (A) LENGTH: 201 amino acids
    (B) TYPE: amino acid
    (D) TOPOLOGY: linear (ii) MOLECULE TYPE: protein (xi) SEQUENCE DESCRIPTION: SEQ ID NO:20:

```
Met Ala Thr Glu Pro Ser Ser Leu Val Asp Ser Leu Glu Asp Glu Glu
 1               5                  10                  15

Asp Pro Gln Thr Leu Arg Arg Glu Arg Ser Gly Ser Pro Arg Pro Arg
             20                  25                  30

Lys Val Pro Arg Asn Ala Leu Thr Gln Pro Val Asp Gln Leu Leu Lys
         35                  40                  45

Asp Leu Arg Lys Asn Pro Ser Met Ile Ser Asp Pro Asp Gln Arg Thr
     50                  55                  60

Gly Arg Glu Gln Leu Ser Asn Asp Glu Leu Ile Lys Lys Leu Val Thr
 65                  70                  75                  80

Glu Leu Ala Glu Asn Ser Met Ile Glu Ala Glu Val Arg Gly Thr
                 85                  90                  95

Leu Gly Asp Ile Ser Ala Arg Ile Glu Ala Gly Phe Glu Ser Leu Ser
                100                 105                 110

Ala Leu Gln Val Glu Thr Ile Gln Thr Ala Gln Arg Cys Asp Tyr Ser
            115                 120                 125

Asp Ser Ile Arg Ile Leu Gly Glu Asn Ile Lys Ile Leu Asp Arg Ser
        130                 135                 140

Met Lys Thr Met Met Glu Thr Met Lys Leu Met Met Glu Lys Val Asp
145                 150                 155                 160

Leu Leu Tyr Ala Ser Thr Ala Val Gly Thr Ser Ala Pro Met Leu Pro
                165                 170                 175

Ser His Pro Ala Pro Pro Arg Ile Tyr Pro Gln Leu Pro Ser Ala Pro
            180                 185                 190

Thr Thr Asp Glu Trp Asp Ile Ile Pro
        195                 200
```

(2) INFORMATION FOR SEQ ID NO:21:

(i) SEQUENCE CHARACTERISTICS:
        (A) LENGTH: 201 amino acids
        (B) TYPE: amino acid
        (D) TOPOLOGY: linear (ii) MOLECULE TYPE: protein (xi) SEQUENCE DESCRIPTION: SEQ ID NO:21:

```
Met Ala Thr Gly Pro Ser Ser Leu Val Asp Ser Leu Glu Asp Glu Glu
 1               5                  10                  15

Asp Pro Gln Thr Leu Arg Arg Glu Arg Ser Gly Ser Pro Arg Pro Arg
             20                  25                  30

Lys Val Pro Arg Asn Ala Leu Thr Gln Pro Val Asp Gln Leu Leu Lys
         35                  40                  45

Asp Leu Arg Lys Asn Pro Ser Met Ile Ser Asp Pro Asp Gln Arg Thr
     50                  55                  60

Gly Arg Glu Gln Leu Ser Asn Asp Glu Leu Ile Lys Lys Leu Val Thr
 65                  70                  75                  80

Glu Leu Ala Glu Asn Ser Met Ile Glu Ala Glu Val Arg Gly Thr
                 85                  90                  95

Leu Gly Asp Ile Ser Ala Arg Ile Glu Ala Gly Phe Glu Ser Leu Ser
```

```
              100                 105                 110
Ala Leu Gln Val Glu Thr Ile Gln Thr Ala Gln Arg Cys Asp His Ser
            115                 120                 125

Asp Ser Ile Arg Ile Leu Gly Glu Asn Ile Lys Ile Leu Asp Arg Ser
    130                 135                 140

Met Lys Thr Met Met Glu Thr Met Lys Leu Met Met Glu Lys Val Asp
145                 150                 155                 160

Leu Leu Tyr Ala Ser Thr Ala Val Gly Thr Ser Ala Pro Met Leu Pro
                165                 170                 175

Ser His Pro Ala Pro Pro Arg Ile Tyr Pro Gln Leu Pro Ser Ala Pro
            180                 185                 190

Thr Thr Asp Glu Trp Asp Ile Ile Pro
            195                 200
```

(2) INFORMATION FOR SEQ ID NO:22:

(i) SEQUENCE CHARACTERISTICS:
        (A) LENGTH: 201 amino acids
        (B) TYPE: amino acid
        (D) TOPOLOGY: linear (ii) MOLECULE TYPE: protein (xi) SEQUENCE DESCRIPTION: SEQ ID NO:22:

```
Met Ala Thr Glu Pro Ser Ser Leu Val Asp Ser Leu Glu Asp Glu Glu
1               5                   10                  15

Asp Pro Gln Thr Leu Arg Arg Glu Arg Ser Gly Ser Pro Arg Pro Arg
                20                  25                  30

Lys Val Pro Arg Asn Ala Leu Thr Gln Pro Val Asp Gln Leu Leu Lys
            35                  40                  45

Asp Leu Arg Lys Asn Pro Ser Met Ile Ser Asp Pro Asp Gln Arg Thr
        50                  55                  60

Gly Arg Glu Gln Leu Ser Asn Asp Glu Leu Ile Lys Lys Leu Val Thr
65                  70                  75                  80

Glu Leu Ala Glu Asn Ser Met Ile Glu Ala Glu Val Arg Gly Thr
                85                  90                  95

Leu Gly Asp Ile Ser Ala Arg Ile Glu Ala Gly Phe Glu Ser Leu Ser
            100                 105                 110

Ala Leu Gln Val Glu Thr Ile Gln Thr Ala Gln Arg Cys Asp His Ser
            115                 120                 125

Asp Ser Ile Arg Ile Leu Gly Glu Asn Ile Lys Ile Leu Asp Arg Ser
    130                 135                 140

Met Lys Thr Met Met Glu Thr Met Lys Leu Met Met Glu Lys Val Asp
145                 150                 155                 160

Leu Leu Tyr Ala Ser Thr Ala Val Gly Thr Ser Ala Pro Met Leu Pro
                165                 170                 175

Ser His Pro Ala Pro Pro Arg Ile Tyr Pro Gln Leu Pro Ser Ala Pro
            180                 185                 190

Thr Thr Asp Glu Trp Asp Ile Ile Pro
            195                 200
```

(2) INFORMATION FOR SEQ ID NO:23:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:23:

Met Asn Ser Lys His Ser Tyr Val Glu Leu Lys Asp Lys Val Ile Val
1               5                  10                  15

Pro Gly Trp Pro Thr Leu Met Leu Glu Ile Asp Phe Val Gly Gly Thr
            20                  25                  30

Ser Arg Asn Gln Phe Leu Asn Ile Pro Phe Leu Ser Val Lys Glu Pro
        35                  40                  45

Leu Gln Leu Pro Arg Glu Lys Lys Leu Thr Asp Tyr Phe Thr Ile Asp
    50                  55                  60

Val Glu Pro Ala Gly His Ser Leu Val Asn Ile Tyr Phe Gln Ile Asp
65                  70                  75                  80

Asp Phe Leu Leu Leu Thr Leu Asn Ser Leu Ser Val Tyr Lys Asp Pro
                85                  90                  95

Ile Arg Lys Tyr Met Phe Leu Arg Leu Asn Lys Asp Gln Ser Lys His
            100                 105                 110

Ala Ile Asn Ala Ala Phe Asn Val Phe Ser Tyr Arg Leu Arg Asn Ile
        115                 120                 125

Gly Val Gly Pro Leu Gly Pro Asp Ile Arg Ser Ser Gly Pro
130                 135                 140

(2) INFORMATION FOR SEQ ID NO:24:

(i) SEQUENCE CHARACTERISTICS:
            (A) LENGTH: 142 amino acids
            (B) TYPE: amino acid
            (D) TOPOLOGY: linear (ii) MOLECULE TYPE: protein (xi) SEQUENCE DESCRIPTION: SEQ ID NO:24:

Met Asn Ser Lys His Ser Tyr Val Glu Leu Lys Asp Lys Val Ile Val
1               5                  10                  15

Pro Gly Trp Pro Thr Leu Met Leu Glu Ile Asp Phe Val Gly Gly Thr
            20                  25                  30

Ser Arg Asn Gln Phe Leu Asn Ile Pro Phe Leu Ser Val Lys Glu Pro
        35                  40                  45

Leu Gln Leu Pro Arg Glu Lys Lys Leu Thr Asp Tyr Phe Thr Ile Asp
    50                  55                  60

Val Glu Pro Ala Gly His Ser Leu Val Asn Ile Tyr Phe Gln Ile Asp
65                  70                  75                  80

Asp Phe Leu Leu Leu Thr Leu Asn Ser Leu Ser Val Tyr Lys Asp Pro
                85                  90                  95

Ile Arg Lys Tyr Met Phe Leu Arg Leu Asn Lys Asp Gln Ser Lys His
            100                 105                 110

Ala Ile Asn Ala Ala Phe Asn Val Phe Ser Tyr Arg Leu Arg Asn Ile
        115                 120                 125

Gly Val Gly Pro Leu Gly Pro Asp Ile Arg Ser Ser Gly Pro
130                 135                 140

(2) INFORMATION FOR SEQ ID NO:25:

(i) SEQUENCE CHARACTERISTICS:
            (A) LENGTH: 142 amino acids
            (B) TYPE: amino acid
            (D) TOPOLOGY: linear (ii) MOLECULE TYPE: protein (xi) SEQUENCE DESCRIPTION: SEQ ID NO:25:

```
Met Asn Ser Lys His Ser Tyr Val Glu Leu Lys Asp Lys Val Ile Val
1               5                   10                  15

Pro Gly Trp Pro Thr Leu Met Leu Glu Ile Gly Phe Val Gly Gly Thr
            20                  25                  30

Ser Arg Asn Gln Phe Leu Asn Ile Pro Phe Leu Ser Val Lys Glu Pro
        35                  40                  45

Leu Gln Leu Pro Arg Glu Lys Lys Leu Thr Asp Tyr Phe Thr Ile Asp
    50                  55                  60

Val Glu Pro Ala Gly His Ser Leu Val Asn Ile Tyr Phe Gln Ile Asp
65                  70                  75                  80

Asp Phe Leu Leu Thr Leu Asn Ser Ser Leu Val Tyr Lys Asp Pro
                85                  90                  95

Ile Arg Lys Tyr Met Phe Leu Arg Leu Asn Lys Asp Gln Ser Lys His
                100                 105                 110

Ala Ile Asn Ala Ala Phe Asn Val Phe Ser Tyr Arg Leu Arg Asn Ile
            115                 120                 125

Gly Val Gly Pro Leu Gly Pro Asp Ile Arg Ser Ser Gly Pro
    130                 135                 140
```

(2) INFORMATION FOR SEQ ID NO:26:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:26:

```
Met Gln Pro Ser Met Ser Phe Leu Ile Gly Phe Gly Thr Leu Val Leu
1               5                   10                  15

Val Leu Ser Ala Arg Thr Phe Asp Leu Gln Gly Leu Ser Cys Asn Thr
            20                  25                  30

Asp Ser Thr Pro Gly Leu Ile Asp Leu Glu Ile Arg Arg Leu Cys His
        35                  40                  45

Thr Pro Thr Glu Asn Val Ile Ser Cys Glu Val Ser Tyr Leu Asn His
    50                  55                  60

Thr Thr Ile Ser Leu Pro Ala Val His Thr Ser Cys Leu Lys Tyr His
65                  70                  75                  80

Cys Lys Thr Tyr Trp Gly Phe Phe Gly Ser Tyr Ser Ala Asp Arg Ile
                85                  90                  95

Ile Asn Arg Tyr Thr Gly Thr Val Lys Gly Cys Leu Asn Asn Ser Ala
                100                 105                 110

Pro Glu Asp Pro Phe Glu Cys Asn Trp Phe Tyr Cys Cys Ser Ala Ile
            115                 120                 125

Thr Thr Glu Ile Cys Arg Cys Ser Ile Thr Asn Val Thr Val Ala Val
    130                 135                 140

Gln Thr Phe Pro Pro Phe Met Tyr Cys Ser Phe Ala Asp Cys Ser Thr
145                 150                 155                 160

Val Ser Gln Gln Glu Leu Glu Ser Gly Lys Ala Met Leu Ser Asp Gly
                165                 170                 175

Ser Thr Leu Thr Tyr Thr Pro Tyr Ile Leu Gln Ser Glu Val Val Asn
                180                 185                 190

Lys Thr Leu Asn Gly Thr Ile Leu Cys Asn Ser Ser Ser Lys Ile Val
```

-continued 195                 200                 205

Ser Phe Asp Glu Phe Arg Arg Ser Tyr Ser Leu Thr Asn Gly Ser Tyr
    210                 215                 220

Gln Ser Ser Ser Ile Asn Val Thr Cys Ala Asn Tyr Thr Ser Ser Cys
225                 230                 235                 240

Arg Pro Arg Leu Lys Arg Arg Arg Asp Thr Gln Gln Ile Glu Tyr
                245                 250                 255

Leu Val His Lys Leu Arg Pro Thr Leu Lys Asp Ala Trp Glu Asp Cys
            260                 265                 270

Glu Ile Leu Gln Ser Leu Leu Gly Val Phe Gly Thr Gly Ile Ala
        275                 280                 285

Ser Ala Ser Gln Phe Leu Arg Ser Trp Leu Asn His Pro Asp Ile Ile
    290                 295                 300

Gly Tyr Ile Val Asn Gly Val Gly Val Val Trp Gln Cys His Arg Val
305                 310                 315                 320

Asn Val Thr Phe Met Thr Trp Asn Glu Ser Thr Tyr Tyr Pro Pro Val
                325                 330                 335

Asp Tyr Asn Gly Arg Lys Tyr Phe Leu Asn Asp Glu Gly Arg Leu Gln
            340                 345                 350

Thr Asn Thr Pro Glu Ala Arg Pro Gly Leu Lys Arg Val Met Trp Phe
        355                 360                 365

Gly Arg Tyr Phe Leu Gly Thr Val Gly Ser Gly Val Lys Pro Arg Arg
    370                 375                 380

Ile Arg Tyr Asn Lys Thr Ser His Asp Tyr His Leu Glu Glu Phe Glu
385                 390                 395                 400

Ala Ser Leu Asn Met Thr Pro Gln Thr Ser Ile Thr Ser Gly His Glu
                405                 410                 415

Thr Asp Pro Ile Asn His Ala Tyr Gly Thr Gln Ala Asp Leu Leu Pro
            420                 425                 430

Tyr Thr Arg Ser Ser Asn Ile Thr Ser Thr Asp Thr Gly Ser Gly Trp
        435                 440                 445

Val His Ile Gly Leu Pro Ser Phe Ala Phe Leu Asn Pro Leu Gly Trp
    450                 455                 460

Leu Arg Asp Leu Leu Ala Trp Ala Ala Trp Leu Gly Gly Val Leu Tyr
465                 470                 475                 480

Leu Ile Ser Leu Cys Val Ser Leu Pro Ala Ser Phe Ala Arg Arg
                485                 490                 495

Arg Leu Gly Arg Leu Gln Glu
            500

(2) INFORMATION FOR SEQ ID NO:27:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:27:

Met Gln Pro Ser Met Ser Phe Leu Ile Gly Phe Gly Thr Leu Val Leu
1               5                   10                  15

Val Leu Ser Ala Arg Thr Phe Asp Leu Gln Gly Leu Ser Cys Asn Thr
            20                  25                  30

Asp Ser Thr Pro Gly Leu Ile Asp Leu Glu Ile Arg Arg Leu Cys His
        35                  40                  45

```
Thr Pro Thr Glu Asn Val Ile Ser Cys Glu Val Ser Tyr Leu Asn His
 50                  55                  60
Thr Thr Ile Ser Leu Pro Ala Val His Thr Ser Cys Leu Lys Tyr His
 65              70                  75                      80
Cys Lys Thr Tyr Trp Gly Phe Gly Ser Tyr Ser Ala Asp Arg Ile
                 85                  90                  95
Ile Asn Arg Tyr Thr Gly Thr Val Lys Gly Cys Leu Asn Asn Ser Ala
            100                 105                 110
Pro Glu Asp Pro Phe Glu Cys Asn Trp Phe Tyr Cys Cys Ser Ala Ile
        115                 120                 125
Thr Thr Glu Ile Cys Arg Cys Ser Ile Thr Asn Val Thr Val Ala Val
    130                 135                 140
Gln Thr Phe Pro Pro Phe Met Tyr Cys Ser Phe Ala Asp Cys Ser Thr
145                 150                 155                 160
Val Ser Gln Gln Glu Leu Glu Ser Gly Lys Ala Met Leu Ser Asp Gly
                165                 170                 175
Ser Thr Leu Thr Tyr Thr Pro Tyr Ile Leu Gln Ser Glu Val Val Asn
            180                 185                 190
Lys Thr Leu Asn Gly Thr Ile Leu Cys Asn Ser Ser Lys Ile Val
        195                 200                 205
Ser Phe Asp Glu Phe Arg Arg Ser Tyr Ser Leu Thr Asn Gly Ser Tyr
210                 215                 220
Gln Ser Ser Ser Ile Asn Val Thr Cys Ala Asn Tyr Thr Ser Ser Cys
225                 230                 235                 240
Arg Pro Arg Leu Lys Arg Arg Arg Asp Thr Gln Gln Ile Glu Tyr
                245                 250                 255
Leu Val His Lys Leu Arg Pro Thr Leu Lys Asp Ala Trp Glu Asp Cys
            260                 265                 270
Glu Ile Leu Gln Ser Leu Leu Leu Gly Val Phe Gly Thr Gly Ile Ala
        275                 280                 285
Ser Ala Ser Gln Phe Leu Arg Ser Trp Leu Asn His Pro Asp Ile Ile
    290                 295                 300
Gly Tyr Ile Val Asn Gly Val Gly Val Trp Gln Cys His Arg Val
305                 310                 315                 320
Asn Val Thr Phe Met Thr Trp Asn Glu Ser Thr Tyr Tyr Pro Pro Val
                325                 330                 335
Asp Tyr Asn Gly Arg Lys Tyr Phe Leu Asn Asp Glu Gly Arg Leu Gln
            340                 345                 350
Thr Asn Thr Pro Glu Ala Arg Pro Gly Leu Lys Arg Val Met Trp Phe
        355                 360                 365
Gly Arg Tyr Phe Leu Gly Thr Val Gly Ser Gly Val Lys Pro Arg Arg
    370                 375                 380
Ile Arg Tyr Asn Lys Thr Ser His Asp Tyr His Leu Glu Glu Phe Glu
385                 390                 395                 400
Ala Ser Leu Asn Met Thr Pro Gln Thr Ser Ile Ala Ser Gly His Glu
                405                 410                 415
Thr Asp Pro Ile Asn His Ala Tyr Gly Thr Gln Ala Asp Leu Leu Pro
            420                 425                 430
Tyr Thr Arg Ser Ser Asn Ile Thr Ser Thr Asp Thr Gly Ser Gly Trp
        435                 440                 445
Val His Ile Gly Leu Pro Ser Phe Ala Phe Leu Asn Pro Leu Gly Trp
    450                 455                 460
```

```
Leu Arg Asp Leu Leu Ala Trp Ala Ala Trp Leu Gly Val Leu Tyr
465                 470                 475                 480

Leu Ile Ser Leu Cys Val Ser Leu Pro Ala Ser Phe Ala Arg Arg
                485                 490                 495

Arg Leu Gly Arg Trp Gln Glu
            500
```

(2) INFORMATION FOR SEQ ID NO:28:

(i) SEQUENCE CHARACTERISTICS:
        (A) LENGTH: 189 amino acids
        (B) TYPE: amino acid
        (D) TOPOLOGY: linear (ii) MOLECULE TYPE: protein (xi) SEQUENCE DESCRIPTION: SEQ ID NO:28:

```
His Thr Val Thr Pro Ser Leu Val Phe Leu Cys Leu Leu Ile Pro Gly
1               5                   10                  15

Leu His Ala Ala Phe Val His Gly Gly Val Pro Arg Glu Ser Tyr Leu
            20                  25                  30

Ser Thr Pro Val Thr Arg Gly Glu Gln Thr Val Val Lys Thr Ala Lys
        35                  40                  45

Phe Tyr Gly Glu Lys Thr Thr Gln Arg Asp Leu Thr Glu Leu Glu Ile
50                  55                  60

Ser Ser Ile Phe Ser His Cys Cys Ser Leu Leu Ile Gly Val Val Ile
65                  70                  75                  80

Gly Ser Ser Ser Lys Ile Lys Ala Gly Ala Glu Gln Ile Lys Lys Arg
                85                  90                  95

Phe Lys Thr Met Met Ala Ala Leu Asn Arg Pro Ser His Gly Glu Thr
                100                 105                 110

Ala Thr Leu Leu Gln Met Phe Asn Pro His Glu Ala Ile Asp Trp Ile
            115                 120                 125

Asn Gly Gln Pro Trp Val Gly Ser Phe Val Leu Pro Leu Leu Thr Thr
130                 135                 140

Asp Phe Glu Ser Pro Gly Lys Glu Phe Met Asp Gln Ile Lys Leu Val
145                 150                 155                 160

Ala Ser Tyr Ala Gln Met Thr Thr Tyr Thr Thr Ile Lys Glu Tyr Leu
                165                 170                 175

Ala Glu Cys Met Asp Ala Thr Leu Thr Ile Pro Val Val
            180                 185
```

(2) INFORMATION FOR SEQ ID NO:29:

(i) SEQUENCE CHARACTERISTICS:
        (A) LENGTH: 189 amino acids
        (B) TYPE: amino acid
        (D) TOPOLOGY: linear (ii) MOLECULE TYPE: protein (xi) SEQUENCE DESCRIPTION: SEQ ID NO:29:

```
His Thr Val Thr Pro Ser Leu Val Phe Leu Cys Leu Leu Ile Pro Gly
1               5                   10                  15

Leu His Ala Ala Phe Val His Gly Gly Val Pro Arg Glu Ser Tyr Leu
            20                  25                  30

Ser Thr Pro Ile Thr Arg Gly Glu Gln Thr Val Val Lys Thr Ala Glu
        35                  40                  45

Phe Tyr Gly Glu Lys Thr Thr Gln Arg Asp Leu Thr Glu Leu Glu Ile
```

```
           50                  55                  60
Ser Ser Ile Phe Ser His Cys Cys Ser Leu Leu Ile Gly Val Val Ile
 65                  70                  75                  80

Gly Ser Ser Ser Lys Ile Lys Ala Glu Ala Glu Gln Ile Lys Lys Arg
                 85                  90                  95

Phe Lys Thr Met Met Ala Ala Val Asn Arg Pro Ser His Gly Glu Thr
                100                 105                 110

Ala Thr Leu Leu Gln Met Phe Asn Pro His Glu Ala Ile Asp Trp Ile
                115                 120                 125

Asn Gly Gln Pro Trp Val Gly Ser Phe Val Leu Ser Leu Leu Thr Thr
130                 135                 140

Asp Phe Glu Ser Pro Gly Lys Glu Phe Met Asp Gln Ile Lys Leu Val
145                 150                 155                 160

Ala Ser Tyr Ala Gln Met Thr Thr Tyr Thr Thr Ile Lys Glu Tyr Leu
                165                 170                 175

Ala Glu Cys Met Asp Ala Thr Leu Thr Ile Pro Val Val
                180                 185
```

(2) INFORMATION FOR SEQ ID NO:30:

(i) SEQUENCE CHARACTERISTICS:
        (A) LENGTH: 189 amino acids
        (B) TYPE: amino acid
        (D) TOPOLOGY: linear (ii) MOLECULE TYPE: protein (xi) SEQUENCE DESCRIPTION: SEQ ID NO:30:

```
His Thr Val Thr Pro Ser Leu Val Phe Leu Cys Leu Leu Ile Pro Gly
 1               5                  10                  15

Leu His Ala Ala Phe Val His Gly Gly Val Pro Arg Glu Ser Tyr Leu
                20                  25                  30

Ser Thr Pro Ile Thr Arg Gly Glu Gln Thr Val Val Lys Thr Ala Lys
                35                  40                  45

Phe Tyr Gly Glu Lys Thr Thr Gln Arg Asp Leu Thr Glu Leu Glu Ile
 50                  55                  60

Ser Ser Ile Phe Ser His Cys Cys Ser Leu Leu Ile Gly Val Val Ile
 65                  70                  75                  80

Gly Ser Ser Ser Lys Ile Lys Ala Gly Ala Glu Gln Ile Lys Lys Arg
                 85                  90                  95

Phe Lys Thr Met Met Ala Ala Leu Asn Arg Pro Ser His Gly Glu Thr
                100                 105                 110

Ala Thr Leu Leu Gln Met Phe Asn Pro His Glu Ala Ile Asp Trp Ile
                115                 120                 125

Asn Gly Gln Pro Trp Val Gly Ser Phe Val Leu Ser Leu Leu Thr Thr
130                 135                 140

Asp Phe Glu Ser Pro Gly Lys Glu Phe Met Asp Gln Ile Lys Leu Val
145                 150                 155                 160

Ala Ser Tyr Ala Gln Met Thr Thr Tyr Thr Thr Ile Lys Glu Tyr Leu
                165                 170                 175

Ala Glu Cys Met Asp Ala Thr Leu Thr Ile Pro Val Val
                180                 185
```

(2) INFORMATION FOR SEQ ID NO:31:

(i) SEQUENCE CHARACTERISTICS:
        (A) LENGTH: 229 amino acids (B) TYPE: amino acid
            (D) TOPOLOGY: linear (ii) MOLECULE TYPE: protein (xi) SEQUENCE DESCRIPTION: SEQ ID NO:31:

Thr Met Ser Ser Thr Ala Leu Thr His Leu Leu Asn Arg Leu Ser His
1               5                   10                  15

Thr Ile Thr Lys Gly Asp Ser Phe Val Ile Asn Leu Asp Tyr Ser Ser
            20                  25                  30

Trp Cys Asn Gly Phe Arg Pro Glu Leu Gln Ala Pro Ile Cys Arg Gln
        35                  40                  45

Leu Asp Gln Met Phe Asn Cys Gly Tyr Phe Arg Thr Gly Cys Thr
    50                  55                  60

Leu Pro Cys Phe Thr Thr Phe Ile Ile Gln Asp Arg Phe Asn Pro Pro
65                  70                  75                  80

Tyr Ser Leu Ser Gly Glu Pro Val Glu Asp Gly Val Thr Cys Ala Val
                85                  90                  95

Gly Thr Lys Thr Met Gly Glu Gly Met Arg Gln Lys Leu Trp Thr Ile
            100                 105                 110

Leu Thr Ser Cys Trp Glu Ile Ile Ala Leu Arg Glu Ile Asn Val Thr
            115                 120                 125

Phe Asn Ile Leu Gly Gln Gly Asp Asn Gln Thr Ile Ile Ile His Lys
130                 135                 140

Ser Ala Ser Gln Asn Asn Gln Leu Leu Ala Glu Arg Ala Leu Gly Ala
145                 150                 155                 160

Leu Tyr Lys His Ala Arg Leu Ala Gly His Asn Leu Lys Val Glu Glu
                165                 170                 175

Cys Trp Val Ser Asp Cys Leu Tyr Glu Tyr Gly Lys Lys Leu Phe Phe
            180                 185                 190

Arg Gly Val Pro Val Pro Gly Cys Leu Lys Gln Leu Ser Arg Val Thr
            195                 200                 205

Asp Ser Thr Gly Glu Leu Phe Pro Asn Leu Tyr Ser Lys Leu Ala Cys
    210                 215                 220

Leu Thr Ser Ser Cys
225

(2) INFORMATION FOR SEQ ID NO:32:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:32:

Met Ala Thr Gly Pro Ser Ser Leu Val Asp Ser Leu Glu Asp Glu
1               5                   10                  15

Asp Pro (2) INFORMATION FOR SEQ ID NO:33:

(i) SEQUENCE CHARACTERISTICS:
        (A) LENGTH: 19 amino acids
        (B) TYPE: amino acid
        (D) TOPOLOGY: linear

```
    (ii) MOLECULE TYPE: peptide (v) FRAGMENT TYPE: internal (xi) SEQUENCE DESCRIPTION: SEQ ID NO:33:

Arg Ile Tyr Pro Gln Leu Pro Ser Ala Pro Thr Ala Asp Glu Trp Asp
1               5                  10                  15

Ile Ile Pro (2) INFORMATION FOR SEQ ID NO:34:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:34:

Met Asn Ser Lys His Ser Tyr Val Glu Leu Lys Gly Lys Val Ile Val
1               5                  10                  15

Pro Gly (2) INFORMATION FOR SEQ ID NO:35:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

Arg Leu Arg Asn Ile Gly Val Gly Pro Leu Gly Pro Asp Ile Arg Ser
1               5                  10                  15

Ser Gly Pro (2) INFORMATION FOR SEQ ID NO:36:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

Gly Leu Ser Cys Asn Thr Asp Ser Thr Pro Gly Leu Ile Asp Leu Glu
1               5                  10                  15

Ile Arg (2) INFORMATION FOR SEQ ID NO:37:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal
```

(xi) SEQUENCE DESCRIPTION: SEQ ID NO:37:

Arg Ser Lys Leu Arg Arg Arg Arg Asp Thr Gln Gln Ile Glu Tyr
1               5                   10                  15

Leu Val (2) INFORMATION FOR SEQ ID NO:38:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:38:

Leu Ile Ser Leu Cys Val Ser Leu Pro Ala Ser Phe Ala Arg Arg Arg
1               5                   10                  15

Arg Leu Gly Arg Trp Gln Glu
            20

(2) INFORMATION FOR SEQ ID NO:39:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:39:

Met Pro Pro Lys Arg Arg Leu Val Asp Asp Ala Asp Ala Met Glu Asp
1               5                   10                  15

Gln Asp (2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:40:

Met Glu Asp Gln Asp Asp Leu Tyr Glu Pro Pro Ala Ser Leu Pro Lys
1               5                   10                  15

Leu Pro (2) INFORMATION FOR SEQ ID NO:41:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:41:

```
Glu Leu Ser Gly Glu Ile Ser Ala Ile Met Arg Met Ile Gly Val Thr
1               5                  10                 15

Gly Leu Val
```

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:42:

CAGGAGGCTC AATGGCAACG        20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:43:

TTTATGGTAT GATGTCCCAC        20

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:44:

ATCGAATCAC CATGAATTCA AAGC        24

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:45:

GTCAGTATTG CAACTAAGGC                                       20

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:46:

GCACGCAATT AATGCAGC                                         18

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:47:

CAGTGTAGGC CTAAGCTTGT G                                     21

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:48:

AAGTTGAGAA GGCGGCGTAG                                       20

(2) INFORMATION FOR SEQ ID NO:49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:49:

CGGTACGGTT TATTCCTGC                                        19

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:50:

TGACCATGAG CTCAACGGC                                            19

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:51:

GCATGATGAT GTTAAGCAGG C                                         21

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:52:

TTCATACAGT AACGCCCAGC                                           20

(2) INFORMATION FOR SEQ ID NO:53:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:53:

GCAACTACAG GGATTGTAAG GG                                        22

(2) INFORMATION FOR SEQ ID NO:54:

```
       (i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:54:

GCCTTGTGTT TCTATGTTTG C                                                     21

(2) INFORMATION FOR SEQ ID NO:55:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:55:

GCATCCATAC ATTCTGCGAG                                                       20

(2) INFORMATION FOR SEQ ID NO:56:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:56:

CGAATTCGCA CGCAATTAAT GCAGC                                                 25

(2) INFORMATION FOR SEQ ID NO:57:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:57:

GCTACTCGAG CGGTACGGTT TATTCCTGC                                             29

(2) INFORMATION FOR SEQ ID NO:58:

(i) SEQUENCE CHARACTERISTICS:
           (A) LENGTH: 33 base pairs
           (B) TYPE: nucleic acid
```

(C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:58:

CCCCCCGGGC AATGTACTGC AGTTTCGCGG ACT                                    33

(2) INFORMATION FOR SEQ ID NO:59:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:59:

GGGCCCGGGT TATTCCTGCC ACCGGCCGA                                         29

(2) INFORMATION FOR SEQ ID NO:60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:60:

ATGCCACCCG GGAGACGCCT GATTGAT                                           27

(2) INFORMATION FOR SEQ ID NO:61:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:61:

CGGATCCCGG GCTAGTTTAG ACCAGTCACT CC                                     32

(2) INFORMATION FOR SEQ ID NO:62:

(i) SEQUENCE CHARACTERISTICS:
        (A) LENGTH: 42 base pairs
        (B) TYPE: nucleic acid
        (C) STRANDEDNESS: single
        (D) TOPOLOGY: linear -continued (ii) MOLECULE TYPE: cDNA (iii) HYPOTHETICAL: NO (iv) ANTI-SENSE: NO (xi) SEQUENCE DESCRIPTION: SEQ ID NO:62:

GGCCATATGC GCCCGGGCCC ATCGAGTCTG GTCGACTCCC TG    42

(2) INFORMATION FOR SEQ ID NO:63:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:63:

CTCGAGCCCG GGTTATGGTA TGATGTCCCA CTCATC    36

(2) INFORMATION FOR SEQ ID NO:64:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:64:

CGAATCCCCG GGAATTCAAA GCATTCCTA    29

(2) INFORMATION FOR SEQ ID NO:65:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:65:

TCCCCCCGGG CAGTATTGCA ACTAACGG    28